US012653522B2

(12) United States Patent
Hauck et al.

(10) Patent No.: US 12,653,522 B2
(45) Date of Patent: Jun. 16, 2026

(54) VASCULAR CLOSURE DEVICES AND METHODS

(71) Applicant: Arterica Inc., Santa Rosa, CA (US)

(72) Inventors: Brian Hauck, Windsor, CA (US); Robert Carter, Petaluma, CA (US); Dion Thurow, Santa Rosa, CA (US); Joseph W. Humphrey, Santa Rosa, CA (US); Robert G. Whirley, Santa Rosa, CA (US); Thomas Larzon, Lidingö (SE)

(73) Assignee: ARTERICA, INC, Santa Rosa, CA (US)

( * ) Notice: Subject to any disclaimer, the term of this patent is extended or adjusted under 35 U.S.C. 154(b) by 127 days.

(21) Appl. No.: 18/431,814

(22) Filed: Feb. 2, 2024

(65) Prior Publication Data

US 2024/0173527 A1 May 30, 2024

Related U.S. Application Data

(62) Division of application No. 16/951,886, filed on Nov. 18, 2020, now Pat. No. 11,938,288.

(Continued)

(51) Int. Cl.
A61B 17/04 (2006.01)
A61B 17/00 (2006.01)
(52) U.S. Cl.
CPC ...... A61B 17/0467 (2013.01); A61B 17/0487 (2013.01); A61B 2017/00623 (2013.01);
(Continued)

(58) Field of Classification Search
CPC ............ A61B 17/0467; A61B 17/0401; A61B 17/0057; A61B 17/0487; A61B 17/0469; A61B 2017/00367; A61B 2017/0061; A61B 2017/00623; A61B 2017/00663; A61B 2017/0409; A61B 2017/00575; A61B 2017/00579; A61B 2017/00584;
(Continued)

(56) References Cited

U.S. PATENT DOCUMENTS

| | | | |
|---|---|---|---|
| 5,108,421 A | 4/1992 | Fowler | |
| 5,364,408 A | 11/1994 | Gordon | |

(Continued)

FOREIGN PATENT DOCUMENTS

| | | |
|---|---|---|
| EP | 2095774 | 9/2009 |
| EP | 2308521 | 4/2011 |

(Continued)

OTHER PUBLICATIONS

Non-Final Office Action Dated: May 20, 2025 in U.S. Appl. No. 18/213,636, filed Jun. 23, 2023 and 1 published as: 2023-0329688 on Oct. 19, 2023, examiner: Shaun L. David.

(Continued)

*Primary Examiner* — Dianne Dornbusch
(74) *Attorney, Agent, or Firm* — Schmeiser, Olsen & Watts LLP

(57) ABSTRACT

Vascular closure assembly embodiments may be used to provide hemostasis at vascular puncture sites or the like. Such vascular puncture or access sites may be created during a variety of percutaneous or minimally invasive medical procedures.

12 Claims, 46 Drawing Sheets

Related U.S. Application Data

(60) Provisional application No. 62/937,675, filed on Nov. 19, 2019.

(52) U.S. Cl.
CPC .............. *A61B 2017/00663* (2013.01); *A61B 2017/0409* (2013.01); *A61B 2017/0488* (2013.01)

(58) Field of Classification Search
CPC .......... A61B 2017/00588; A61B 2017/00592; A61B 2017/00597; A61B 2017/00601; A61B 2017/00615; A61B 2017/00619; A61B 2017/0068; A61B 2017/00628; A61B 2017/00632; A61B 2017/00637; A61B 2017/0064; A61B 2017/00646; A61B 2017/00641; A61B 2017/0454; A61B 2017/0467; A61B 2017/0445; A61B 2017/0438; A61B 2017/0488; A61M 25/003; A61M 25/10185; A61M 2039/2473
See application file for complete search history.

(56) References Cited

U.S. PATENT DOCUMENTS

| | | | |
|---|---|---|---|
| 5,391,183 A | 2/1995 | Janzen et al. | |
| 5,413,571 A | 5/1995 | Katsaros et al. | |
| 5,417,699 A | 5/1995 | Klein et al. | |
| 5,501,667 A | 3/1996 | Verduin, Jr. | |
| 5,507,744 A | 4/1996 | Tay et al. | |
| 5,507,755 A | 4/1996 | Gresl et al. | |
| 5,540,704 A | 7/1996 | Gordon et al. | |
| 5,626,601 A | 5/1997 | Gershony et al. | |
| 5,700,273 A | 12/1997 | Buelna et al. | |
| 5,716,375 A | 2/1998 | Fowler | |
| 5,725,551 A | 3/1998 | Meyers et al. | |
| 5,728,134 A | 3/1998 | Barak | |
| 5,730,725 A | 3/1998 | Yoon | |
| 5,807,326 A | 9/1998 | O'Neill et al. | |
| 5,836,913 A | 11/1998 | Orth et al. | |
| 5,860,990 A | 1/1999 | Nobles et al. | |
| 5,868,762 A | 2/1999 | Cragg et al. | |
| 6,048,357 A | 4/2000 | Kontos | |
| 6,048,358 A | 4/2000 | Barak | |
| 6,059,800 A | 5/2000 | Hart et al. | |
| 6,077,279 A | 6/2000 | Kontos | |
| 6,110,184 A | 8/2000 | Weadock | |
| 6,132,397 A | 10/2000 | Davis et al. | |
| 6,231,561 B1 | 5/2001 | Frazier et al. | |
| 6,238,412 B1 | 5/2001 | Dubrul et al. | |
| 6,328,758 B1 | 12/2001 | Tornier et al. | |
| 6,436,088 B2 | 8/2002 | Frazier | |
| 6,461,366 B1 | 10/2002 | Seguin | |
| 6,562,052 B2 | 5/2003 | Nobles | |
| 6,622,367 B1 | 9/2003 | Bolduc et al. | |
| 6,626,918 B1 | 9/2003 | Ginn et al. | |
| 6,626,930 B1* | 9/2003 | Allen ................. A61B 17/0401 606/213 | |
| 6,669,719 B2 | 12/2003 | Wallace et al. | |
| 6,951,555 B1 | 10/2005 | Suresh et al. | |
| 7,458,978 B1 | 12/2008 | Bender et al. | |
| 7,789,893 B2 | 9/2010 | Drasler et al. | |
| 8,252,005 B2* | 8/2012 | Findlay, III ........ A61B 17/0467 606/139 | |
| 8,414,528 B2 | 4/2013 | Liu et al. | |
| 8,439,878 B2 | 5/2013 | Bonnette et al. | |
| 8,617,204 B2 | 12/2013 | Khosravi et al. | |
| 8,628,490 B2 | 1/2014 | Yacoubian et al. | |
| 8,821,532 B2 | 9/2014 | Schaeffer | |
| 8,920,442 B2 | 12/2014 | Sibbitt, Jr. et al. | |
| 9,017,374 B2 | 4/2015 | Yassinzadeh | |
| 9,687,216 B2 | 6/2017 | Sawhney et al. | |
| 9,782,156 B2 | 10/2017 | Larzon et al. | |
| 11,375,994 B2 | 7/2022 | Fortson | |
| 2002/0026208 A1 | 2/2002 | Roe et al. | |
| 2002/0045908 A1 | 4/2002 | Nobles et al. | |
| 2002/0077581 A1 | 6/2002 | Davidner et al. | |
| 2003/0233120 A1 | 12/2003 | Akerfeldt | |
| 2004/0087967 A1 | 5/2004 | Schur et al. | |
| 2004/0097978 A1 | 5/2004 | Modesitt et al. | |
| 2004/0220522 A1 | 11/2004 | Brisco et al. | |
| 2005/0121042 A1 | 6/2005 | Belhe et al. | |
| 2005/0149066 A1 | 7/2005 | Stafford | |
| 2005/0155608 A1 | 7/2005 | Pavcnik et al. | |
| 2005/0251155 A1 | 11/2005 | Orban, III | |
| 2005/0267528 A1 | 12/2005 | Ginn et al. | |
| 2006/0069397 A1 | 3/2006 | Nobles et al. | |
| 2006/0089627 A1 | 4/2006 | Burnett et al. | |
| 2006/0135991 A1 | 6/2006 | Kawaura et al. | |
| 2006/0142784 A1 | 6/2006 | Kontos | |
| 2007/0049967 A1 | 3/2007 | Sibbitt, Jr. et al. | |
| 2007/0083231 A1 | 4/2007 | Lee | |
| 2007/0112425 A1 | 5/2007 | Schaller et al. | |
| 2007/0203506 A1 | 8/2007 | Sibbitt et al. | |
| 2007/0203507 A1 | 8/2007 | McLaughlin et al. | |
| 2007/0213616 A1 | 9/2007 | Anderson et al. | |
| 2007/0276413 A1 | 11/2007 | Nobels | |
| 2008/0082122 A1 | 4/2008 | Khosravi et al. | |
| 2008/0097509 A1 | 4/2008 | Beyar et al. | |
| 2008/0147112 A1 | 6/2008 | Sheets et al. | |
| 2008/0154303 A1 | 6/2008 | Yassinzadeh | |
| 2008/0177227 A1 | 7/2008 | Wilkins | |
| 2008/0177288 A1* | 7/2008 | Carlson .............. A61B 17/3421 606/144 |
| 2008/0287988 A1 | 11/2008 | Smith et al. | |
| 2008/0294001 A1 | 11/2008 | Surti | |
| 2008/0300629 A1 | 12/2008 | Surti | |
| 2009/0143808 A1 | 6/2009 | Houset | |
| 2009/0248056 A1 | 10/2009 | Gabel et al. | |
| 2009/0254110 A1 | 10/2009 | Bagaoisan et al. | |
| 2009/0254119 A1 | 10/2009 | Sibbitt, Jr. et al. | |
| 2009/0264922 A1 | 10/2009 | Mas | |
| 2009/0306685 A1 | 12/2009 | Fill | |
| 2009/0318936 A1 | 12/2009 | Harris et al. | |
| 2010/0042118 A1 | 2/2010 | Garrison et al. | |
| 2010/0179572 A1 | 7/2010 | Voss et al. | |
| 2010/0179590 A1 | 7/2010 | Fortson et al. | |
| 2010/0217308 A1 | 8/2010 | Hanson | |
| 2010/0217311 A1 | 8/2010 | Jenson et al. | |
| 2010/0217312 A1 | 8/2010 | Hill et al. | |
| 2010/0262166 A1 | 10/2010 | Boraiah et al. | |
| 2011/0077668 A1 | 3/2011 | Gordon et al. | |
| 2011/0218568 A1 | 9/2011 | Voss | |
| 2011/0238090 A1 | 9/2011 | Heneveld | |
| 2011/0301619 A1 | 12/2011 | Walters | |
| 2012/0010633 A1 | 1/2012 | Noda et al. | |
| 2012/0158045 A1 | 6/2012 | Pipenhagen | |
| 2012/0290001 A1 | 11/2012 | Uchida et al. | |
| 2012/0296373 A1 | 11/2012 | Roorda et al. | |
| 2013/0006297 A1 | 1/2013 | Drasler | |
| 2013/0123812 A1 | 5/2013 | Tegels | |
| 2013/0123844 A1 | 5/2013 | White | |
| 2013/0190812 A1 | 7/2013 | Vidlund | |
| 2013/0231701 A1 | 9/2013 | Voss et al. | |
| 2014/0039547 A1 | 2/2014 | White | |
| 2014/0076955 A1 | 3/2014 | Lorenz | |
| 2014/0214079 A1 | 7/2014 | Ewers et al. | |
| 2014/0257359 A1 | 9/2014 | Tegels et al. | |
| 2015/0005810 A1 | 1/2015 | Center et al. | |
| 2015/0066055 A1 | 3/2015 | Sibbitt, Jr. et al. | |
| 2015/0105805 A1 | 4/2015 | Fortson | |
| 2015/0142049 A1 | 5/2015 | Delgado et al. | |
| 2015/0265350 A1 | 9/2015 | Shimizu et al. | |
| 2015/0289861 A1 | 10/2015 | MacPhee et al. | |
| 2016/0228107 A1 | 8/2016 | Madsen et al. | |
| 2016/0228109 A1 | 8/2016 | Jacobs et al. | |
| 2016/0242793 A1 | 8/2016 | Norton et al. | |
| 2017/0049426 A1 | 2/2017 | Gianotti et al. | |
| 2017/0049570 A1 | 2/2017 | O'Beirne et al. | |
| 2017/0086804 A1 | 3/2017 | Larzon et al. | |
| 2017/0086807 A1 | 3/2017 | Larzon et al. | |

(56) References Cited

U.S. PATENT DOCUMENTS

| | | | |
|---|---|---|---|
| 2017/0203082 | A1 | 7/2017 | Foy et al. |
| 2017/0325794 | A1 | 11/2017 | Willard et al. |
| 2018/0049731 | A1 | 2/2018 | Hardy et al. |
| 2019/0142402 | A1 | 5/2019 | Larzon et al. |
| 2019/0142403 | A1 | 5/2019 | Nyman et al. |
| 2019/0192326 | A1 | 6/2019 | Chen et al. |
| 2019/0240023 | A1* | 8/2019 | Spence ............... A61F 2/2466 |
| 2020/0046343 | A1 | 2/2020 | Kramer |
| 2020/0129164 | A1 | 4/2020 | Larzon et al. |
| 2020/0155817 | A1 | 5/2020 | Kassab et al. |
| 2023/0309979 | A1 | 10/2023 | Agnihotri et al. |
| 2023/0310155 | A1 | 10/2023 | Coumane |
| 2024/0138824 | A1 | 5/2024 | Hauck et al. |

FOREIGN PATENT DOCUMENTS

| | | | |
|---|---|---|---|
| EP | 2656816 | | 10/2013 |
| EP | 4169453 | A1 | 4/2023 |
| GB | 2365342 | | 2/2002 |
| JP | 2005-511130 | | 4/2005 |
| JP | 2013-226414 | | 11/2013 |
| WO | WO 96/024291 | | 8/1996 |
| WO | WO 97/03613 | | 2/1997 |
| WO | WO 10/081103 | | 7/2010 |
| WO | WO 14/169215 | | 10/2014 |
| WO | WO 17/019525 | | 2/2017 |
| WO | WO 18/195274 | | 10/2018 |
| WO | WO 19/098921 | | 5/2019 |
| WO | WO 19/098922 | | 5/2019 |
| WO | WO 19/157022 | | 8/2019 |
| WO | WO 20/081864 | | 4/2020 |
| WO | WO 20/085983 | | 4/2020 |
| WO | WO 21/102044 | | 5/2021 |
| WO | WO 23/072972 | | 5/2023 |
| WO | WO 24/092233 | | 5/2024 |

OTHER PUBLICATIONS

Non-Final Office Action Dated: Aug. 8, 2024 in U.S. Appl. No. 18/538,926, filed Dec. 13, 2023 and published as: 2024-0108321 on Apr. 4, 2024.

Bountouris et al., "Endovascular aneurysm repair with Fascia suture technique: short and mid- term results," Int Angiol, Epub Nov. 10, 2015.

Fisher, "The Fascia Suture Technique: This Late Bloomer Could Become a Winner," J. Endovasc Ther, 2012, 19:397-399.

Freitas et al., "The use of closure devices in peripheral endovascular interventions: The Leipzig real-world report," Journal of The American College of Cardiology, TCT Abstracts/Vascular Access and Intervention—Femoral (includes closure devices) Abstract TCT-842, p. B245, Saturday, Sep. 13, 2014, 5:00 PM-7:00 Pm.

Harrison et al., "Fascial Closure Following Percutaneous Endovascular Aneurysm Repair," Eur J Vasc Endovasc Surg (2011) 41, 346-349.

Larzon et al., "Editor's Choice—A Randomized Controlled Trial of the Fascia Suture Technique Compared with a Suture-mediated Closure Device for Femoral Arterial Closure after Endovascular Aortic Repair," Eur J Vasc Endovasc Surg (Feb. 2015) 49, 166-173.

Larzon et al., "Fascia Suturing of Large Access Sites After Endovascular Treatment of Aortic Aneurysms and Dissections," J Endovasc Ther, 2006, 13:152-157.

Lee et al., "Midterm outcomes of femoral arteries after percutaneous endovascular aortic repair using the Preclose technique," J Vasc Surg, 2008: 47:919-923.

Mathisen et al., "Complication Rate of the Fascia Closure Technique in Endovascular Aneurysm Repair," J Endovasc Ther 2012; 19:392-396.

Montan et al., "Short- and Midterm Results of the Fascia Suture Technique for Closure of Femoral Artery Access Sites After Endovascular Aneurysm Repair," J Endovasc Ther, 2011; 18:789-796.

Nelson, "Closure and Arterial Access Conundrums" Presentat+A25ion, Saturday Jun. 7, 2014, Society for Vascular Surgery, 2014 Vascular Annual Meeting, Boston, June 5-7.

Wanhainen, A., "Invited Commentary, Commentary on 'A Randomized Controlled Trial of the Fascia Suture Technique Compared with a Suture-mediated Closure Device for Femoral Arterial Closure After Endovascular Aortic Repair'" Eur J Vasc Endovasc Surg (Feb. 2015) 49, 174-174.

International Search Report and Written Opinion dated: Jan. 31, 2017 in International Application No. PCT/IB2016/001498 filed: Sep. 27, 2016.

Non Final Office Action dated: Dec. 15, 2016 in U.S. Appl. No. 15/291,991, filed Oct. 12, 2016, published as US-2017/0086807 on Mar. 30, 2017.

Notice of Allowance dated: May 12, 2017 in U.S. Appl. No. 15/291,991, filed Oct. 12, 2016, published as US-2017/0086807 on Mar. 30, 2017.

Notice of Allowance dated: Nov. 20, 2018 in U.S. Appl. No. 15/611,665, filed Jun. 1, 2017, published as: 2017-0265848 on Sep. 21, 2017.

Notice of Allowance dated: Sep. 19, 2018 in U.S. Appl. No. 15/611,665, filed Jun. 1, 2017, published as: 2017-0265848 on Sep. 21, 2017.

Final Office Action dated: Jan. 10, 2018 in U.S. Appl. No. 15/611,665, filed Jun. 1, 2017, published as: 2017-0265848 on Sep. 21, 2017.

Non-Final Office Action dated: Aug. 9, 2017 in U.S. Appl. No. 15/611,665, filed Jun. 1, 2017, published as: 2017-0265848 on Sep. 21, 2017.

Non-Final Office Action dated: Aug. 16, 2022 in U.S. Appl. No. 16/836,609, filed Mar. 31, 2020, published as: 2020-0245987 on Aug. 6, 2020.

Notice of Allowance dated: Mar. 24, 2023, in U.S. Appl. No. 16/836,609, filed Mar. 31, 2020, published as: 2020-0245987 on Aug. 6, 2020.

Non-Final Office Action dated: Aug. 30, 2018 in U.S. Appl. No. 15/277,542, filed Sep. 27, 2016 published as 2017-0086804 on Mar. 30, 2017.

Final Office Action dated: Apr. 24, 2019 in U.S. Appl. No. 15/277,542, filed Sep. 27, 2016 published as 2017-0086804 on Mar. 30, 2017.

Final Office Action dated: Oct. 3, 2019 in U.S. Appl. No. 15/277,542, filed: Sep. 27, 2016 published as 2017-0086804 on Mar. 30, 2017.

Notice of Allowance dated: Jan. 2, 2020 in U.S. Appl. No. 15/277,542, filed Sep. 27, 2016 published as 2017-0086804 on Mar. 30, 2017.

International Search Report and Written Opinion dated: Feb. 13, 2019 in International Application No. PCT/SE2018/051173 filed: Nov. 14, 2018.

International Search Report and Written Opinion dated: Feb. 12, 2019 in International Application No. PCT/SE2018/051172 filed: Nov. 14, 2018.

Extended European Search Report dated: May 13, 2019 in European Patent Application No. EP16850451.2 based on International Patent Application PCT/IB2016/001498 filed: Sep. 27, 2016 and published as: EP3355803 on Aug. 8, 2018.

International Search Report and Written Opinion dated: Jan. 28, 2020 in International Application No. PCT/SE2018/051041 filed: Oct. 23, 2019.

Invitation to Pay Additional Fees dated: Jan. 25, 2021 in International Application No. PCT/US2020/061117 filed: Nov. 18, 2020.

Non-Final Office Action Dated: Mar. 17, 2021 in U.S. Appl. No. 16/190,654, filed Nov. 14, 2018 and published as: 2019-0142402 on May 16, 2019.

International Preliminary Report on Patentability dated: Jun. 2, 2022 in International Application No. PCT/US2020/061117 filed: Nov. 18, 2020 and published as: WO/2021/102044 on May 27, 2021.

International Search Report and Written Opinion dated: Mar. 26, 2021 in International Application No. PCT/US2020/061117 filed: Nov. 18, 2020.

Non-Final Office Action dated: Feb. 8, 2021 in U.S. Appl. No. 16/190,694, filed Nov. 14, 2018 published as: 2019-0142403 on: May 16, 2019.

(56) References Cited

OTHER PUBLICATIONS

Final Office Action dated: Aug. 4, 2021 in U.S. Appl. No. 16/190,694, filed Nov. 14, 2018 and published as: 2019/0142403 on: May 16, 2019.

Non-Final Office Action dated: Nov. 18, 2021 in U.S. Appl. No. 16/190,694, filed Nov. 14, 2018 and published as: 2019/0142403 on: May 16, 2019.

Final Office Action dated: Mar. 1, 2022 in U.S. Appl. No. 16/190,694, filed Nov. 14, 2018 and published as: 2019/0142403 on: May 16, 2019.

Non-Office Action dated: Jul. 13, 2022 in U.S. Appl. No. 16/190,694, filed Nov. 14, 2018 and published as: 2019/0142403 on: May 16, 2019.

Final Office Action dated: Nov. 8, 2022 in U.S. Appl. No. 16/190,694, filed Nov. 14, 2018 and published as: 2019/0142403 on: May 16, 2019.

Non-Final Office Action dated: Sep. 13, 2023 in U.S. Appl. No. 16/190,694, filed Nov. 14, 2018 and published as: 2019/0142403 on: May 16, 2019.

Notice of Allowance and Corrected Notice of Allowability Dated: Aug. 30, 2021 in U.S. Appl. No. 16/190,654, filed Nov. 14, 2018 and published as: 2019-0142402 on May 16, 2019.

Final Office Action dated: Sep. 13, 2023 in U.S. Appl. No. 16/661,261, filed Oct. 23, 2019 and published as: 2020/0129164 on: Apr. 30, 2020.

Non-Final Office Action dated: Jan. 4, 2023 in U.S. Appl. No. 16/661,261, filed Oct. 23, 2019 and published as: 2020/0129164 on: Apr. 30, 2020.

Final Office Action dated: Sep. 7, 2022 in U.S. Appl. No. 16/661,261, filed Oct. 23, 2019 and published as: 2020/0129164 on: Apr. 30, 2020.

Non-Final Office Action dated: Mar. 15, 2022 in U.S. Appl. No. 16/661,261, filed Oct. 23, 2019 and published as: 2020/0129164 on: Apr. 30, 2020.

Non-Final Office Action dated: Jan. 31, 2024 in U.S. Appl. No. 16/661,261, filed Oct. 23, 2019 and published as: 2020/0129164 on: Apr. 30, 2020.

Extended European Search Report dated: Jul. 11, 2022 in European Patent Application No. EP19875930.0 filed as: PCT/SE2019/051041 on: Oct. 23, 2019.

Notice of Allowance dated: Nov. 14, 2023 in U.S. Appl. No. 16/951,886, filed Nov. 18, 2020 and published as: 2021/0145421 on May 20, 2021.

Invitation to Pay Additional Fees dated: Feb. 20, 2024 in International Application No. PCT/US2023/078087 filed: Oct. 27, 2023.

International Search Report and Written Opinion dated: Apr. 10, 2024 in International Application No. PCT/US2023/078087 filed: Oct. 27, 2023 and published as: WO/2024/092233 on May 2, 2024.

Extended European Search Report dated May 22, 2024 in European Patent Application No. 20891101.6 filed: Nov. 18, 2020.

Non-Final Office Action Dated: May 22, 2024 in U.S. Appl. No. 17/507,640, filed Oct. 21, 2021 and published as: 2022-0039781 on Feb. 10, 2022.

Notice of Allowance dated: Jun. 12, 2024 in U.S. Appl. No. 16/661,261, filed: Oct. 23, 2019 and published as: 2020/0129164 on: Apr. 30, 2020.

Non-Final Office Action dated: Jan. 20, 2026 in U.S. Appl. No. 18/496,641, field on Oct. 27, 2023 and published as: 2024-0138824 on: May 2, 2024.

* cited by examiner

FIG. 27                                    FIG. 28

VASCULAR CLOSURE DEVICES AND METHODS

RELATED APPLICATIONS

The present application is a divisional of co-pending U.S. patent application Ser. No. 16/951,886, filed Nov. 18, 2020, by Brian HAUCK et al., titled "VASCULAR CLOSURE DEVICES AND METHODS", which claims priority under 35 U.S.C. section 119(e) from U.S. Provisional Patent Application No. 62/937,675, filed Nov. 19, 2019, by Brian HAUCK et al., titled "VASCULAR CLOSURE DEVICES AND METHODS", each of which is incorporated by reference herein in its entirety.

BACKGROUND

In many percutaneous procedures, a catheter is inserted into an access hole in a blood vessel, such as the femoral artery. Such percutaneous procedures may include minimally invasive cardiovascular procedures, for example, including balloon angioplasty procedures, atherectomy procedures, cardiovascular stent deployment, heart valve replacement, as well as others. During such procedures, a therapeutic catheter may be inserted, typically over a guidewire, directly into an artery, or the catheter may be inserted through a vascular introducer sheath. When the therapeutic procedure is complete, the physician generally removes the therapeutic catheter and then removes the introducer sheath from the vessel (if one was used). The physician then must prevent or limit the amount of blood that leaks through the vascular access hole. Physicians currently use a number of methods to close the vascular access hole or otherwise limit bleeding post procedure from the access hole, such as localized external compression, suture-mediated closure devices, plugs, gels, foams and similar materials.

However, such closure procedures may be time consuming, and may consume a significant portion of the time of the procedure. In addition, existing methods are associated with complications such as hematoma or thromboses. Still further, some of such procedures, particularly suture-mediated closure devices, are known to have high failure rates in the presence of common vascular diseases such as atherosclerosis and calcification.

SUMMARY

Some embodiments of a vascular closure assembly may include an actuator assembly having an elongate housing with an inner lumen extending along the elongate housing to the distal end of the elongate housing. The elongate housing may also have a distal section, and a plurality of anchor deployer lumens. The actuator assembly may also include a plurality of anchor deployers, each anchor deployer being slidably disposed within a respective anchor deployer lumen of the elongate housing with each anchor deployer including a distal end which is configured to extend and spread distally and radially outward from the distal section of the elongate housing. The vascular closure assembly may also have an inner catheter assembly including an elongate shaft having a proximal end, a distal end, a distal section, an axial length that is sufficient for the distal section to extend distally beyond the distal end of the elongate housing when disposed in the inner lumen thereof, and an outer surface contour which is configured to be slidably disposed within the inner lumen of the elongate housing. The inner catheter assembly may further include an inflatable balloon disposed on the distal section of the elongate shaft in an axial position that can extend distally from the distal end of the elongate housing when the elongate shaft is disposed within the inner lumen of the elongate housing. The inflatable balloon may have an interior volume in communication with a balloon inflation lumen, the balloon inflation lumen extending along the elongate shaft from an inflation port which is disposed in fluid communication with the interior volume of the self-inflating balloon to an inlet port which is disposed on the elongate shaft.

Some embodiments of a vascular closure assembly may include an actuator assembly having a chassis portion with an outer shell forming an interior volume disposed within the outer shell. The actuator assembly may further include an elongate housing with a proximal end secured to a distal end of the chassis portion, a distal end extending away from the chassis portion, an inner lumen extending along the elongate housing to the distal end of the elongate housing, a distal section, and a plurality of anchor deployer lumens. In some cases, each anchor deployer lumen may extend axially along the elongate housing and terminate distally at a distal port disposed in the distal section of the elongate housing. The actuator assembly may also include a plurality of anchor deployers, each anchor deployer being slidably disposed within a respective anchor deployer lumen of the elongate housing and including a distal end which is configured to extend and spread in a distal and radially outward direction from the distal section of the outer housing. For some embodiments, each anchor deployer may include a deployment rod which has an elongate resilient configuration with an axial length greater than a transverse dimension thereof and a distal end that extends from the distal section of the elongate housing upon distal axial deployment. Each of the anchor deployers may also have an anchor which is removably secured to the distal end of the deployment rod, and which is configured to resist proximal retraction within tissue. The vascular closure assembly may also include an inner catheter assembly having an elongate shaft with a proximal end, a distal end, a distal section, an axial length that is sufficient for the distal section to extend distally beyond the distal end of the elongate housing when disposed in the inner lumen thereof, and an outer surface contour which is configured to be slidably disposed within the inner lumen of the elongate housing. The inner catheter assembly may further include an inflatable balloon disposed on the distal section of the elongate shaft in an axial position that can extend distally from the distal end of the elongate housing when the elongate shaft is disposed within the inner lumen of the elongate housing. The inflatable balloon may have an interior volume that is in fluid communication with a balloon inflation lumen.

Some embodiments of an actuator assembly may include a chassis portion having an outer shell with an interior volume disposed within the outer shell. The actuator assembly may further include an elongate housing with an axial length greater than a transverse dimension thereof, a proximal end secured to a distal end of the chassis portion, a distal end extending away from the chassis portion, and an inner lumen extending along the elongate housing to the distal end of the elongate housing. The elongate housing may also include a distal section, a filament lumen that extends along the elongate housing and terminates at a distal port disposed in the distal section of the elongate housing, and a plurality of anchor deployer lumens. In some cases, each anchor deployer lumen may extend axially along the elongate housing and terminate distally at a distal port disposed in the distal section of the elongate housing. The actuator assembly may also have a plurality of anchor deployers, each anchor deployer being slidably disposed within a respective anchor deployer lumen of the elongate housing and including a distal end which is configured to extend and spread distally and radially outward from the distal section of the elongate housing. For some embodiments, each anchor deployer may include a deployment rod which has an elongate resilient configuration with an axial length greater than a transverse dimension and a distal end that extends from the distal section of the elongate housing upon distal axial deployment. The anchor deployers may also each have an anchor which is removably secured to the distal end of the deployment rod. Each anchor deployer may also include a filament which is slidably disposed within the filament lumen of the elongate housing and which has a distal end which is secured to the anchor. The actuator assembly may also include a filament lock mechanism disposed at a distal end of the filament lumen and including a filament lock disposed in operative arrangement with the filaments of the respective plurality of anchor deployers.

Some embodiments of a catheter assembly may include an elongate shaft having a proximal end, a distal end, a distal section and a proximal chassis secured to the proximal end of the elongate shaft. The catheter assembly may also include a self-inflating balloon disposed on the distal section of the shaft, the self-inflating balloon having a thin compliant shell material, an interior volume in communication with a balloon inflation lumen, the balloon inflation lumen extending along the elongate shaft from an inflation port which is disposed in fluid communication with the interior volume of the self-inflating balloon to an inlet port which is disposed on the elongate shaft at an axial position which is distal of a distal end of the self-inflating balloon. In addition, the catheter assembly may include a balloon inflation valve configured to controllably open and close the balloon inflation lumen.

Some embodiments of a filament lock may include a tubular structure with a main body portion and a plurality of fingers extending proximally from the main body portion. In some cases, the fingers may be of sufficient axial length and elastically biased towards a center longitudinal axis of the main body portion such that respective distal ends of the fingers are configured to be self-contracting from an expanded state to a relaxed state and clamp onto the filaments disposed within the inner lumen of the filament lock when the fingers are in the relaxed state. In addition, the fingers may be configured to be elastically spread to a relative transverse separation to the expanded state sufficient to fit onto an outer surface of a distal end of a filament tube.

Some embodiments of a method for vascular closure may include distally advancing a vascular closure assembly towards an access hole in a blood vessel and a passage disposed in a tissue layer adjacent the blood vessel. In some cases, the vascular closure assembly may be so advanced while an inner catheter assembly of the vascular closure assembly is disposed within an inner lumen of an elongate housing of an actuator assembly of the vascular closure assembly. In addition, the vascular closure assembly may be so distally advanced with an inflatable balloon of the inner catheter assembly extending distally beyond the distal end of the elongate housing. The method may also include inflating the inflatable balloon until contact and hemostasis is established between an outer surface of the self-inflating balloon and a perimeter surface of the access hole in the blood vessel. The method may further include axially translating the actuator assembly over the inner catheter assembly while holding the inner catheter assembly in a fixed axial position relative to the access hole in the blood vessel until a distal end of an elongate housing of the actuator assembly is disposed adjacent the passage in the tissue layer. Thereafter, a plurality of anchor deployers may be deployed so as to extend in a distal and radially outward direction away from a distal section of the elongate housing of the vascular closure assembly with an anchor deployer actuator. The anchor deployers may further engage the tissue layer in positions disposed about the passage in the tissue layer with respective anchors of the plurality of anchor deployers. The method may also include drawing the anchors closer together by applying proximal tension to the filaments secured to each of the anchors so as to draw the anchors and respective portions of the tissue layer secured to each of the anchors together and thereby reduce the transverse dimension of the passage in the tissue layer. For some embodiments, a filament lock may be deployed onto the filaments at the distal end of the elongate housing by activating the filament lock mechanism while maintaining tension force on the filaments with a tensioning spring.

Some embodiments of a vascular closure device may include a filament lock having a tubular structure with a main body portion and a plurality of fingers extending proximally from the main body portion. In some cases, the fingers may be of sufficient axial length and elastically biased towards a center longitudinal axis of the main body portion such that respective distal ends of the fingers are configured to be self-contracting from an expanded state to a relaxed state and clamp onto the filaments disposed within the inner lumen of the filament lock when the fingers are in the relaxed state. In addition, the fingers may be elastically spread in an outward radial direction to a relative transverse separation to the expanded state sufficient to fit onto an outer surface of a distal end of a filament tube. The vascular closure assembly may further include the filament tube disposed within the inner lumen of the filament lock with the filament lock in the expanded state and at least one filament disposed within the inner lumen of the filament lock. The vascular closure assembly may also have a filament tube actuator which is configured to axially withdraw the filament tube from within the inner lumen of the filament lock.

Some embodiments of a method for vascular closure may include distally advancing an actuator assembly until a distal end of an elongate housing of the actuator assembly is disposed adjacent a passage in a tissue layer. The method may further include deploying a plurality of anchor deployers from the elongate housing in a distal and radially outward direction in an asymmetric pattern about a longitudinal axis of the elongate housing and engaging the tissue layer in positions disposed about the passage in the tissue layer in an asymmetric deployment pattern with respective anchors of the plurality of anchor deployers. The anchors may then be drawn closer together by applying tension to filaments secured to each of the respective anchors so as to draw the anchors and respective portions of the tissue layer secured to each of the anchors together and thereby reducing a transverse dimension of the passage in the tissue layer and then deploying a filament lock onto the filaments at a distal end of the elongate housing while maintaining tension force on the filaments.

Certain embodiments are described further in the following description, examples, claims and drawings. These features of embodiments will become more apparent from the following detailed description when taken in conjunction with the accompanying exemplary drawings.

BRIEF DESCRIPTION OF THE DRAWINGS

FIG. 27 is a transverse section view of the filament lock embodiment of FIG. 25 taken along lines 27-27 of FIG. 25.

FIG. 28 shows the filament lock embodiment of FIG. 27 in an enlarged expanded state.

Figure 1:
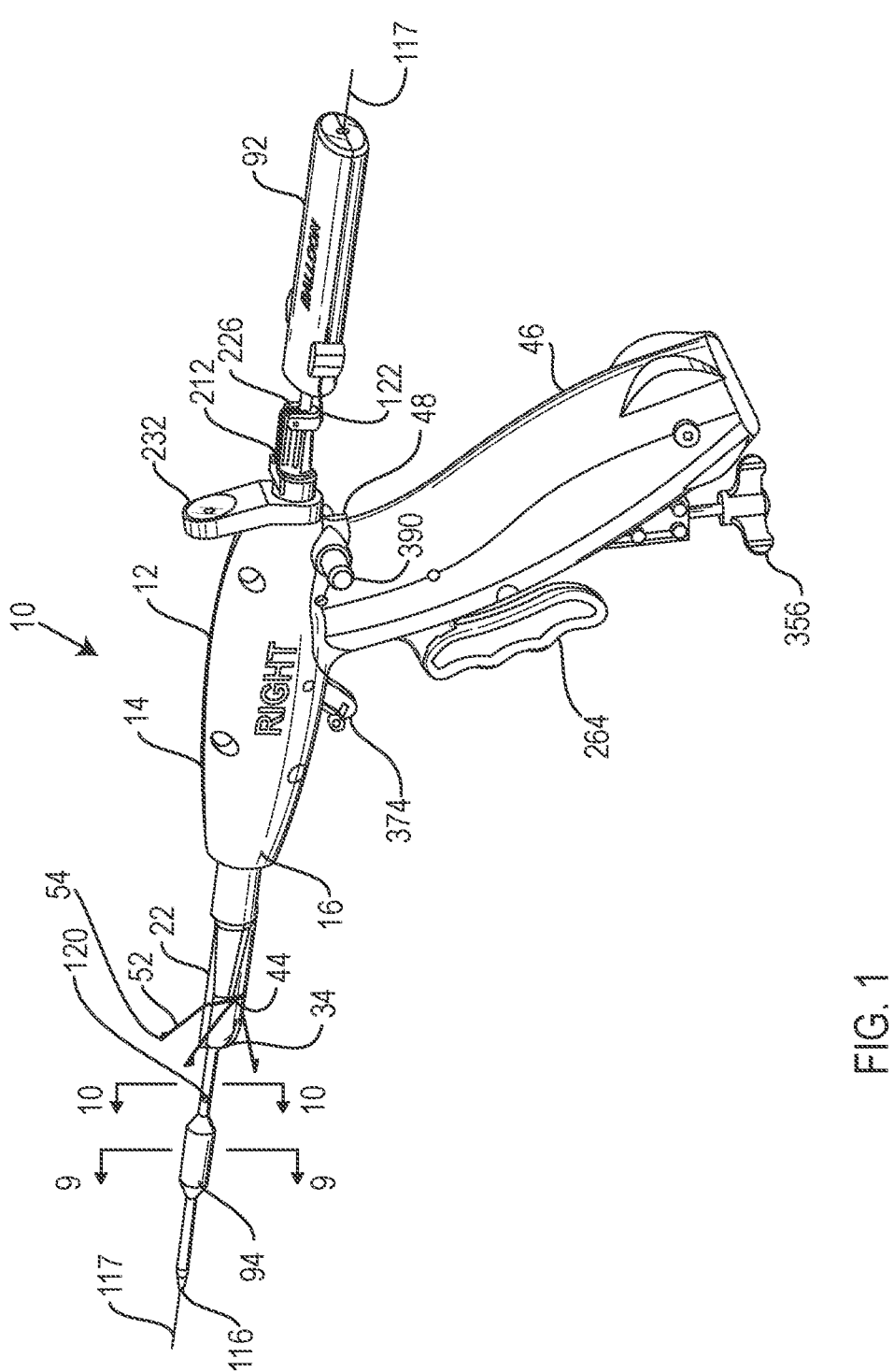
FIG. 1 is a perspective view of a vascular closure assembly embodiment that includes an actuator assembly and an inner catheter assembly.

The drawings are intended to illustrate certain exemplary embodiments and are not limiting. For clarity and ease of illustration, the drawings may not be made to scale, and in some instances, various aspects may be shown exaggerated or enlarged to facilitate an understanding of particular embodiments.

DETAILED DESCRIPTION

As discussed above, after a percutaneous catheterization procedure or any other procedure that requires vascular access with an access hole in a blood vessel of a patient, the physician must typically address the issue of bleeding from the vascular access hole once the therapeutic or diagnostic device or devices have been removed from the access hole in the patient's blood vessel. Some suitable device and method embodiments for such procedures are discussed in U.S. patent application Ser. No. 15/277,542, now U.S. Pat. No. 10,639,020, filed Sep. 27, 2016 and issued May 5, 2020, by Thomas Larzon, et al., entitled VASCULAR CLOSURE DEVICE, U.S. patent application Ser. No. 16/190,654, filed Nov. 14, 2018, by Thomas Larzon, et al., entitled COLLAPSIBLE TUBE FOR HEMOSTASIS, and U.S. patent application Ser. No. 16/190,694, filed Nov. 14, 2018, by Henrik Nyman, et al., entitled TISSUE CLOSURE DEVICE, each of which is incorporated by reference herein in its entirety. Any of the features, dimensions or materials of the embodiments discussed in these incorporated references may be combined with or substituted for any suitable features, dimensions or materials of the device and method embodiments discussed herein. In addition, the embodiments discussed herein may be used or combined with each other in any suitable manner. In particular, any of the features, dimensions or materials of any of the embodiments discussed herein may be combined with or substituted for any of the features, dimensions or materials of any other suitable embodiment discussed herein.

Some embodiments of vascular closure assemblies discussed herein may be useful for addressing certain clinical issues that may arise during use of a vascular closure device, such as rapid deployment, convenience, ease of use, and the like. Some of the device embodiments may include two primary components directed to an actuator assembly (that may optionally include a handle portion) and an inner catheter assembly. The inner catheter assembly may include a small blood return lumen to provide an indication that the distal tip is in fluid communication with an interior lumen of a blood vessel, a foot extension for positioning against the anterior wall of a blood vessel and an inflatable balloon for maintaining hemostasis during a vascular closure procedure. Although the inner catheter assembly is frequently discussed herein as a component of a vascular closure assembly, in some cases, such inner catheter assembly embodiments may function as stand alone catheter assemblies having the same or similar features, dimensions and materials. The actuator embodiment may include a plurality of anchor deployers and associated anchors, including four or more such anchor deployers and associated anchors, or any other suitable number of anchor deployers, with filaments such as sutures each having distal end secured to one of the plurality of anchors. The anchors may be implanted and/or engaged in a tissue layer at locations circumferentially disposed about an access hole in a blood vessel by deployment rods actuated by an actuator lever on the actuator assembly. The actuator assembly may also include a spring for applying tension force to the filaments to close the access hole, and a filament lock to hold the filaments in place once the connection to the actuator assembly is cut.

In general, during use of such embodiments, the operation of device embodiments to close an access hole may begin once the underlying therapeutic or diagnostic procedure is complete and generally while the guidewire used for the procedure is still in place. The actuator assembly together with the inner catheter assembly may be first loaded over the guidewire, and then advanced into the access hole (while hemostasis is maintained via manual compression) until a visible blood return appears on the proximal end of the blood return lumen of the inner catheter assembly. A lever may then be activated to deploy the foot extension, and the actuator assembly and inner catheter assembly are pulled proximal until the foot extension engages with the anterior wall of the blood vessel. Next, another lever may be actuated to open a balloon inflation valve to allow blood pressure to fill the inflatable hemostasis balloon, thereby providing temporary blood leakage control or hemostasis control at the access site. Manual compression may then be reduced or released.

The actuator assembly may then be slid distally over the inner catheter assembly until it is aligned with an insertion alignment mark, thereby positioning the nose tip of the actuator assembly the correct distance from the blood vessel and the tissue layer disposed above the blood vessel, for example the fascia layer. An actuator lever on the actuator assembly may be pulled next to deploy the anchor deployers and associated anchors. Filament tension may then be applied by rotating the large knob at the base of the actuator assembly. The inflatable balloon may then be withdrawn, allowing filament tension to fully close the access hole. Finally, the filament lock may be deployed by pulling a small lever on the actuator assembly, and the suture filaments are cut by pressing a filament cutter button on the proximal aspect of the actuator assembly. The device may now be slid off the guidewire and skin wound closed in standard fashion.

Figure 2:
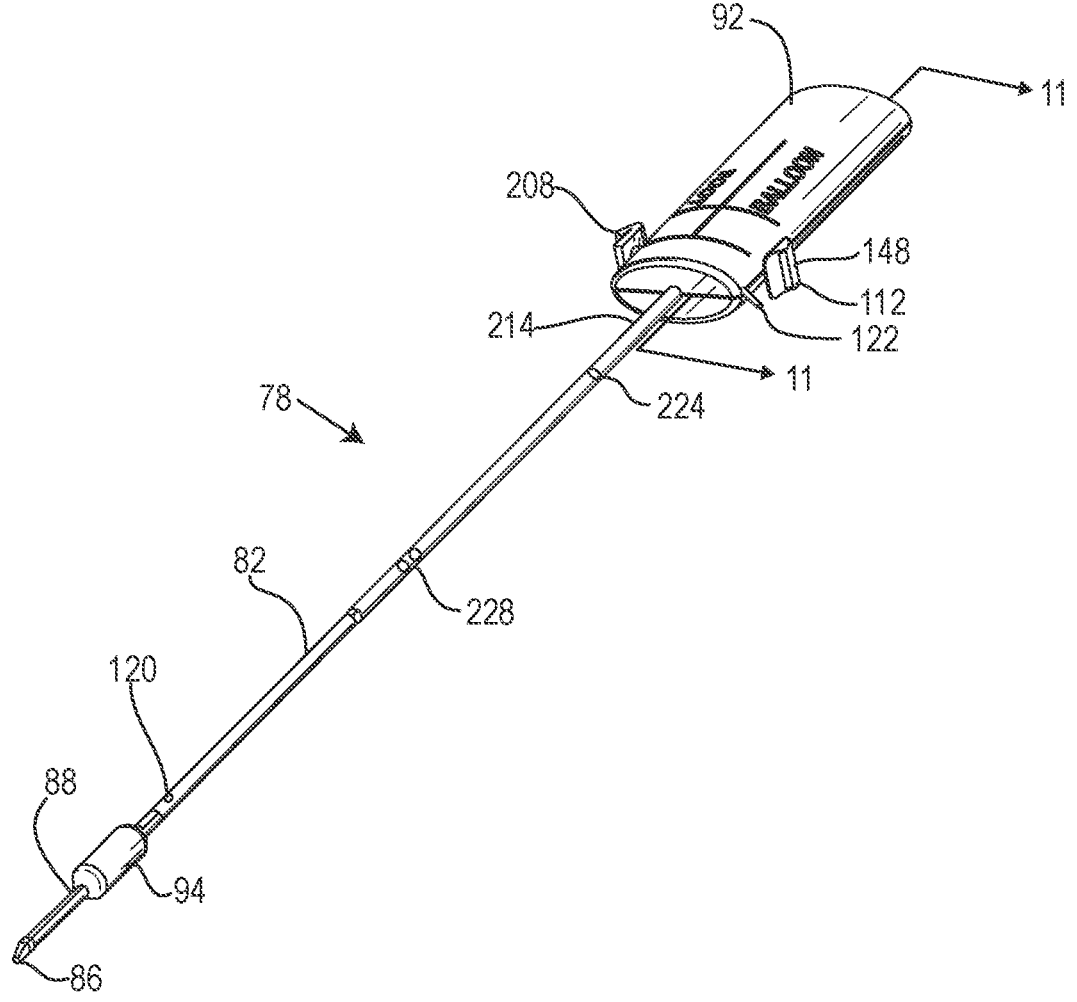
FIG. 2 is a perspective view of an inner catheter assembly embodiment of the vascular closure assembly of FIG. 1.
Figure 3:
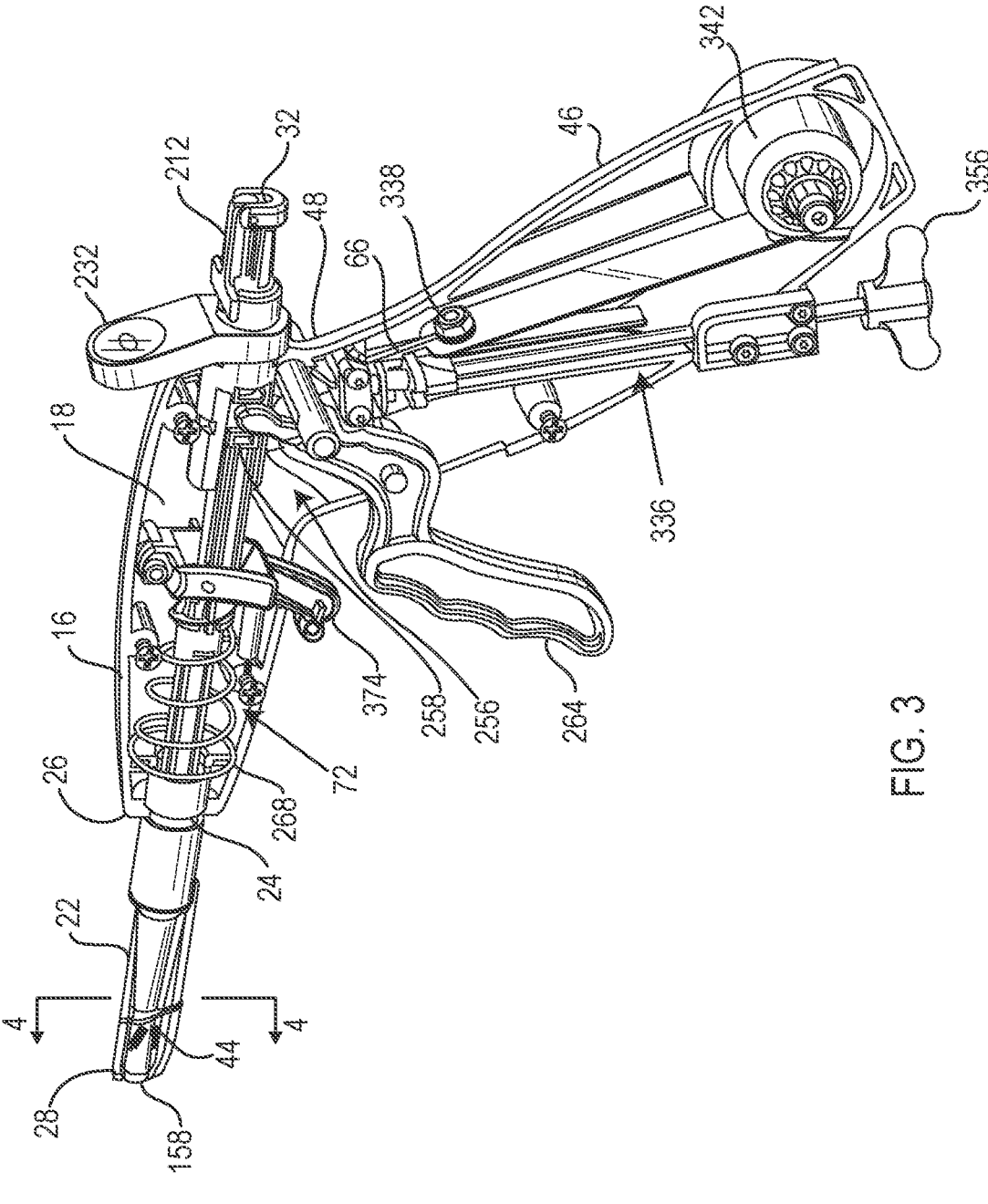
FIG. 3 is a cut away view of an actuator assembly embodiment of the vascular closure assembly of FIG. 1.
Figure 4:
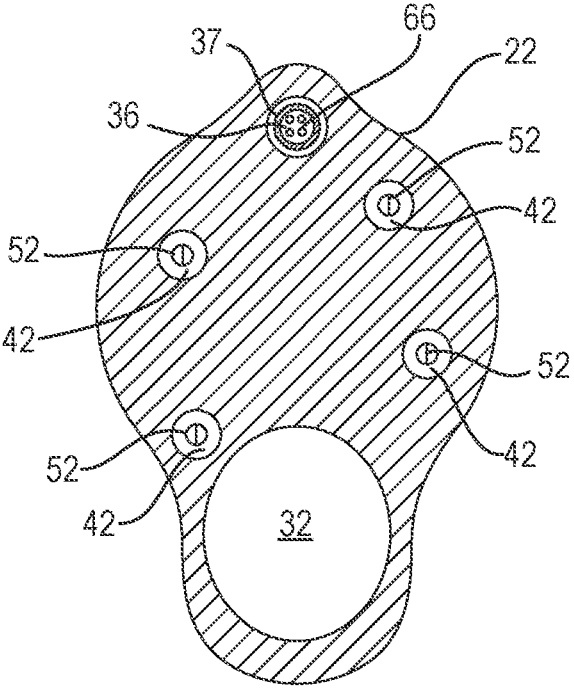
FIG. 4 is a transverse section view of the actuator assembly of FIG. 3 taken along lines 4-4 of FIG. 3.
Figure 19:
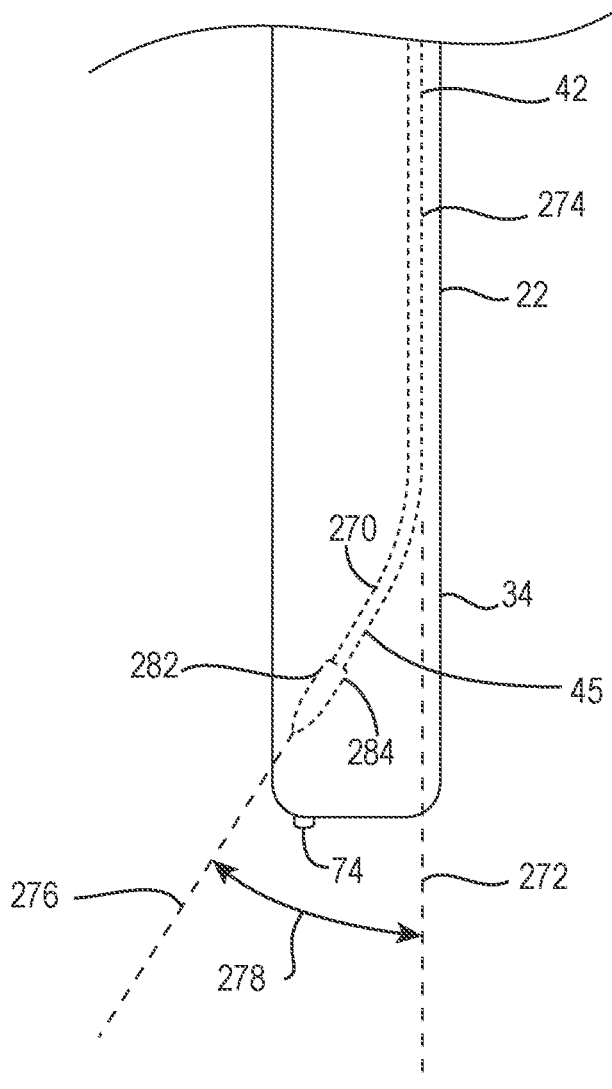
FIG. 19 shows a distal section of the elongate housing of the actuator assembly of FIG. 1 illustrating the discharge axis angle of one of the anchor deployer lumens of the actuator assembly.
Figure 20:
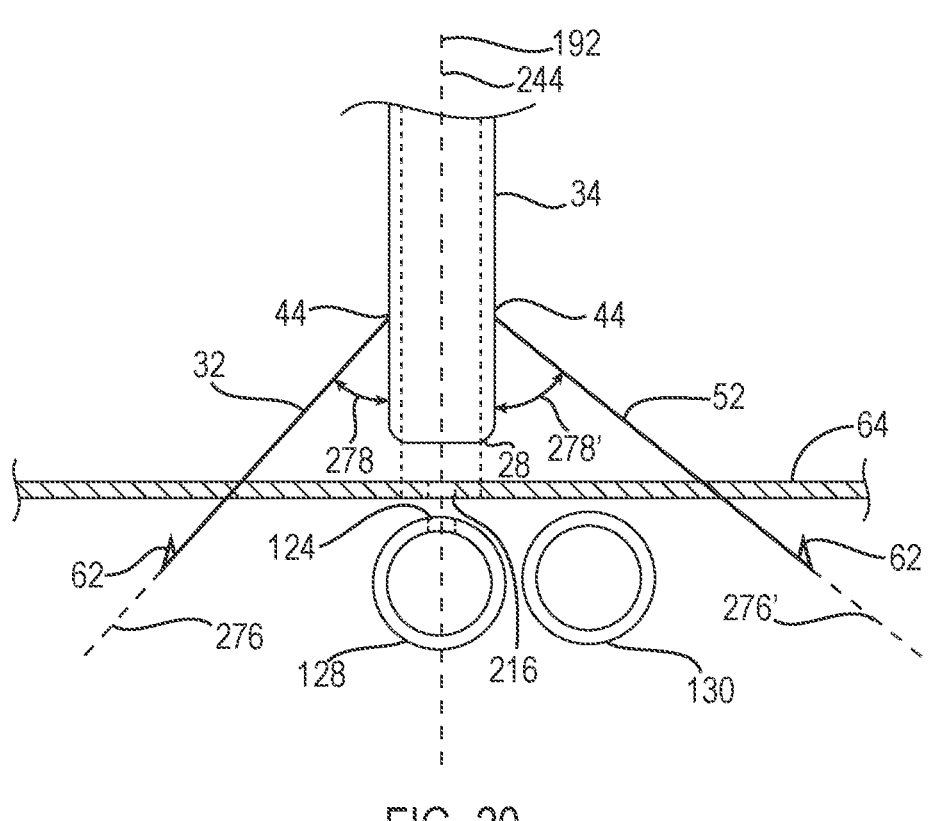
FIG. 20 is an elevation view in section of a tissue layer disposed over two blood vessels of a patient including an artery and a vein and a distal section of an elongate housing embodiment of an actuator assembly disposed adjacent the tissue layer with the anchor deployers of the actuator assembly in a deployed state and engaged with the tissue layer.
Figure 21:
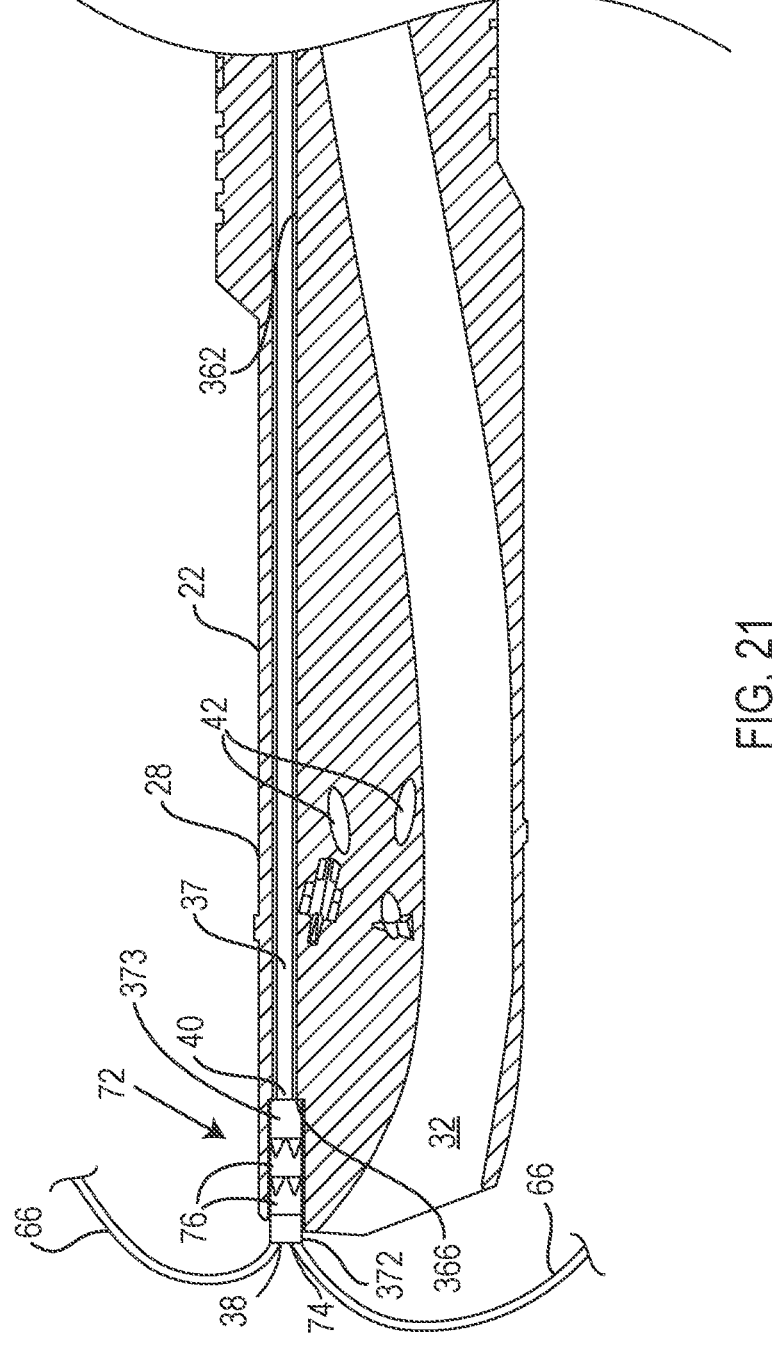
FIG. 21 is an elevation view in longitudinal section of the distal section of the elongate housing of the actuator assembly of FIG. 1.

Referring generally to FIGS. 1-6, an embodiment of a vascular closure assembly 10 that may be used for such a vascular closure procedure may include an actuator assembly 12 having a chassis portion 14 with an outer shell 16 and an interior volume 18 disposed within the outer shell 16. The actuator assembly 12 may further include an elongate housing 22 having an axial length greater than a transverse dimension thereof, a proximal end 24 secured to a distal end 26 of the chassis portion 14, and a distal end 28 extending away from the chassis portion 14. The elongate housing 22 also includes an inner lumen 32 extending along the elongate housing 22 to the distal end 28 of the elongate housing 22 as shown in FIG. 4, a distal section 34, a filament lumen 36 disposed within a filament tube 37 that extends along the elongate housing 22 as shown in FIG. 4 and that terminates at a distal port 38 disposed in the distal section 34 of the elongate housing 22 as shown in FIG. 19-21. The elongate housing 22 further includes and a plurality of anchor deployer lumens 42. Each anchor deployer lumen 42 may extend axially, along a curved or straight path, along the elongate housing 22 and terminate distally at a distal port 44 disposed in the distal section 34 of the elongate housing 22. In some cases, a handle portion 46 of the actuator assembly 12 may have an upper end 48 secured to the chassis portion 14.

Figure 29:
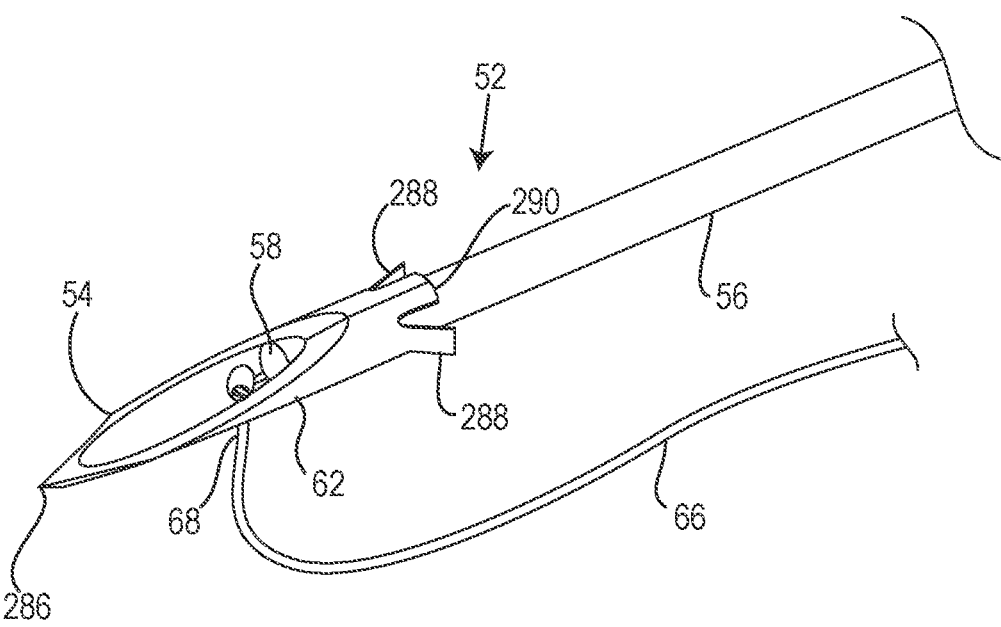
FIG. 29 is a perspective view of a distal section of an anchor deployer embodiment.
Figure 46:
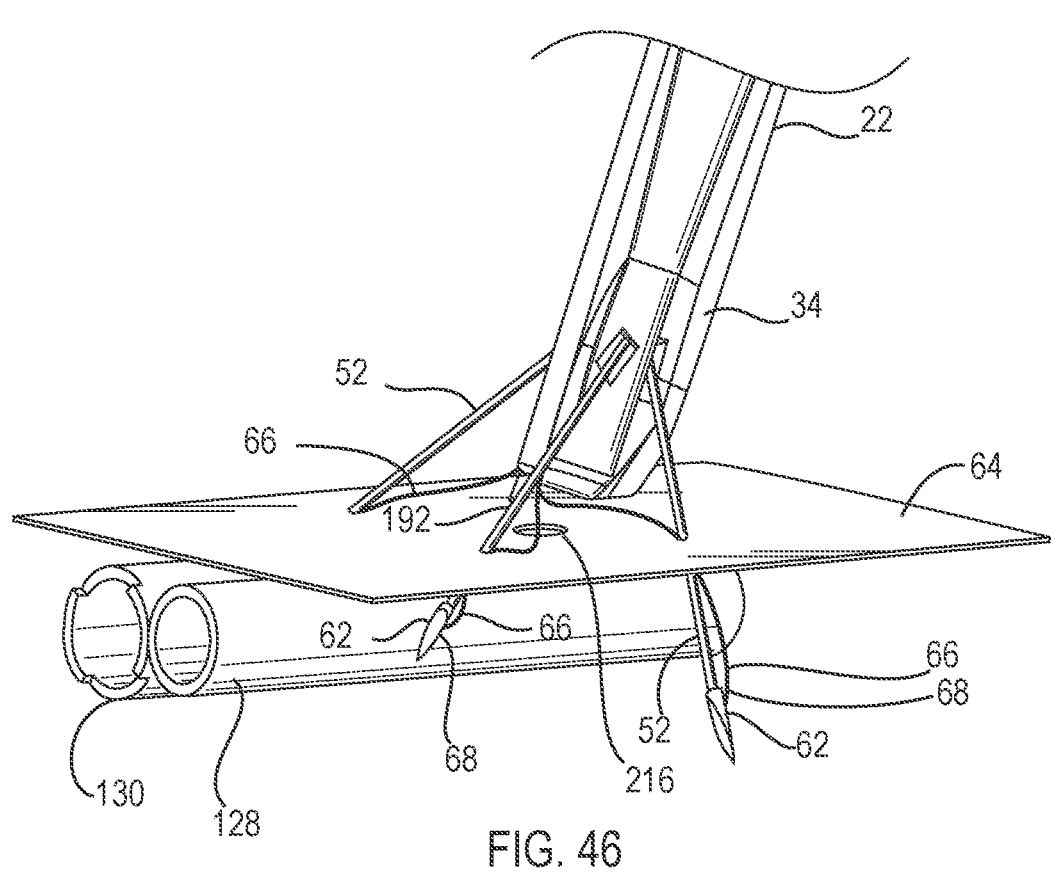
FIG. 46 is a perspective view of a distal section of the elongate housing of the actuator assembly of FIG. 1 with anchor deployers thereof deployed into the tissue layer disposed above blood vessels of the patient.
Figure 47:
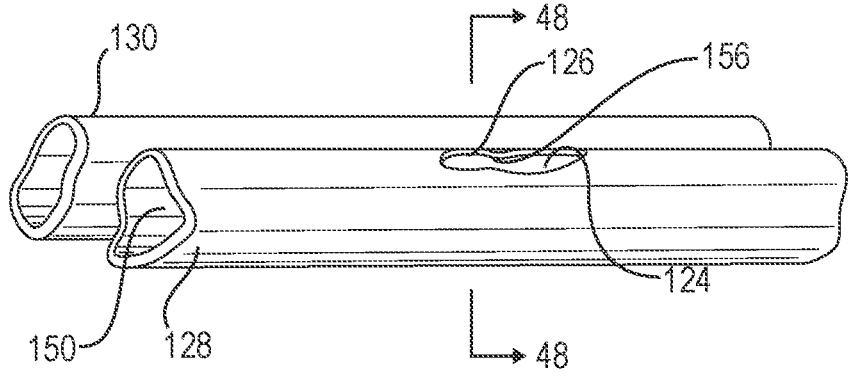
FIG. 47 is a perspective cut away view of embodiments of a patient's blood vessels including a section of an artery and a section of a vein.
Figure 48:
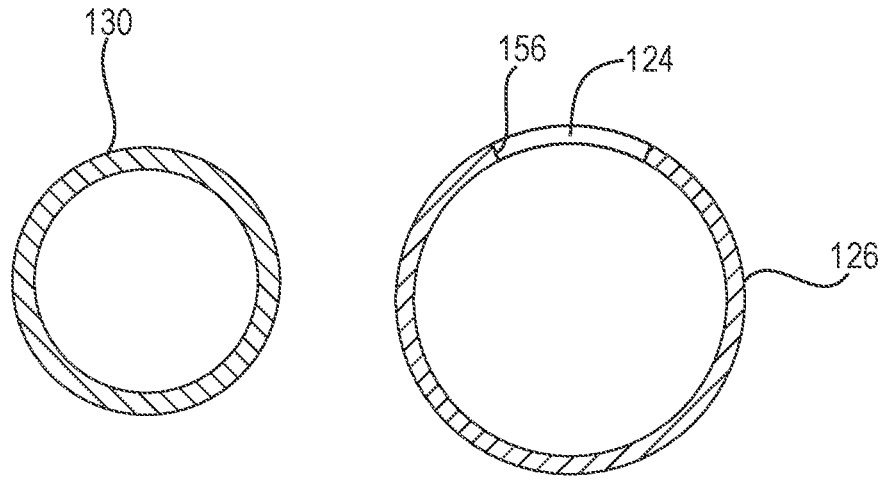
FIG. 48 is a transverse section view of the patient's blood vessels of FIG. 47 taken along lines 48-48 of FIG. 47.

The actuator assembly 12 may also include a plurality of anchor deployers 52 as shown in FIG. 4, each anchor deployer being slidably disposed within a respective anchor deployer lumen 42 of the elongate housing 22 and including a distal end 54 which is configured to extend and spread from the distal section 34 of the elongate housing 22 in a distal and radially outward orientation as shown in FIG. 29. For some embodiments, each anchor deployer 52 may include a deployment rod 56 which has an elongate resilient configuration with an axial length greater than a transverse dimension and a distal end 58 that extends from the distal section 34 of the elongate housing 22 upon distal axial deployment. An anchor 62 is removably or otherwise releasably secured to the distal end 58 of the deployment rod 56. In some cases, a tubular structure at the proximal end of the anchor embodiments 62 may be configured to slide over and mate with the distal end 58 of the deployment rod 56 such that distally oriented force from the distal end 58 of the deployment rod 56 is readily transferred to the anchor 62. However, the anchor 62 may also be configured to resist proximal retraction within tissue 64 once deployed as shown in FIG. 46 such that the distal end 58 of the deployment rod 56 slips out of the tubular structure at the proximal end of the anchor embodiments 62 upon proximal retraction of the deployment rod 56 once the anchor 62 is deployed in the tissue layer 64. A filament 66 may be slidably disposed within the filament lumen 36 of the elongate housing 22 and include a distal end 68 which is secured to the anchor 62. In addition, the actuator assembly 12 may include a filament lock mechanism 72 disposed at a distal end 74 of the filament lumen 36 and filament tube 37, the filament lock mechanism 72 including a filament lock 76 disposed in operative arrangement with the filaments 66 of the respective plurality of anchor deployers 52 as shown in FIG. 21.

Figure 9:
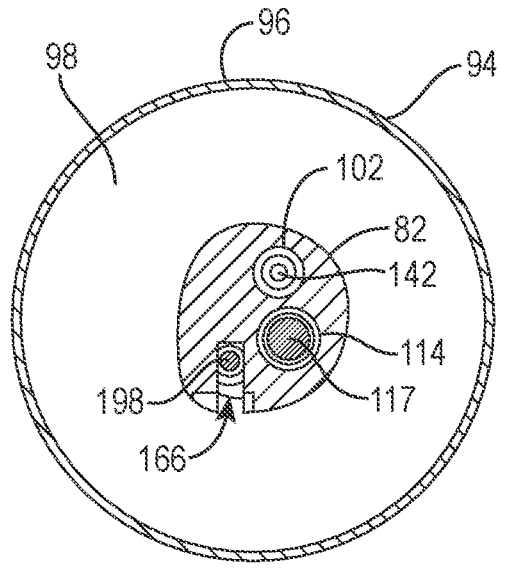
FIG. 9 is a transverse section view of the inner catheter assembly of FIG. 1 taken along lines 9-9 of FIG. 1.
Figure 10:
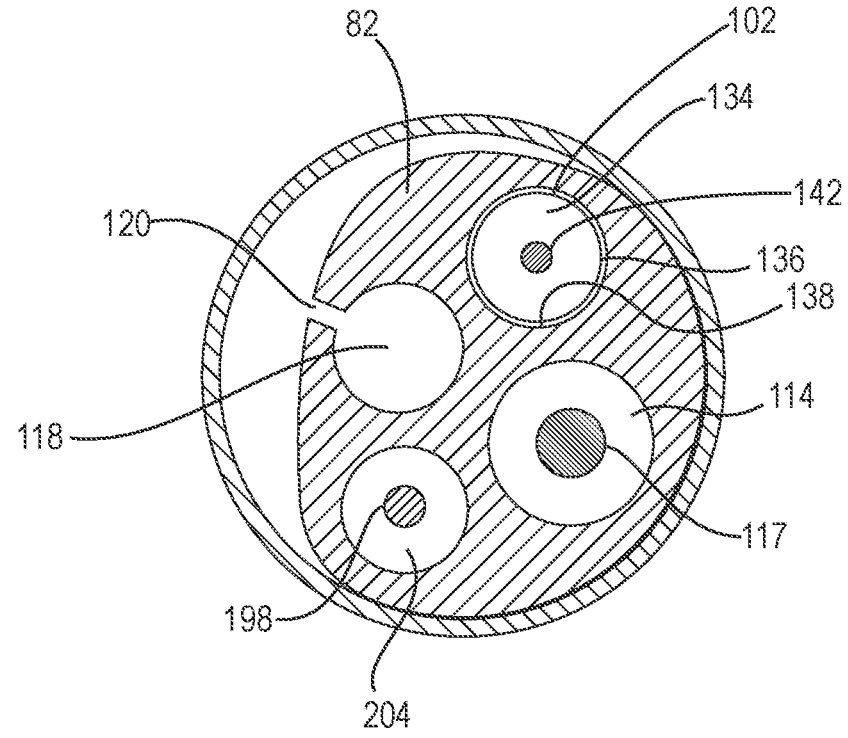
FIG. 10 is a transverse section view of the inner catheter assembly of FIG. 1 taken along lines 10-10 of FIG. 1.

Some embodiments of the vascular closure assembly may also include an inner catheter assembly 78. The inner catheter assembly 78 may have an elongate shaft 82 including a proximal end 84, a distal end 86, a distal section 88, an axial length that is sufficient for the distal section 88 to extend distally beyond the distal end 28 of the elongate housing 22 when disposed in the inner lumen 32 thereof. The inner catheter assembly 78 may further include an outer surface contour which is configured to be slidably disposed within the inner lumen 32 of the elongate housing 22. A proximal chassis 92 may be secured to the proximal end 84 of the elongate shaft 82 of the inner catheter assembly 78. An inflatable balloon that may optionally be configured as a self-inflating balloon 94 may be disposed on the distal section 88 of the elongate shaft 82 in an axial position that can extend distally from the distal end 28 of the elongate housing 22 when the elongate shaft 82 is disposed within the inner lumen 32 of the elongate housing 22. The self-inflating balloon 94 may include a wall portion 96 made from a thin compliant material and an interior volume 98 in communication with a balloon inflation lumen 102 as shown in FIGS. 9 and 10. The self-inflating balloon 94 may also have an outer surface contour that is configured to be slidably disposed within the inner lumen 32 of the elongate housing 22 when the self-inflating balloon 94 is in a deflated state.

Figure 35:
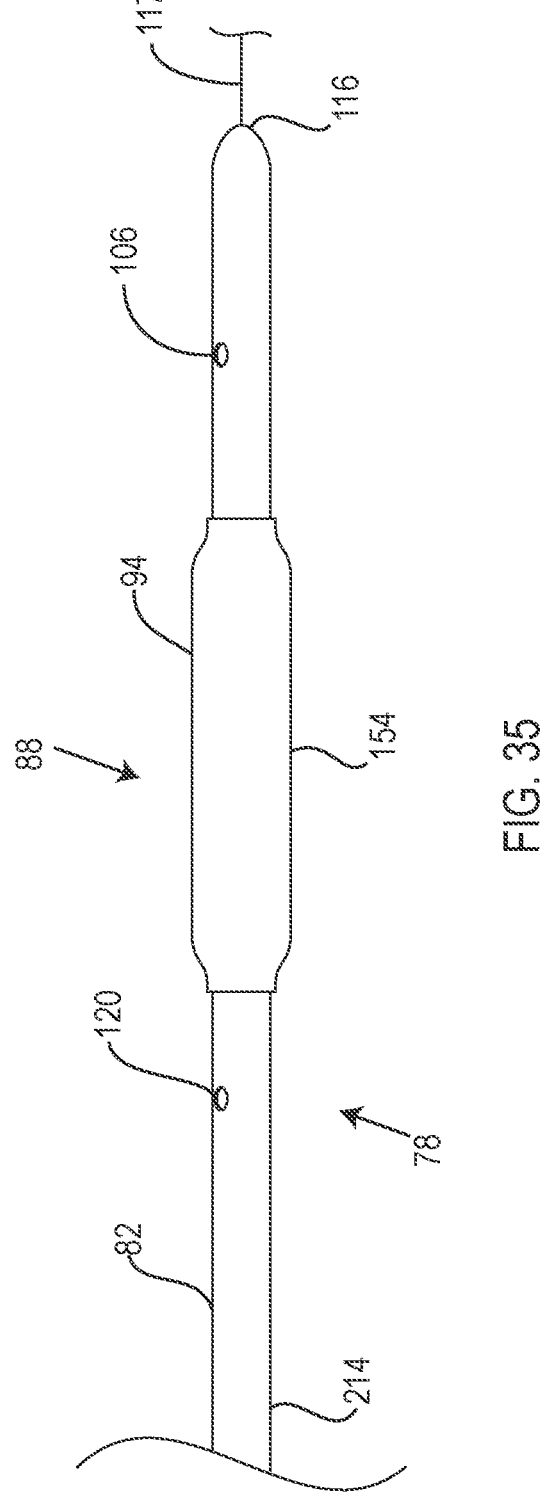
FIG. 35 is an elevation view of a distal section of an inner catheter assembly embodiment.
Figure 36:
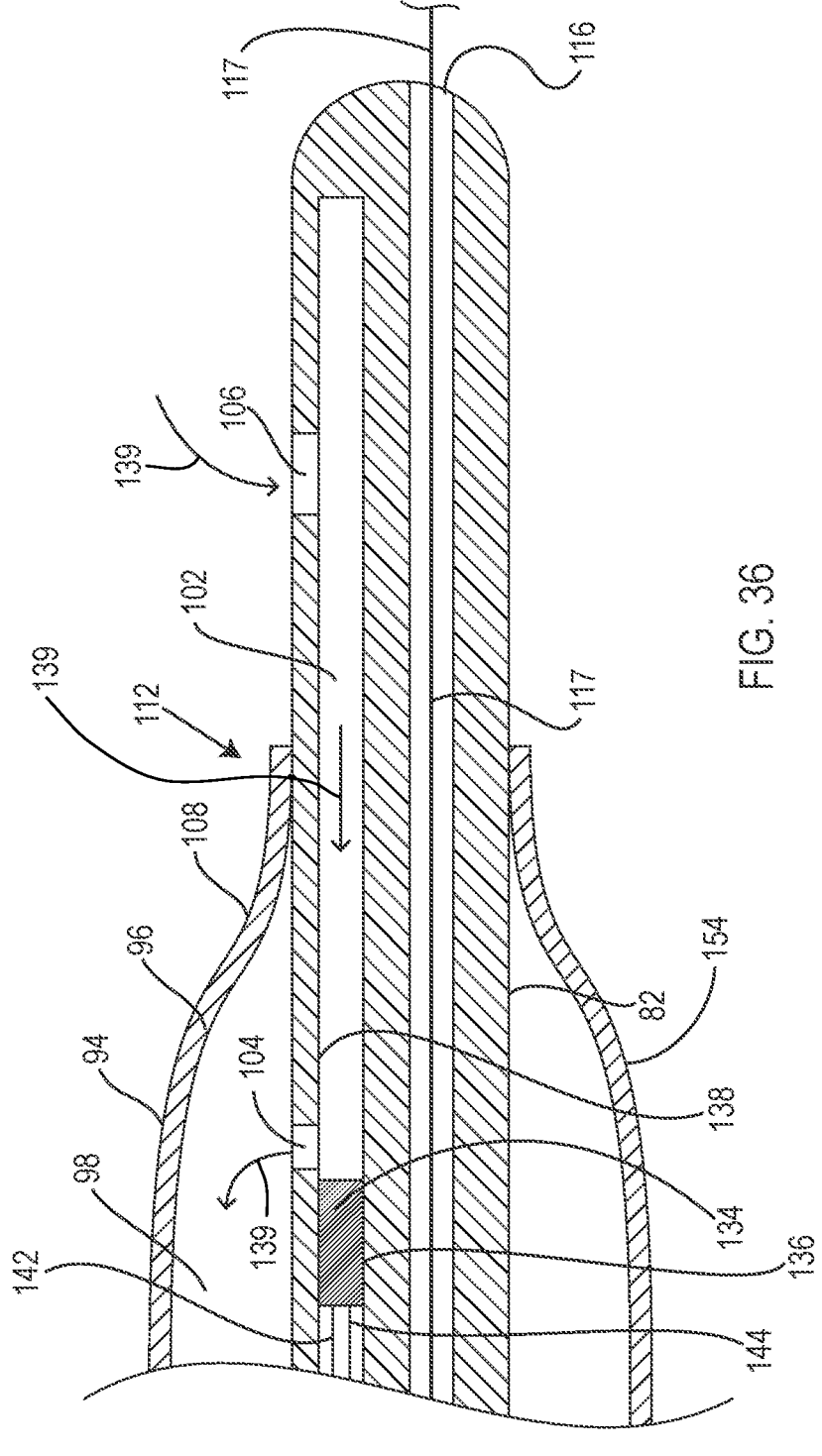
FIG. 36 is an enlarged view in longitudinal section of a distal portion an embodiment of an inner catheter assembly shown with the balloon inflation lumen in an opened state for self inflation of the self-inflating balloon.

The balloon inflation lumen 102 may extend along the elongate shaft 82 from an inflation port 104 which is disposed within and in fluid communication with the interior volume 98 of the self-inflating balloon 94 to an inlet port 106 which is disposed on the elongate shaft 82 at an axial position which is distal of a distal end 108 of the self-inflating balloon 94 as shown in FIGS. 35 and 36. Such an inner catheter assembly embodiment 78 may also have a balloon inflation valve 112 which is configured to controllably open and close the balloon inflation lumen 102. As discussed above, although the inner catheter assembly embodiments 78 discussed herein are generally referred to as components of vascular closure assembly embodiments 10, the inner catheter assembly embodiments 78 discussed herein may also function and be used as stand alone catheter assembly embodiments 78 having the same or similar features, dimensions and materials. Such stand alone catheter assembly embodiments may be used for a variety of suitable indications, including providing hemostasis during procedures other than vascular closure procedures such as coronary artery bypass graft procedures as well as others.

The inner catheter assembly 78 of the vascular closure assembly 10 may further include a guidewire lumen 114 as shown in FIGS. 9 and 10, the guidewire lumen 114 extending along the elongate shaft 82 to a distal guidewire port 116 disposed at the distal end 86 of the elongate shaft 82 to accommodate a guidewire 117 as shown in FIGS. 35 and 36. The inner catheter assembly 78 may further include a blood return lumen 118 as shown in FIGS. 9 and 10. The blood return lumen 118 may extend proximally from a distal port 120 disposed on the distal section 88 of the elongate shaft 82 to a proximal port 122 of the blood return lumen 118 disposed on the proximal chassis 92 as shown in FIG. 2. The distal port 120 may be disposed on the distal section 88 of the elongate shaft 82 in an axial position that is proximal of the self-inflating balloon 94 as also shown in FIG. 2. For embodiments of the inflatable balloon 94 that are not configured as self-inflating, the balloon inflation lumen may be disposed in fluid communication with an inflation pressure source (not shown) such as a syringe or other inflation pump rather than the inlet port 106.

For some embodiments, the self-inflating balloon 94 may have an outer profile that is configured to self-expand from a compressed state which is sized in transverse dimension to fit within the inner lumen 32 of the elongate housing 22, to an inflated state with an outer transverse dimension which is larger than an outer transverse dimension of the elongate shaft 82. The self-inflating balloon 94 in an inflated state may also be sized in transverse dimension and configured to completely fill and plug an access hole 124 disposed in a wall portion 126 of a blood vessel 128 of a patient. The self-inflating balloon 94 may further include an outer contour in the inflated state having an elongate shape or contour with a nominal axial length of the self-inflating balloon 94 being greater than a transverse dimension of the self-inflating balloon 94 when in the inflated state. In some cases, the self-inflating balloon 94 in an inflated state may have an outer transverse dimension of about 8 mm to about 15 mm and a nominal axial length of about 10 mm to about 25 mm. In some instances, the wall portion 96 of the self-inflating balloon 94 may have a thickness of about 0.02 mm to about 0.06 mm and may be made from one or more materials including urethane, polyurethane, and silicone.

Figure 11:
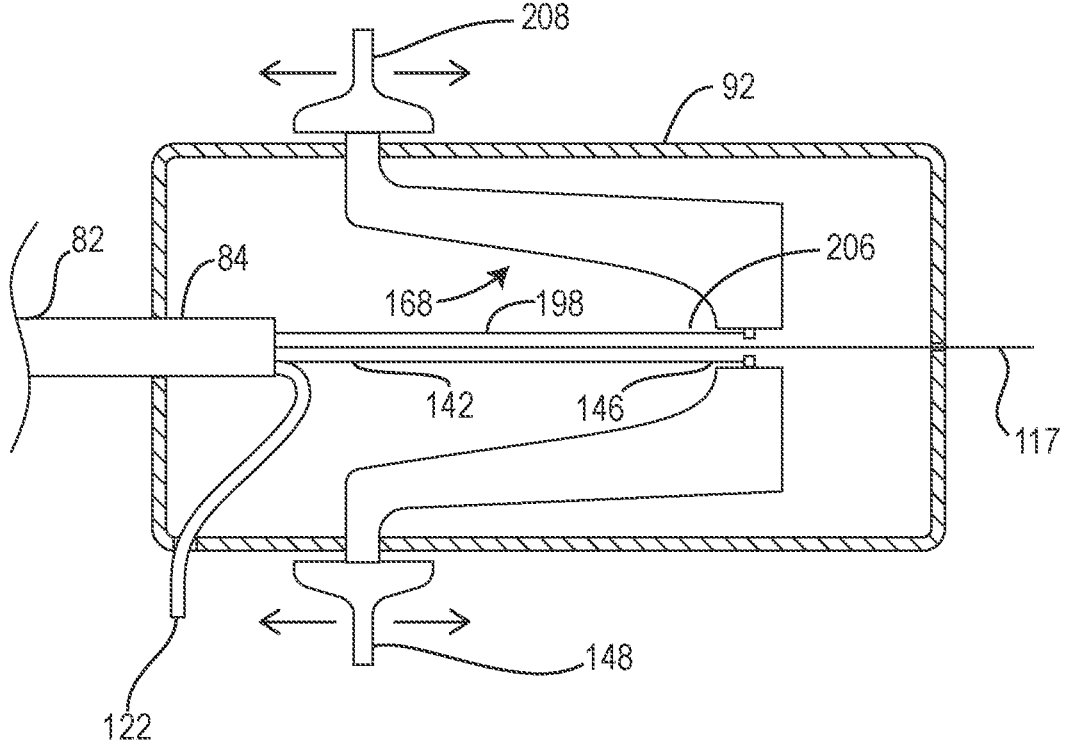
FIG. 11 is a view in longitudinal section of the proximal chassis of the inner catheter assembly of FIG. 2 taken along lines 11-11 of FIG. 2.

In some instances, it may be desirable to control inflation of the self-inflating balloon 94. As such, the balloon inflation valve 112 may be configured to reversibly open and close the balloon inflation lumen 102 as well as control the rate of flow of blood therethrough. Some embodiments of the balloon inflation valve 112 may include a plug 134 which has an outer surface contour 136 that is matched to an inner surface contour 138 of the balloon inflation lumen 102 so as to prevent a flow of fluid, such as blood, therethrough as shown in FIGS. 9, 10, 36 and 37. This configuration also permits the plug 134 to be slidably disposed within the balloon inflation lumen 102 between axial positions that block off a flow of blood from the inlet port 106 to the inflation port 104 as well as axial positions that allow a flow of blood through the balloon inflation lumen 102. An actuator rod 142 may have a distal end 144 secured to the plug 134 and a proximal end 146 operatively coupled or otherwise secured to a balloon inflation lever 148 on the proximal chassis 92 as shown in FIG. 11. The balloon inflation lever 148 may be slidable from a first position wherein the plug 134 is disposed distal of the inflation port 104 of the balloon inflation lumen 102 thereby blocking fluid communication between the inlet portion 106 and inflation port 104 of the balloon inflation lumen 102. The balloon inflation lever 148 may also be slidable to a second position, the second position being proximal of the first position and proximal of the inflation port 104 so as to allow fluid communication between the inlet port 106 and inflation port 104 through the balloon inflation lumen 102. For some embodiments, the inlet port 106 may be disposed on the elongate shaft 82 distal of the distal end 108 of the self-inflating balloon 94.

In some cases during deployment of the self-inflating balloon 94, the self-inflating balloon 94 may be filled by fluid such as blood from within the interior 150 of the blood vessel 128 and expand considerably and assume a mushroom shaped configuration with the expanded head of the mushroom configuration of the self-inflating balloon 94 being disposed outside of the blood vessel 128 adjacent the access hole 124 in the blood vessel 128. Such an expansion of the outer surface 154 of the self-inflating balloon 94 may increase friction between a perimeter surface 156 of the access hole 124 in the blood vessel 128 and the outer surface 154 of the self-inflating balloon 94. In some instances, this increased friction may in turn hinder axial movement of the self-inflating balloon 94 with respect the access hole 124 as well as other structures such as moving the inner catheter assembly 78 within the interior lumen 150 of the blood vessel 128. In addition, in some cases the self-inflating balloon 94 may become trapped when being withdrawn into the distal end 158 of the inner lumen 32 of the elongate housing 22 of the actuator assembly 12. As such, it may be useful to provide a venting feature with regard to the interior volume 98 of the self-inflating balloon 94 that provides fluid communication between the interior volume 98 of the self-inflating balloon 94 and the ambient atmospheric pressure disposed about the inner catheter assembly 78 of the vascular closure assembly 10 outside of the interior lumen 150 of the blood vessel 128 being treated. Such venting may typically be carried out while the balloon inflation lumen 102 disposed between ports 104 and 106 is in a closed state preventing flow therethrough.

Given the foregoing, for some embodiments there may be a portion of the balloon inflation lumen 102 of the elongate shaft 82 that extends proximal of the balloon inflation port 104 and this proximal portion may be vented to the outside atmosphere. For such embodiments, when the plug 134 of the balloon inflation valve 112 is disposed distal to the balloon inflation port 104 with fluid communication between the inlet port 106 and inflation port 104 blocked, the inflation port 104 may thus be vented to the outside ambient atmosphere by the proximal portion of the balloon inflation lumen 102 in order to allow the interior volume 98 of the self-inflating balloon 94 to vent and deflate to a collapsed state when not being actively inflated. This arrangement may facilitate the axial translation of the self-inflating balloon 94 within the blood vessel lumen 150 as well as axial withdrawal of the self-inflating balloon 94 into the inner lumen 32 of the elongate housing 22 when not being actively inflated.

Figures 40, 41:
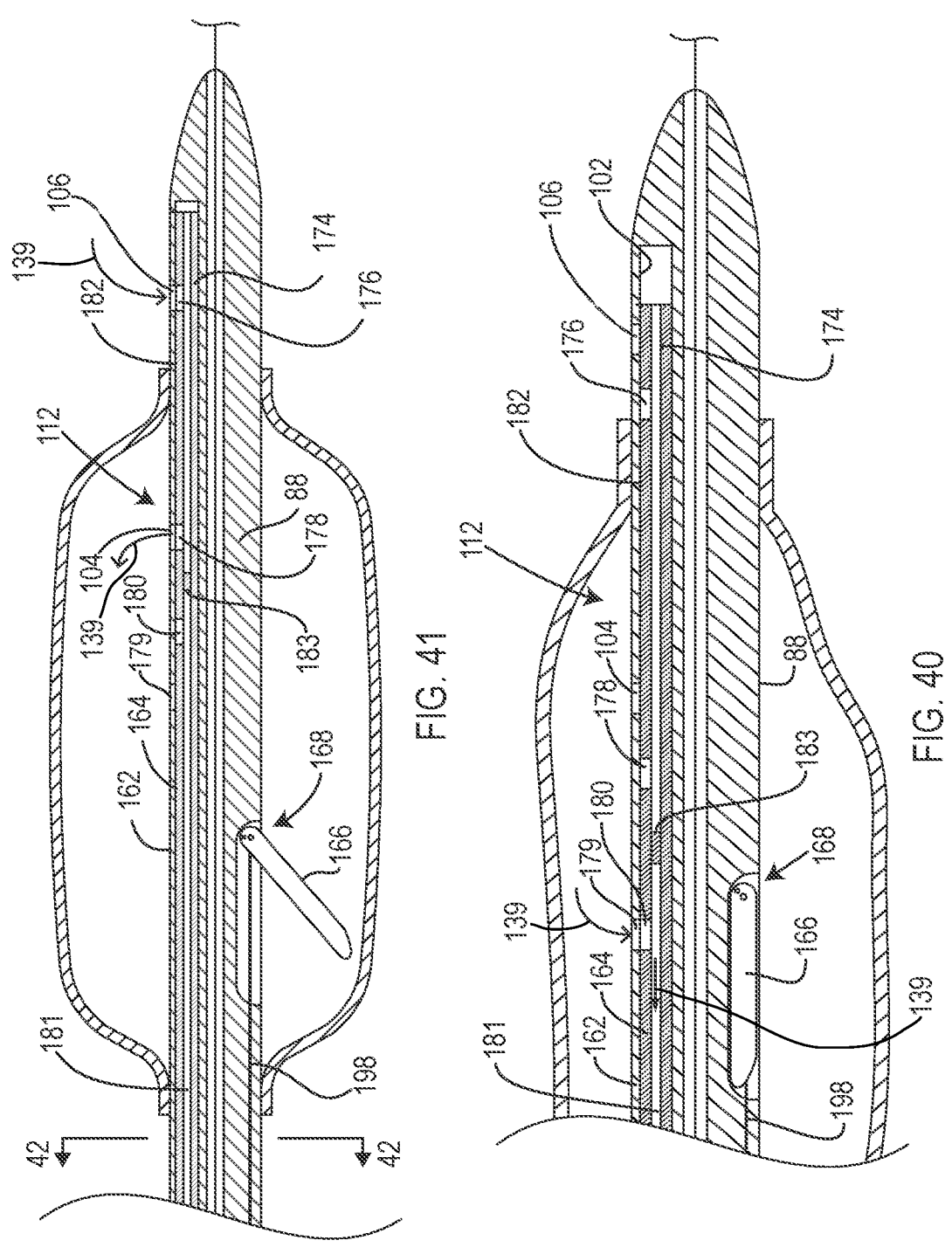
FIG. 40 is an enlarged view in longitudinal section of a distal portion an embodiment of an inner catheter assembly shown with the balloon inflation lumen thereof in a closed state to prevent inflation of the self-inflating balloon and to optionally permit venting of the interior volume of the self-inflating balloon.
FIG. 41 shows the inner catheter assembly embodiment of FIG. 40 with the balloon inflation lumen in an open state for inflation of the self-inflating balloon thereof.
Figure 42:
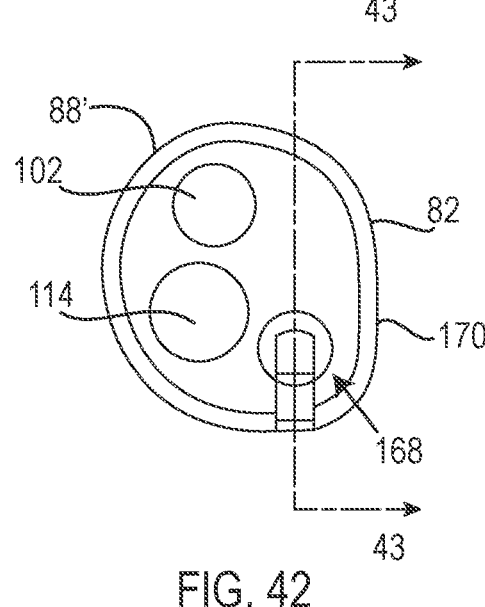
FIG. 42 is an end view of an optional foot extension housing portion of an elongate shaft of an inner catheter assembly embodiment.
Figure 43:
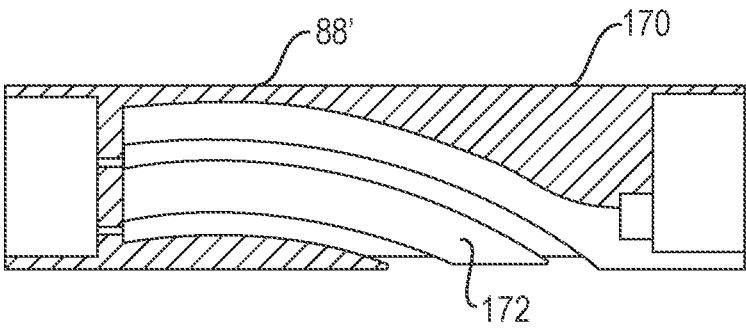
FIG. 43 is an elevation view in longitudinal section of the foot extension housing portion of FIG. 42 taken along lines 43-43 of FIG. 42.
Figure 44:
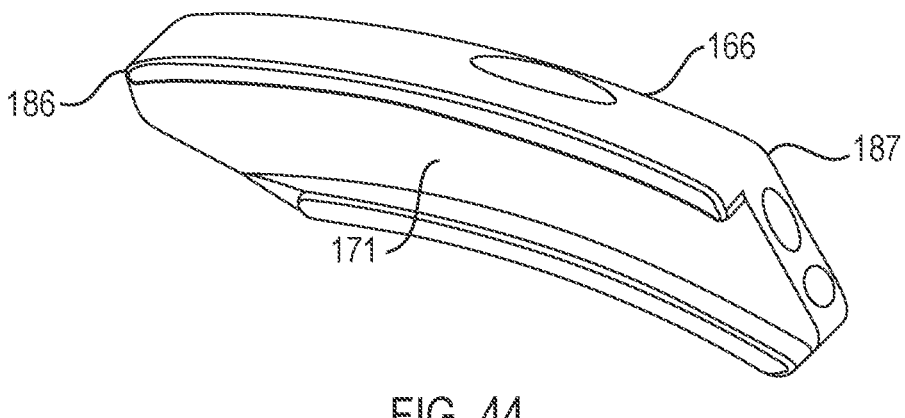
FIG. 44 is a perspective view of a foot extension embodiment.

Alternatively, a similar control of the inflation of the self-inflating balloon 94 may be achieved with a balloon inflation valve embodiment 112 that includes a cooperating pair of lamellas (or tubular members with respective interacting lamella layer portions) configured with a plurality of ports that interact upon translation between two or more relative axial positions to achieve the inflation and optional venting functions of the balloon inflation valve features discussed above. In some cases, a first lamella 162 disposed parallel to a second lamella 164 may be disposed sitting tight together but free enough so that the lamellas 162,164 may move axially in a distal and proximal direction in relation to each other with one lamella such as the first lamella 162 optionally being fixed in relation to the elongate shaft 82. In one position (when, for example, a foot extension 166 is stowed as shown in FIG. 40) the fluid communication between the blood vessel lumen 150 and the interior volume 98 of the self-inflating balloon 94 may be blocked but the fluid communication between the interior volume 98 of the self-inflating balloon 94 and venting to the ambient environment is open, as shown by arrows 139 indicating blood flow. In a second position (for example, when the foot extension 166 is deployed as shown in FIG. 41) the fluid communication between the blood vessel lumen 150 and the interior volume 98 of the self-inflating balloon 94 is open as indicated by arrows 139 and the fluid communication between the interior volume 98 of the self-inflating balloon 94 and the ambient environment is closed or otherwise blocked.

It may also be useful in some circumstances to combine the functions of certain elements of balloon inflation valve embodiments 112 and foot extension actuator embodiments 168. For example, in some cases, the actuator rod 142 of the balloon inflation valve 112 discussed above which is used to axially translate the plug 134 may also be used to actuate deployment of the foot extension 166 (discussed in more detail below) such that when the balloon inflation valve 112 is opened by proximally retracting the actuator rod 142, the foot extension 166 is simultaneously deployed by a distally extended portion of the actuator rod 142 (not shown) that is operatively coupled to the foot extension 166.

For some embodiments of such balloon inflation valve embodiments 112, the paired lamellas 162,164 may include or otherwise be made from portions of a tubular valve member 174 and the balloon inflation lumen 102 of the elongate shaft 82 that are configured to be axially displaced relative to each other by axial displacement of the tubular valve member 174 with respect to the elongate shaft 82. The tubular valve member 174 may have a first port 176 and a second port 178 coupled in fluid communication with each other that are also respectively positioned to align with the inlet port 106 and inflation port 104 of the elongate shaft 82 when the tubular valve member 174 is disposed in the open axial position as shown in FIG. 41 and positioned to not be aligned with the inlet port 106 and inflation port 104 when in the closed axial position as shown in FIG. 40. In addition, a vent port 179 of the first lamella 162 may be aligned with a third port 180 of the tubular valve member 174 in this closed state which may be configured to provide venting from the interior volume 98 of the self-inflating balloon 94 to the ambient atmosphere through the central lumen 181 of the tubular valve member 174 which may extend to the proximal chassis 92 in in some cases. Flow through the central lumen 181 may be restricted by a seal 183 disposed within the central lumen 181 proximal of the second port 178 and distal of the first port 180. In some cases, an outer surface contour 182 of the tubular valve member 174 may be configured to have a close fit with an inside surface contour 138 of the balloon inflation lumen 102 of the elongate shaft 82. Such a close fit may be tight enough to prevent a flow of liquids such as blood between the outer surface contour 182 and inner surface contour 138 but spaced enough to allow relative axial displacement between the tubular valve member 174 and the elongate shaft 82.

Figures 38, 39:
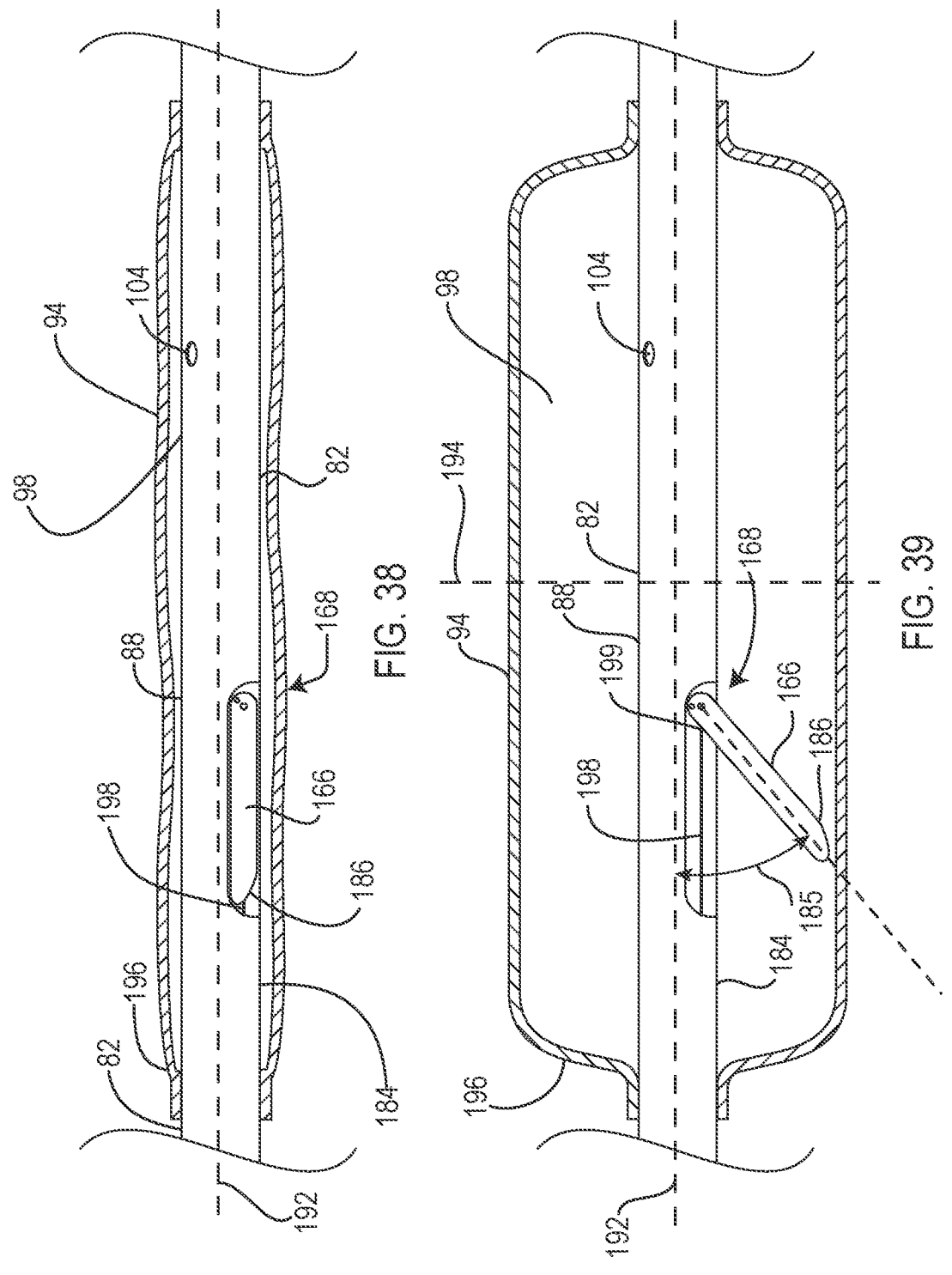
FIG. 38 is an enlarged elevation view in longitudinal section of a distal portion of an inner catheter assembly embodiment with a self-inflating balloon embodiment thereof in an uninflated state and a foot extension thereof in a retracted state.
FIG. 39 shows the inner catheter assembly embodiment of FIG. 38 with the self-inflating balloon in an inflated state and the foot extension thereof in an outwardly extended state after deployment thereof.

The inner catheter assembly 78 may further include the foot extension 166 which is disposed on the elongate shaft 82 and which may be configured to extend outwardly from a retracted position wherein the foot extension 166 is disposed substantially within a nominal outer contour 184 of the shaft 82 as shown in FIG. 38 to a deployed position wherein an outer end 186 of the foot extension 166 extends radially outward from the nominal outer contour 184 of the elongate shaft 82. In some instances, the foot extension 166 may be disposed substantially perpendicular to a longitudinal axis 192 of the elongate shaft 82 when deployed and extended. In some cases, the foot extension 166 may extend radially outward and proximally from the nominal outer contour 184 of the elongate shaft 82 forming an angle 185 of about 60 degrees to about 90 degrees with the longitudinal axis 192 of the elongate shaft 82 as shown in FIG. 39. For some embodiments, the foot extension 166 may have an axial position on the elongate shaft 82 that leaves the foot extension 166 disposed within the interior volume 98 of the self-inflating balloon 94. In other embodiments, the foot extension 166 may be so disposed in a position that is axially coextensive with the self-inflating balloon 94, but not disposed within an interior volume 98 of the self-inflating balloon 94. For such embodiments, the self-inflating balloon may include an open slot in the structure thereof (not shown) that is disposed about the foot extension 166. Such an open slot in the profile of the self-inflating balloon 94 may allow the foot extension 166 to be disposed axially coextensive with the self-inflating balloon 94 but still be deployed outwardly without interfering with the wall portion 96 of the self-inflating balloon 94 or any other suitable version of the inflatable balloon embodiments.

For some embodiments, the foot extension 166 may be disposed at about an axial mid-point 194 of the self-inflating balloon 94 to help ensure overlap between the outer surface 154 of the self-inflating balloon 94 and the perimeter surface 156 of the access hole 124 when the self-inflating balloon 94 is being deployed. For other embodiments, the foot extension 166 may be disposed distal of the axial mid-point 194 of the self-inflating balloon 94 and proximal of the distal end 108 of the self-inflating balloon 94. For yet other embodiments, the foot extension 166 may be disposed proximal of the axial mid-point 194 of the self-inflating balloon 94 and distal of a proximal end 196 of the self-inflating balloon 94 as shown in the embodiment of FIGS. 38 and 39.

The foot extension actuator 168 may be configured to change the state of the foot extension 166 between the retracted position and the deployed position. In some cases, the foot extension actuator 168 may include a foot extension actuator rod 198 disposed within an actuator rod lumen 204 of the elongate shaft 82 as shown in FIGS. 9-11. The foot extension actuator rod 198 may have a distal end 199 operatively and/or pivotally secured to the foot extension 166. The foot extension actuator rod 198 may be configured to rotate or otherwise extend the foot extension 166 in a generally outward radial direction upon axial translation of the foot extension actuator rod 198. The foot extension actuator rod 198 may further have a proximal end 206 secured to a foot actuation lever 208 on the proximal chassis 92. The foot actuation lever 208 may have a first position wherein the foot extension 166 is disposed in the retracted position, and a second position wherein the foot extension 166 is disposed in the deployed position.

Figure 45:
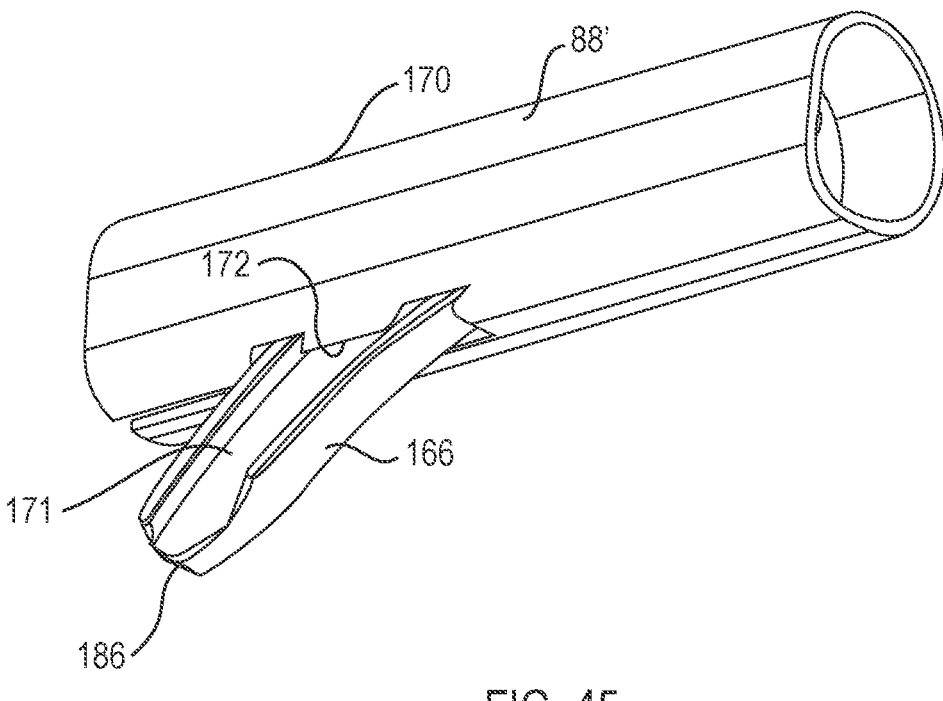
FIG. 45 is a lower perspective view of the foot extension embodiment of FIG. 44 operatively coupled to the foot extension housing portion of FIG. 43 and extending outwardly therefrom.

For some embodiments, the foot extension 166 may be operatively coupled to a foot extension housing 170 as shown in FIGS. 42-45. Such a foot extension housing 170 may be configured to form a portion 82' of the elongate shaft 82 of the inner catheter assembly 78. Some embodiments of the foot extension housing 170 and foot extension 166 may be configured such that a curved slot 171 of the foot extension 166 mates with a corresponding curved rail 172 of the foot extension housing 170 which each have the same or similar radius of curvature. This sliding and mating coupling between the respective curved slot 171 and curved rail 172 allows the outer end 186 of the foot extension 166 to rotate and extend radially outward as shown in FIG. 45 upon axial translation in a proximal direction of an inner end 187 of the foot extension 166 due to the force applied thereto by the actuation of the foot extension actuator 168 and axial translation of the associated foot extension actuator rod 198. In other embodiments of the foot extension 166 and foot extension actuator rod 198, the foot extension 166 may be configured to pivot about a pivot axis upon actuation and axial translation of the foot extension actuator rod 198 which may have a distal end thereof operatively and rotatably coupled to the foot extension 166 at a position disposed radially outward from the pivot axis as shown in the optional foot extension embodiments 166 of FIGS. 38-41. The embodiments of the inner catheter assembly 78 shown in FIGS. 38-41 may also include the foot extension housing 170 and associated portion 82' of the elongate shaft 82 as shown in FIGS. 42-45 and discussed above.

Figure 7:
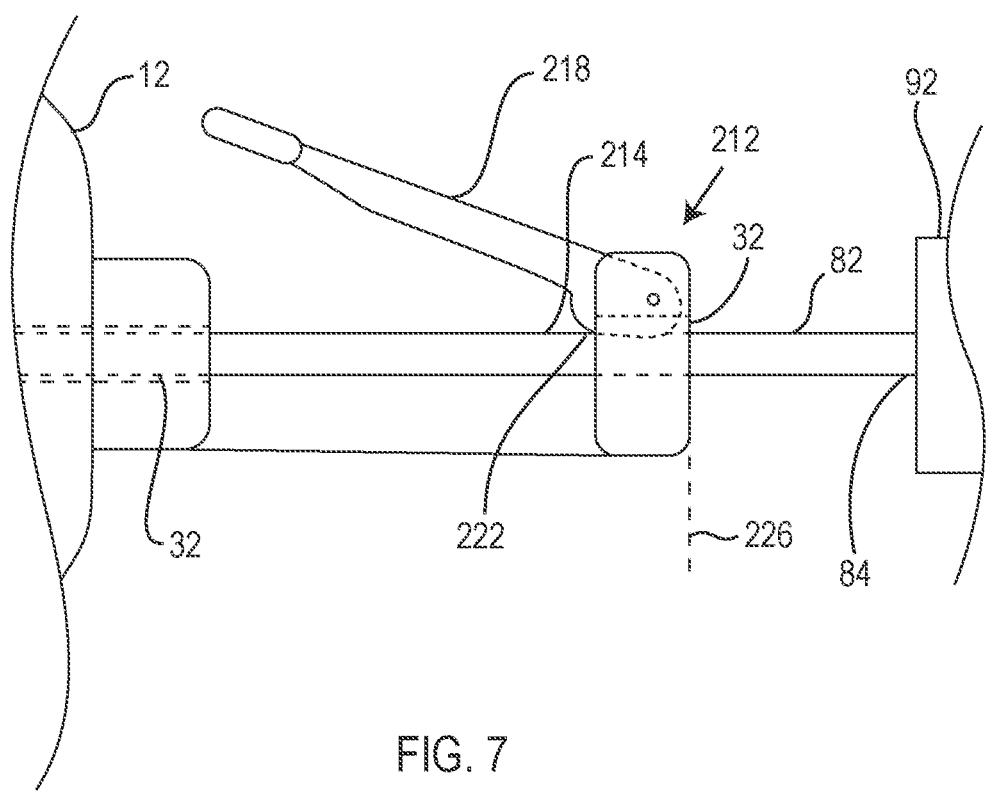
FIG. 7 is an enlarged elevation view of an inner catheter assembly position lock embodiment disposed on a proximal end of the chassis portion of the actuator assembly of FIG. 1 that includes a cam lock configuration.

For some embodiments, the actuator assembly 12 may further include an inner catheter assembly position lock 212 as shown in FIG. 7. In some instances, the inner catheter assembly position lock 212 may be configured to apply a frictional force to an outside surface 214 of the elongate shaft 82 of the inner catheter assembly 78 while the inner catheter assembly 78 is disposed within the inner lumen 32 of the elongate housing 22. The controllable application of this frictional force between the inner catheter assembly position lock 212 (which is secured to the chassis portion 14) and the inner catheter assembly 78 may be used to releasably secure the inner catheter assembly 78 to the actuator assembly 12 and temporarily prevent axial displacement of the inner catheter assembly 78 with respect to the actuator assembly 12. This arrangement may be useful when it is desirable to axially translate the actuator assembly 12 together with the inner catheter assembly 78, such as when the vascular closure assembly 10 is being initially advanced into position adjacent the access hole 124 in the blood vessel 128 as well as the passage 216 in the tissue layer 64 shown in FIG. 46 disposed above the access hole 124. For some embodiments, the inner catheter assembly position lock 212 may include a pivoting lever 218 having an offset cam 222 which is configured to intrude into the nominal contour of the inner lumen 32 of the elongate housing 22 when disposed in a locked position with a degree of inward radial intrusion being sufficient to contact the outer surface 214 of the inner catheter assembly 78 so as to resist axial translation of the inner catheter assembly 78 with respect to the actuator assembly 12 without causing permanent deformation or damage to the inner catheter assembly 78. In addition, the offset cam 222 of the pivoting lever 218 may also configured to be clear of the nominal contour of the inner lumen 32 when disposed in a released position so as to allow relative axial translation between the inner catheter assembly 78 and actuator assembly 12.

Figure 8:
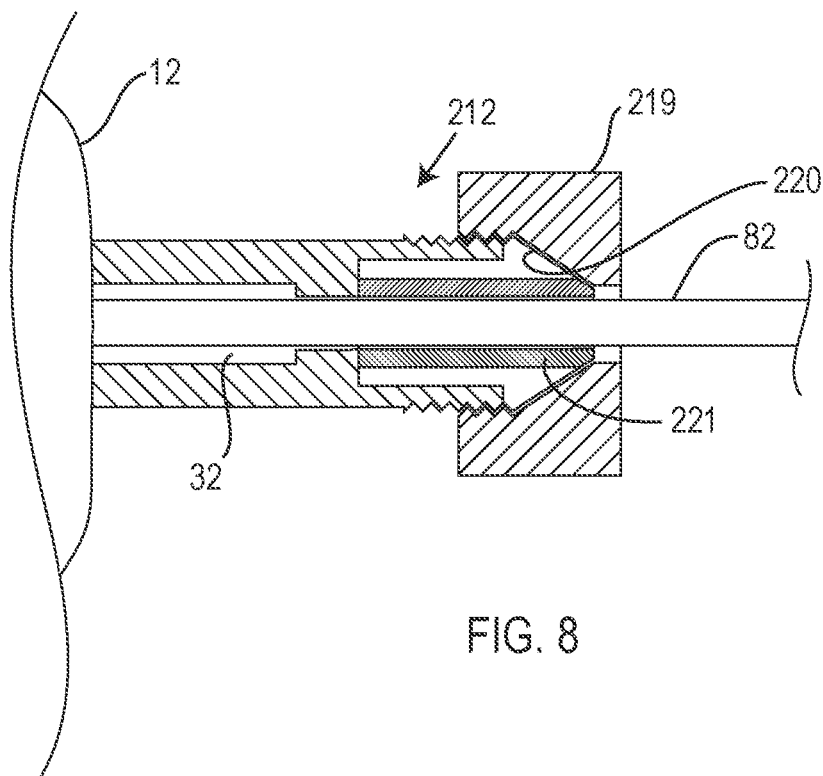
FIG. 8 is an enlarged elevation view in partial section showing an embodiment of an inner catheter assembly position lock embodiment that includes a collet type configuration.

Some embodiments of the inner catheter assembly position lock may also include a collet type inner catheter assembly position lock 212' as shown in FIG. 8. For such an embodiment 212', a threaded cap 219 may include a tapered bore 220 that mates with an outer end of a flexible slotted sleeve 221 that has an inner lumen disposed therethrough that is sized to allow passage of the elongate shaft 82 of the inner catheter assembly 78 when the threaded cap 219 is loose, but clamp onto the outside surface 214 of the inner catheter assembly 78 when the threaded cap 219 is tightened.

When determining the relative axial position between the inner catheter assembly 78 and actuator assembly 12, it may be useful to have predetermined reference points on each of these structures that are easily identifiable by a user. For example, in some cases the elongate shaft 82 may include an insertion alignment mark 224 disposed on an outside surface 214 thereof that is visually identifiable by a user as shown in FIG. 2. The actuator assembly 12 may include a cooperating proximal index 226 that is visually identifiable by a user as shown in FIG. 7. For such embodiments, an axial position of the deployed foot extension 166, more specifically, an axial position of a notch of a "v" shape formed between the deployed foot extension 166 and the elongate shaft 82 on a proximal side of the foot extension 166 in a deployed state (see FIGS. 39, 41 and 45) may be spaced by a predetermined axial separation from the distal end 28 of the elongate housing 22 when the insertion alignment mark 224 is axially aligned with the proximal index 226. In some instances, the proximal index 226 and insertion alignment mark 224 may be axially positioned on their respective structures such that this predetermined axial separation may be about 260 mm to about 285 mm, more specifically, about 270 mm to about 275 mm.

In some cases, the elongate shaft 82 may further include a retraction alignment mark 228 disposed on an outside surface 214 thereof that is visually identifiable by a user as shown in FIG. 2. For some such embodiments, when the retraction alignment mark 228 is axially aligned with the proximal index 226 this alignment may be used to indicate a relative axial relationship wherein the distal end 86 of the elongate shaft 82 of the inner catheter assembly 78 is disposed within the inner lumen 32 of the elongate housing 22. This arrangement may be useful when it is important to determine that the distal end 86 of the elongate shaft 82 of the inner catheter assembly 78 is no longer disposed within the passage 216 adjacent the access hole 124 in the blood vessel 128. In some cases, it may be desirable for the insertion alignment mark 224 and retraction alignment mark 228 are visually distinct from each other. In some cases, the insertion alignment mark 224 may be a single band of a color that is different than the color of an outside surface 214 of the elongate shaft 82 and the retraction alignment mark 228 may be of double band of the same or different color than that of the insertion alignment mark 226.

Figures 5, 6:
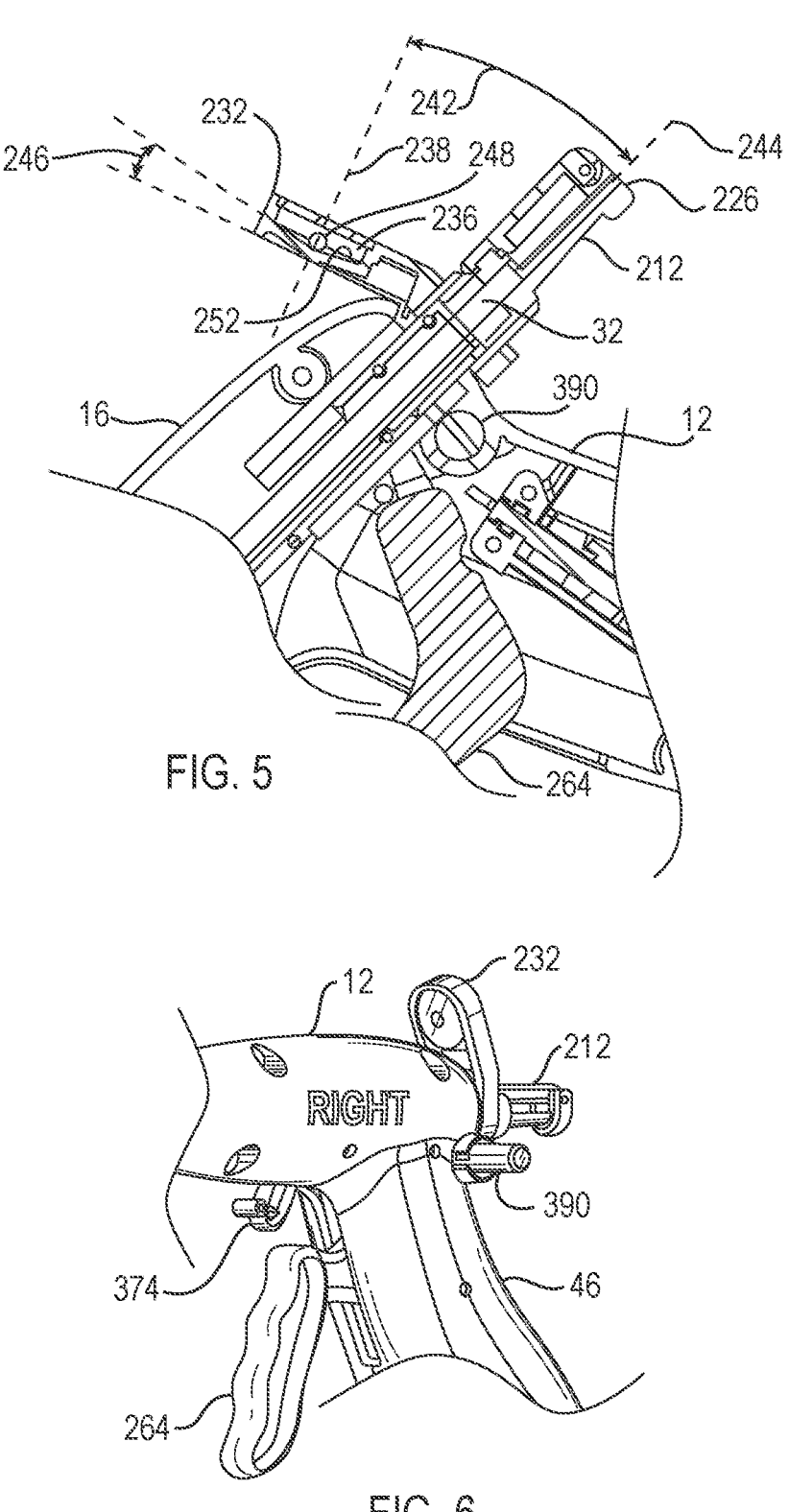
FIG. 5 is a partial cut away view of a chassis portion of the actuator assembly of FIG. 1 showing an angular alignment mechanism embodiment and inner lumen of the actuator assembly.
FIG. 6 is a partial perspective view of the actuator assembly of FIG. 1 showing the filament cutter in an undeployed state.

In order to ensure proper angular alignment of the actuator assembly 12 prior to deployment of the anchor deployers 52, it may be useful in some instances to include an angular alignment mechanism 232 as part of the vascular closure assembly 10 as shown in FIG. 5. In some instances, the actuator assembly 12 of the vascular closure assembly 10 may include the angular alignment mechanism 232 that has a boss 234 that extends from the chassis portion 12 and a conical cavity 236 having a substantially shallow configuration disposed in the boss 234 that has an axis of symmetry 238 that forms a predetermined angle 242 with respect to the longitudinal axis 244 of the elongate housing 22. The conical cavity 236 may include a predetermined cone angle 246 defined between the inner surface 252 of the conical cavity and a plane that is perpendicular with the axis of symmetry 238. The predetermined cone angle 246 may be configured to determine the sensitivity of the angular alignment mechanism 232 with lower cone angles 246 being more sensitive to angular variation and larger cone angles 246 being less sensitive to angular variations.

A ball bearing 248 or similar spherical structure may be disposed in the conical cavity 236. The ball bearing 248 may be sized to rotate freely on an inner surface 252 of the conical cavity 236 and remain centered at the axis of symmetry 238 so long as the axis of symmetry 238 does not deviate from an angular position that is perpendicular to level by an angle greater than the cone angle 246 of the conical cavity 236. In other words, when the angular orientation of the angular alignment mechanism 232 is correct, the ball bearing 248 sits in the center of the conical cavity 236 as shown in FIG. 5. If the alignment is incorrect, gravity causes the ball bearing 248 to roll away from the center of the conical cavity 236 due to the tapered bottom surface 252 of the conical cavity 236. Although referred to herein as a conical cavity 236, any other suitably configured cavity may also be used such as a spherical cavity, parabolic cavity or the like. In addition, for the embodiment shown, the axis of symmetry 238 and longitudinal axis 244 lie substantially in the same plane.

The angular alignment mechanism 232 may include a window 254 disposed over the conical cavity 236 to prevent escape of the ball bearing 248 while still permitting visualization thereof. Embodiments of the angular alignment mechanism 232 may be specifically designed to be compatible with a variety of sterilization methods, such as e-beam, and ethylene oxide (EtO), some of which would be unsuitable for a conventional bubble-level alignment fixture. For some embodiments, the cone angle 246 may be about 5 degrees to about 10 degrees. In addition, the predetermined angle 242 formed between the axis of symmetry of the conical cavity and the longitudinal axis of the elongate housing may be about 15 degrees to about 25 degrees.

Figure 12:
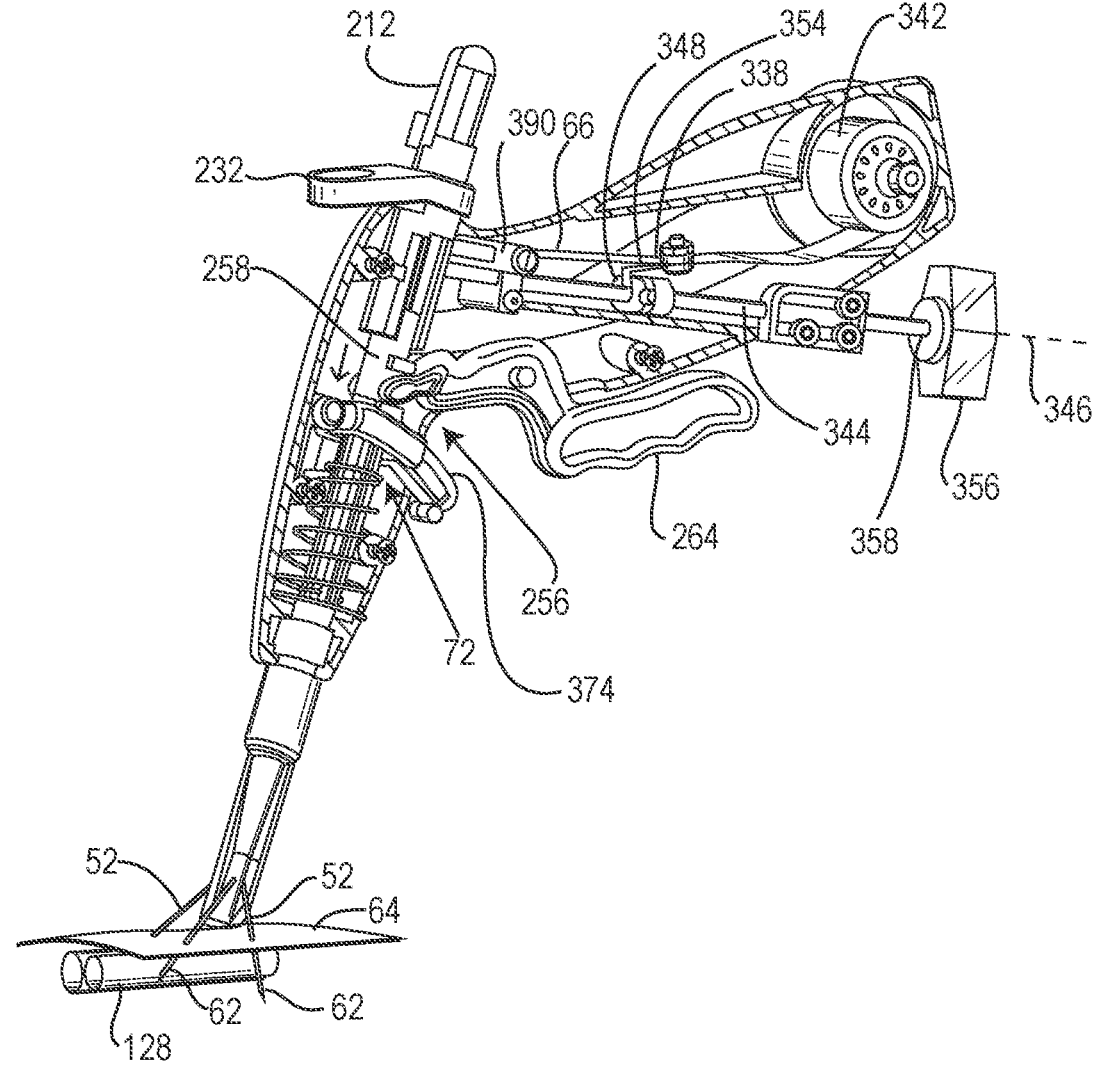
FIG. 12 is a cut away view of the actuator assembly of FIG. 1 shown with anchor deployer embodiments in a deployed state into a tissue layer disposed above and adjacent a patient's blood vessel.
Figure 13:
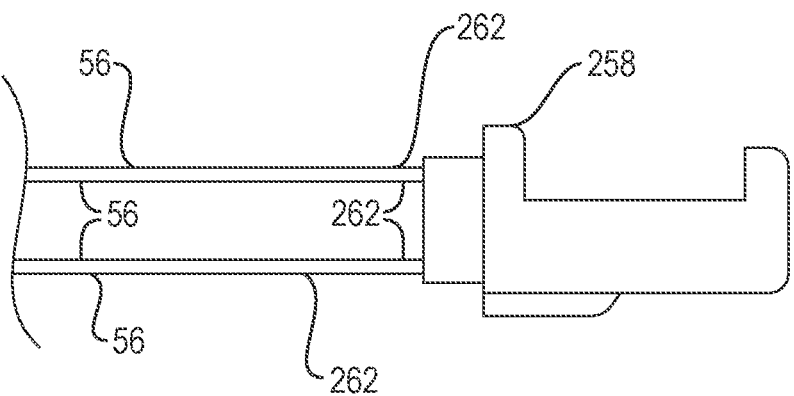
FIG. 13 is an elevation view of an anchor deployer carrier embodiment secured to a proximal end of a plurality of deployment rods.
Figure 14:
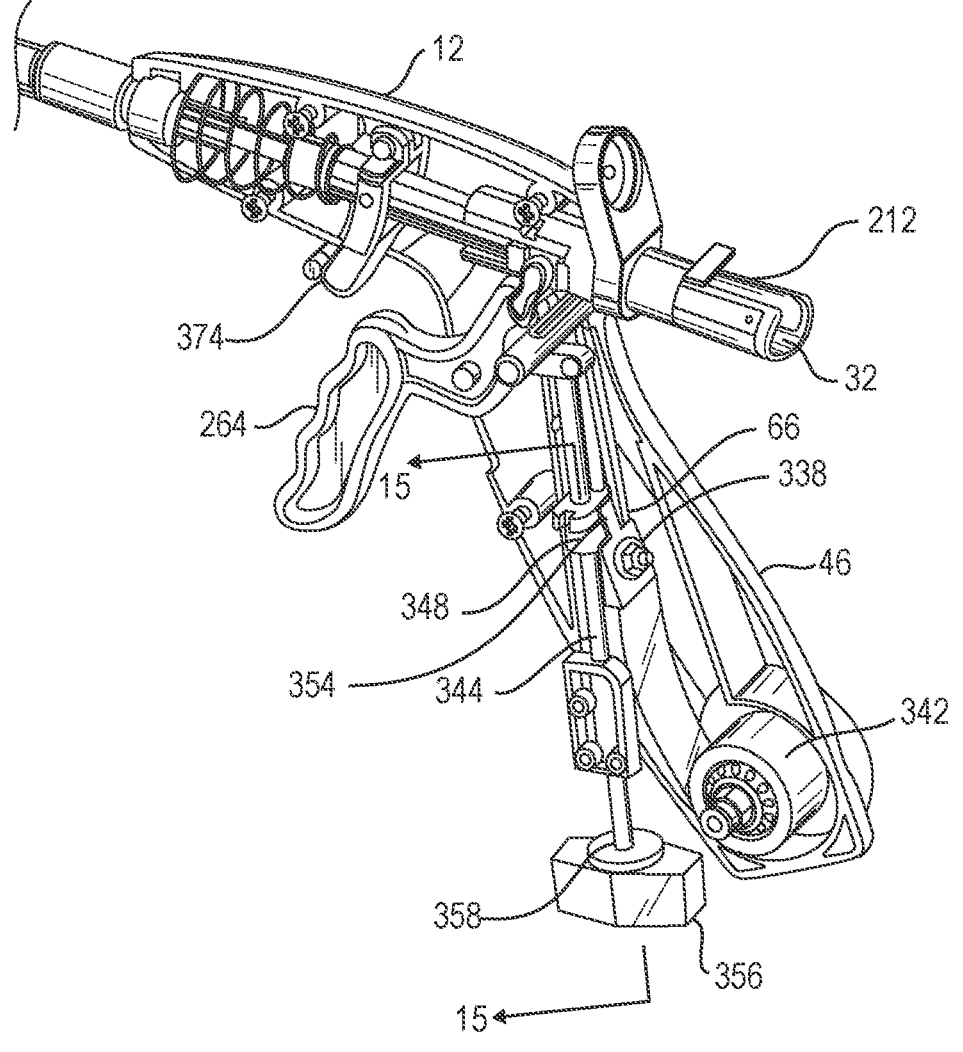
FIG. 14 is a cut away view of an actuator assembly embodiment of the vascular closure assembly of FIG. 1 shown with a filament tensioning mechanism partially activated and filaments partially tensioned.
Figure 15:
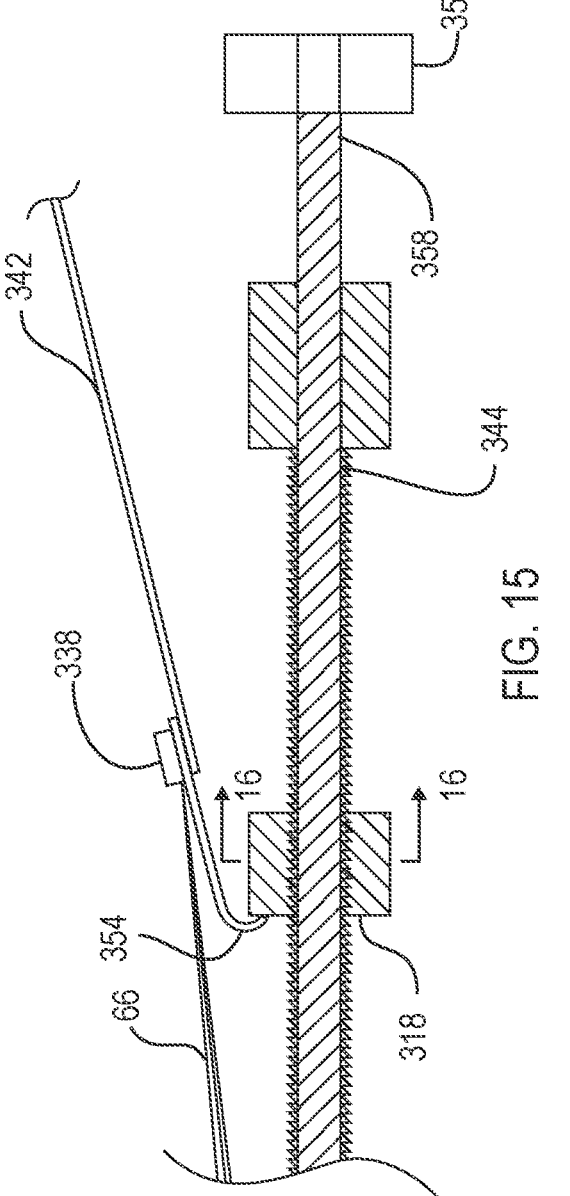
FIG. 15 is a view in longitudinal section of a filament tensioning mechanism embodiment of the actuator assembly embodiment of FIG. 14 taken along lines 15-15 of FIG. 14.
Figure 16:
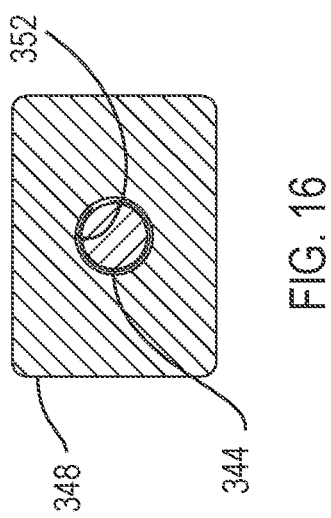
FIG. 16 is a transverse cross section view of the filament tensioning mechanism embodiment of FIG. 15 taken along lines 16-16 of FIG. 15.

Once the actuator assembly 12 and elongate housing 22 thereof are properly positioned, deployment of the plurality of anchor deployers 52 may be carried out by a variety of mechanisms and methods including an anchor deployer actuator 256 as shown in FIGS. 3, 12 and 13. For some embodiments, the anchor deployer actuator 256 of the vascular closure assembly 10 may include an anchor deployer carrier 258 which is slidably disposed with respect the chassis portion 14 and which is operatively coupled to a proximal section 262 of each of the plurality of deployer rods 56 as shown in FIG. 13. An actuator lever 264 may extend outside of the outer shell 16 chassis portion 14 and be operatively coupled to the anchor deployer carrier 258 in order to translate the anchor deployer carrier 258 in a distal direction upon actuation translation. Such axial translation of the anchor deployer carrier 258 from a starting position wherein the anchors 62 of the anchor deployers 52 are disposed substantially within a nominal outer surface contour 266 of the elongate housing 22 will axially translate each of the deployer rods 56 and associated anchors 62 in a distal and radially outward direction from the elongate housing 22 upon actuation translation as shown in FIG. 12. In some cases, the actuator lever may be manually operated such that manually applied compression imposed upon the actuator lever 264 is converted to axial translation of the anchor deployer carrier 258 in a distal direction. A return spring 268 that is operatively coupled between the actuator lever 264 and the chassis portion 14 may be configured to resist manually imposed actuation translation of the actuator lever 264 and/or anchor deployer carrier 258 and return the actuator lever 264 and anchor deployment carrier 258 from a displaced position to a starting position thereof.

Figure 12A:
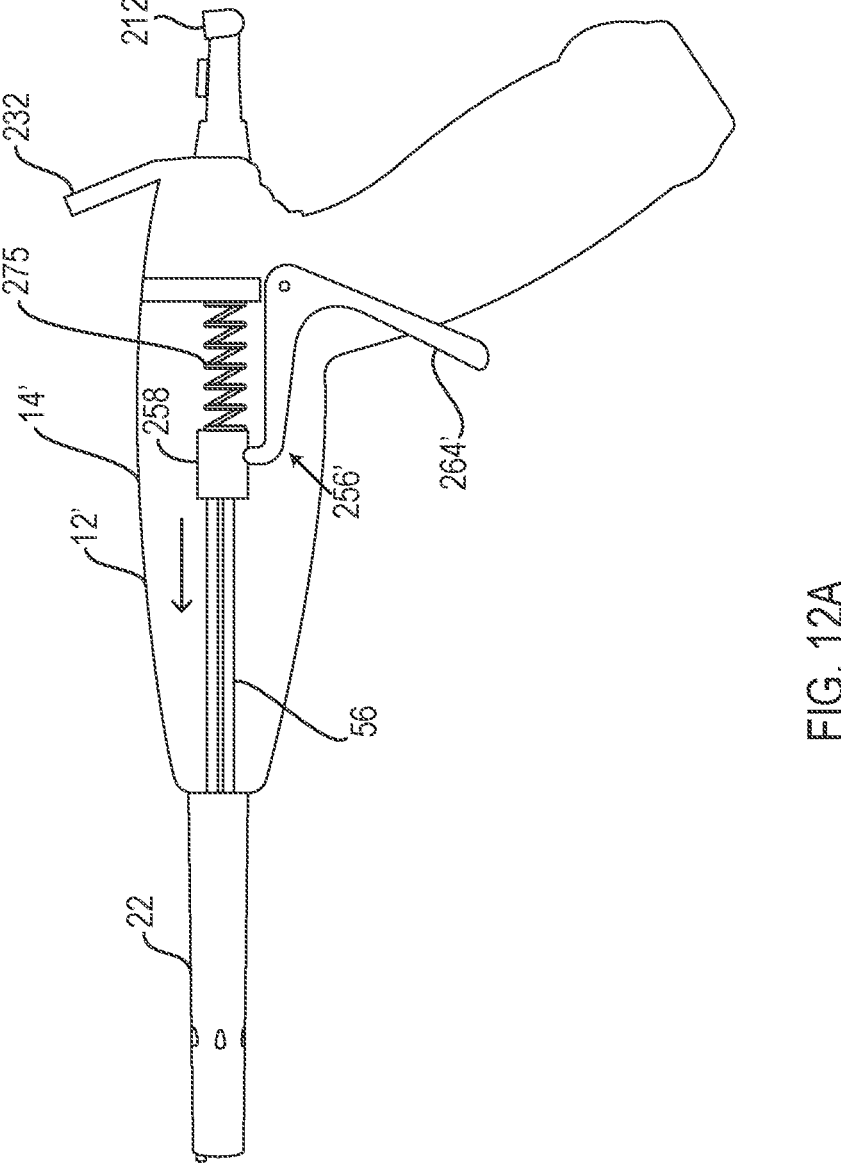
FIG. 12A is a schematic view in elevation of an actuator assembly embodiment that includes a spring driven anchor deployer actuator embodiment.

Although the anchor deployer actuator 256 discussed above uses manual compression of the actuator lever 264 to provide the distally directed force on the deployer rods 56 through the anchor deployer carrier 258, any number of other suitable devices and methods may be used to provide the distally directed force to deploy the anchor deployers 52. In some cases, a compressed spring such as deployment spring 275 included in an anchor deployer actuator 256' may be used to provide the distally directed force used to deploy the anchor deployers 52 as shown in FIG. 12A. For the deployer actuator embodiment 256' shown in FIG. 12A, the anchor deployer carrier 258' may be operatively coupled to the deployment spring 275 and the proximal section 262 of each of the deployer rods 56. The actuator lever 264' is configured to be operatively coupled to the anchor deployer carrier 258' so as to maintain the deployment spring 275 in a compressed state until the operator is ready to deploy the anchor deployers 52. Once depressed or otherwise actuated, the actuator lever 264' releases the anchor deployer carrier 258' such that the deployment spring 275 is released from its axially compressed state and the compressed spring force of the deployment spring 275 then provides the distally directed axial force onto the deployer rods 56 thereby advancing the anchor deployers 52 in a distal and radially outward direction from the distal section 34 of the elongate housing 22 as discussed above with regard to other embodiments included herein.

Referring to FIGS. 19-21, in some cases, a distal section 45 of each of the anchor deployer lumens 42 may be configured to provide an outward angular deflection of the anchor deployer 52 when the anchor deployer 52 is translating distally and extending outwardly from the distal port 44 of the anchor deployer lumen 42 or otherwise disposed within and extending from the distal port 44. In some cases, the distal section 45 of each of the anchor deployer lumens

42 may include a curved contour 270 with respect to a longitudinal axis 272 of a nominal anchor deployer lumen section 274 disposed proximal to the distal section 45 of the anchor deployer lumen 42. The curved contour 270 may be configured to provide outward angular deflection of the anchor deployer 52 when the anchor deployer 52 is translating distally and extending outwardly from the distal port 44 of the anchor deployer lumen 42 as noted above. In some cases, such a curved contour 270 may form a helical contour with respect to the distal section 34 of the elongate housing 22.

With regard to quantifying the outward angular deflection of the anchor deployer 52, a discharge axis 276 is the axis defined by a longitudinal axis of that portion of the deployment rod 56 that is extending from the distal port 44 of the anchor deployer lumen 42. In some cases, the distal section 45 of each of the anchor deployer lumens 42 may be configured to provide outward angular deflection of the anchor deployer 52 having a discharge axis 276 that forms an angle 278 of about 15 degrees to about 35 degrees with respect to the longitudinal axis 272 of the nominal anchor deployer lumen section 274 disposed proximal to the distal section 45 of the anchor deployer lumen 42 and/or the longitudinal axis 244 of the elongate housing 22. For some embodiments, the curved contour 270 of the distal section 45 of each of the anchor deployer lumens 42 may be configured to produce such range of discharge axes 276 and associated angles 278 as noted above. For some embodiments, the distal section 45 of each of the anchor deployer lumens 42 may be configured to provide an outward angular deflection of the anchor deployer 52 without the use of a curved contour. For example, an abutment, deflection block or other suitable structure (not shown) that is configured to deflect the anchor deployer 52 may be disposed in the distal section 45 of anchor deployer lumen 42 that has an otherwise straight shape without a curved contour.

In addition, the distal section 45 of each of the anchor deployer lumens 42 may have a recessed pocket 282 with an inside surface contour 284 which is configured to accept an outer surface contour of a respective anchor 62 disposed therein with a close fit therebetween. In such cases, a close fit between the inside surface contour 284 of the recessed pocket 282 and outer surface contour of the respective anchors 62 may include a snap fit or a close slip fit wherein the anchors 62 are held in place in the respective recessed pockets 282 by a lateral force generated by the distal end 58 of the deployer rod 56 that is resiliently bent into a deflected configuration by the curved contour and curvature thereof. This snap fit or close fit may be configured to hold the anchors 62 in place until the anchor deployers 52 are deployed by the anchor deployer actuator 256.

Referring to FIG. 20, the distal section 34 of the elongate housing 22 is shown disposed above and adjacent the tissue layer 64 with a longitudinal axis 244 of the elongate housing 22 being aligned with a center of the passage 216 in the tissue layer and access hole 124 of the blood vessel 128. In some cases, for such an arrangement, the longitudinal axis 192 of the elongate shaft 82 of the inner catheter assembly 78 (inner catheter assembly 78 not shown in FIG. 20 for purposes of clarity of illustration) may also be so aligned. The deployed anchor deployers 52 shown in FIG. 20 illustrate an asymmetric deployment pattern that may be useful in certain circumstances.

Figure 20A:
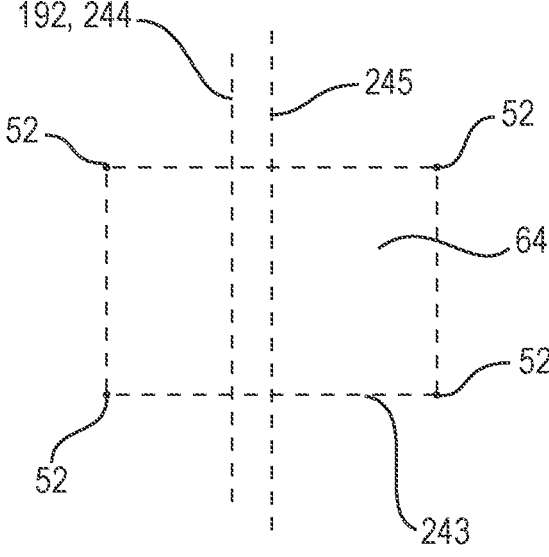
FIG. 20A is a schematic view of a deployment pattern embodiment.

For such embodiments, a deployment pattern for the anchors 62 of the plurality of anchor deployers 52 may be an asymmetric deployment pattern. In some cases, for such an asymmetric deployment pattern, the anchor puncture sites may be disposed in the tissue layer 64 on the corners of a common square or rectangular pattern 243 (or any other suitable pattern) at the plane of the tissue layer 64. However, the axis of symmetry 245 of such a deployment pattern 243 may be effectively shifted laterally, or in any other suitable direction, such that the puncture sites in the tissue layer 64 for the anchor deployers 52 on one side of the elongate housing 22 are disposed further from the longitudinal axis 244 of the elongate housing 22, longitudinal axis 192 of the elongate shaft 82 and/or center of the passage 216 than the puncture sites of the anchor deployers on the other side of the elongate housing 22 as shown in FIGS. 20 and 20A. FIG. 20A in particular shows schematically how the axis of symmetry 245 of the rectangular deployment pattern 243 is laterally shifted to the right from the longitudinal axes 192, 244 of the elongate shaft 82 and elongated housing 22 indicated by the distance shown between the axis of symmetry 245 and axes 192, 244. The desired amount or distance of this lateral shift (or shift in any other direction) may depend on a variety of factors, including certain clinical factors and morphologies. In some cases, the distance of the shift may be equal to or greater than one half a transverse width measurement of the target blood vessel, such as the artery 128. The distance of the shift may also be up to a distance of separation of the longitudinal axis 406 of the target blood vessel 128 and a longitudinal axis of an adjacent blood vessel such as the vein 130 as shown in FIG. 20. For some embodiments, the distance of the shift of the deployment pattern 243 from the axes 192 or 244 may about 3 mm to about 15 mm, more specifically, about 5 mm to about 10 mm. Such an asymmetric deployment pattern may include any other desired deployment pattern 243, other than puncture sites at the corners of a square or rectangular pattern, that yields a desired clinical result.

In some cases, the asymmetric deployment pattern 243 of the anchor deployers 52 may be wider on a side of the target blood vessel 128 that includes another vascular structure that is to be avoided and narrower on the side of the target blood vessel 128 that does not include such a structure. For example, if the target vessel 128 is a femoral artery, the deployment pattern may be wider on the side of the elongate housing 22 that corresponds to the position of the associated vein 130 (which is to be avoided by the anchor deployers) and narrower on the side of the elongate housing opposite the associated vein 130 as shown in FIG. 20.

For some embodiments, in order to produce an asymmetric deployment pattern 243 as discussed above, the curved contour 270 of the distal section 45 of a first anchor deployer lumen 42 of the actuator assembly 12 may include a discharge axis 276 forming a first angle 278 with respect to the longitudinal axis 272 of the nominal anchor deployer lumen section 274 disposed proximal of the distal section 45 of the anchor deployer lumen 42. In addition, the curved contour 270' of the distal section 45' of a second anchor deployer lumen 42' (not shown) of the same actuator assembly 12 may include a discharge axis 276' forming a second angle 278' with respect to the longitudinal axis 272' of the nominal anchor deployer lumen section 274' (not shown) disposed proximal of the distal section 45' of the second anchor deployer lumen 42', the second angle 278' being different from the first angle 278 as shown in asymmetric deployment pattern of FIG. 20. Such an arrangement wherein the axial positions with regard to the elongate housing 22 of the respective distal ports 44, 44' is the same but the discharge axis 276 of the distal ports 44, 44' varies may be used to produce an asymmetric deployment pattern as shown.

However, the overall configuration of the anchor deployer lumens 42 and respective distal ports 44 may be chosen to produce the same or any other desired deployment pattern, symmetric or asymmetric, in other ways. For example, to achieve the same or similar asymmetric deployment pattern as that shown in FIGS. 20 and 20A, the angle 278 of the discharge axis 276 of each of the deployer lumens 42 may be the same. However, the axial position of the distal ports 44 on one side (the side of the vein 130) may be disposed proximally farther from the distal end 28 of the elongate housing 22 than the distal ports 44 on the side opposite the vein 130. That is to say, that the axial position and discharge axis 276 of each of the anchor deployer lumens may be configured in any suitable manner in order to produce a desired deployment pattern and desired offset from the longitudinal axis 244 of the elongate housing 22 and/or longitudinal axis 192 of the elongate shaft 82.

Figure 30:
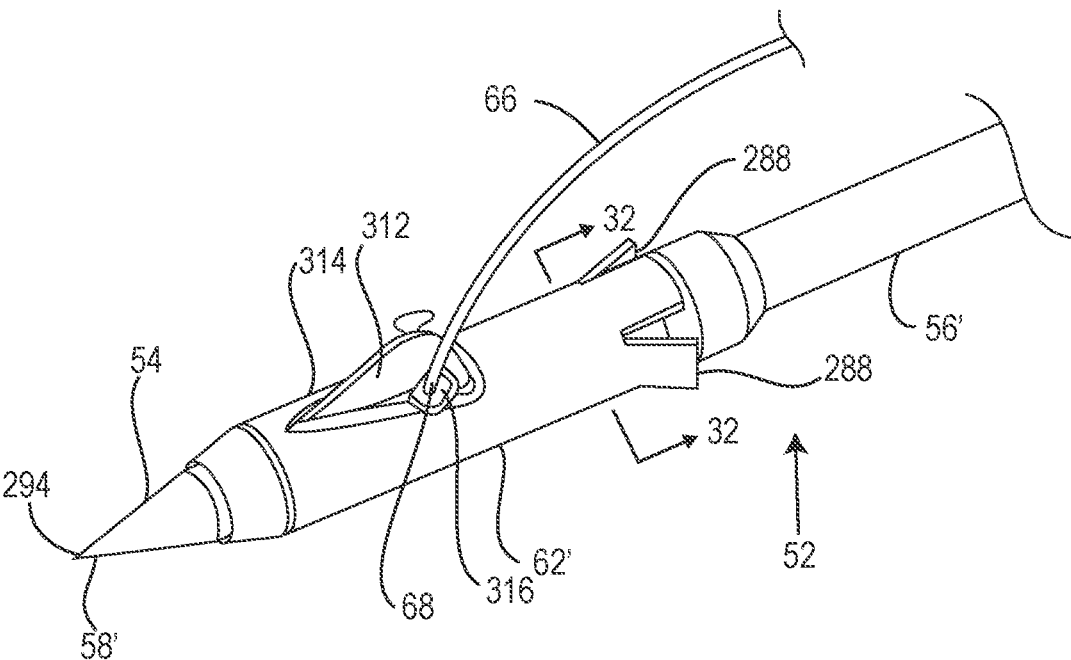
FIG. 30 is a perspective view of a distal section of another anchor deployer embodiment.
Figures 31, 32:
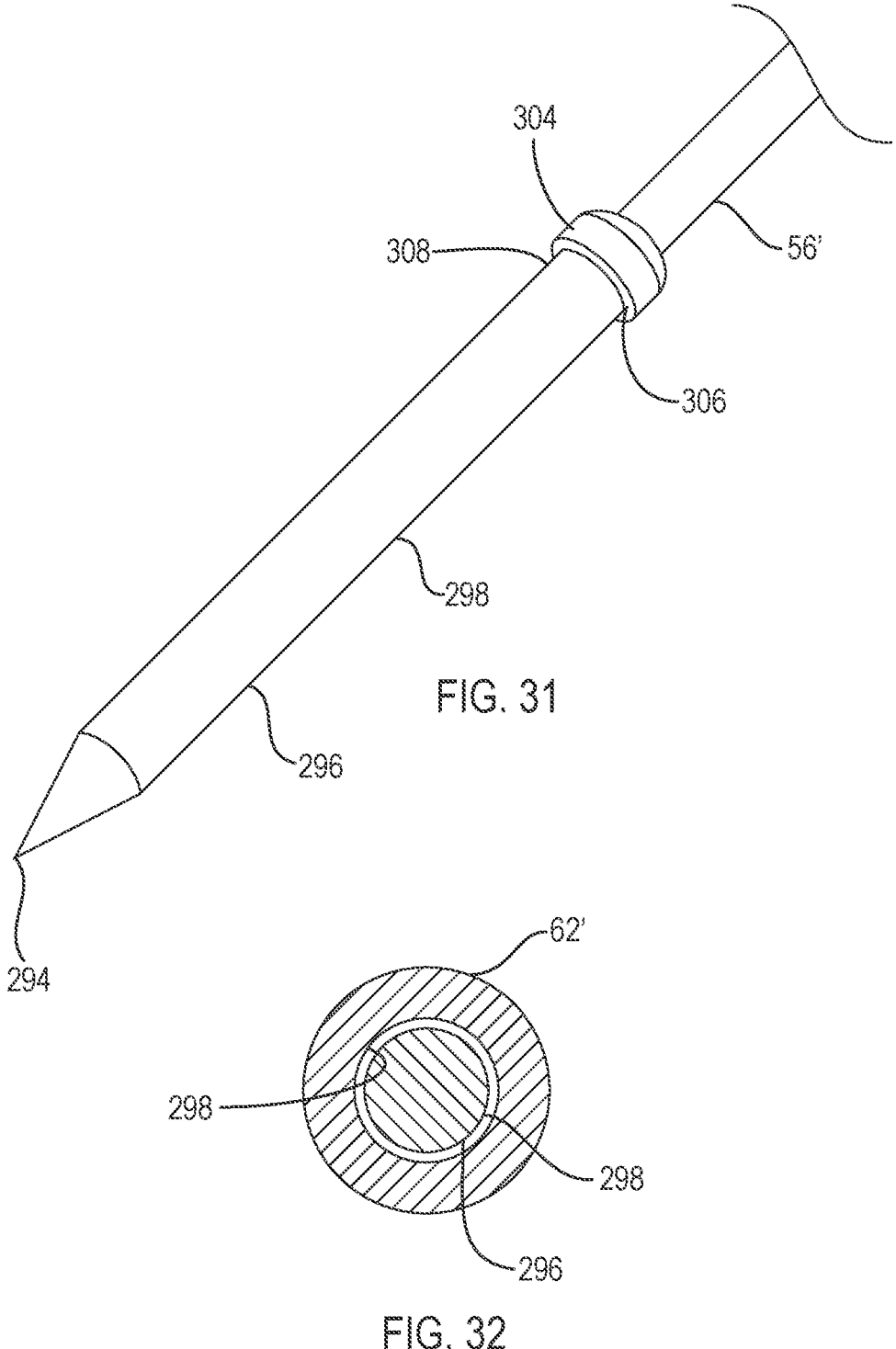
FIG. 31 is a perspective view of a distal portion of a deployment rod embodiment of the anchor deployer of FIG. 30.
FIG. 32 is a transverse cross section of the deployment rod embodiment and anchor embodiment of the anchor deployer of FIG. 30 taken along lines 32-32 of FIG. 30.
Figure 33:
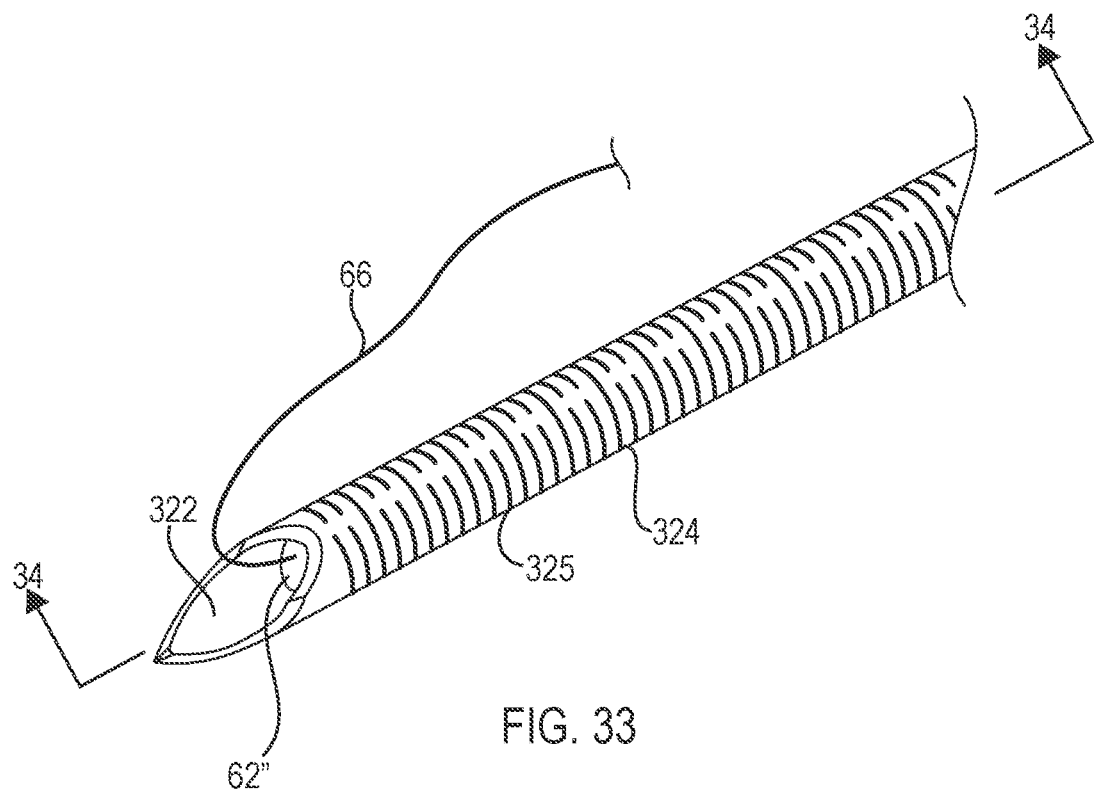
FIG. 33 is a perspective view of a distal portion of an anchor deployer embodiment that includes a deployment needle.
Figure 34:
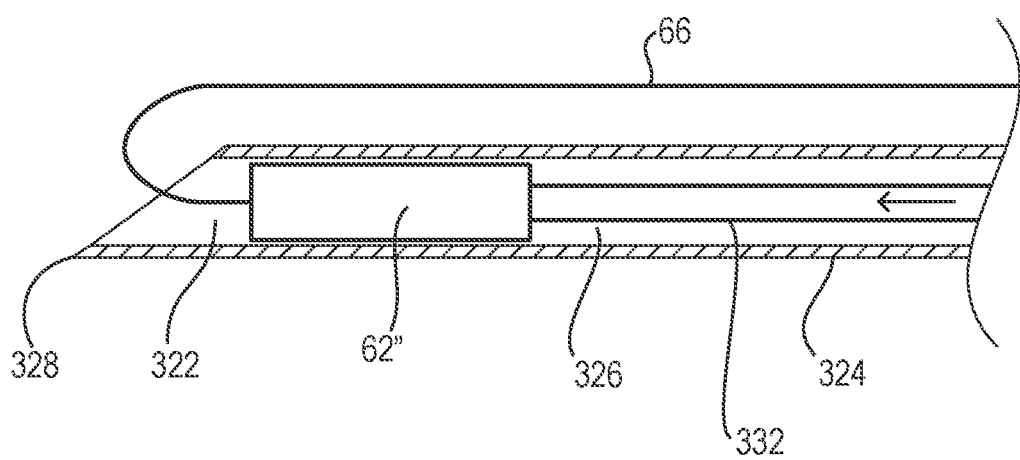
FIG. 34 is an elevation view in longitudinal section of the anchor deployer of FIG. 33 taken along lines 34-34 of FIG. 33.

Referring to FIGS. 29 and 30, any number of configurations of anchor embodiments 62 and deployment rod embodiments 56 may be used for the plurality of anchor deployers 52 that provide a useful and reliable anchoring function. In some cases, embodiments of the anchor 62 may include a sharpened distal tip 286 like a trocar tip which is configured to penetrate tissue 64 in a distal direction as shown in FIG. 29. Such anchor embodiments 62 may also include tabs 288 at the proximal end 290 of the anchor 62 that can be raised or otherwise deflected in an outward radial direction. The tabs 288 may be configured to create a feature that can engage tissue 64 and serve to aid separation of the anchor 62 from the distal end 58 of the deployment rod 56 during retraction of the deployment rod 56 from the anchor embodiments 62 by resisting retrograde translation of the anchor 62 once it is deployed into tissue. Such anchor embodiments 62 including proximal tubular portions thereof may be releasably disposed onto the distal end 58 of a respective deployment rod 56. For such embodiments, the distal tip 58 of the deployment rod 56 may have any suitable shape such as flat, blunt or the like and does not need to be sharpened as the distal tip 58 does not interact directly with tissue 64 upon distal extension and actuation. Each anchor embodiment 62 may further be secured to the distal end 68 of the filament 66, the filament being used to apply a radially inward tension force to each of the anchors 62 once they have been deployed into target tissue of the tissue layer 64. The anchors 62 having sharpened distal tips 286 may be made from any suitable rigid high strength material that is configured for tissue penetration and anchoring. In some cases, such anchor embodiments 62 may be made from metals such as stainless steel, nickel titanium alloy or the like which may, in some cases, be non-bioabsorbable. In some cases, such anchors may also include bio-absorbable materials.

In other embodiments, each anchor deployer 52 of the plurality of anchor deployers 52 may include a deployment rod 56' having a sharpened tissue penetrating tip 294 disposed on the distal end 58' of the deployment rod 56' as shown in FIG. 30. For such embodiments, the respective anchor 62' may be removably secured to the distal end 58' of the deployment rod 56' and have a tubular configuration and without a sharpened distal tip 286. Such deployment rod embodiments 62' may further include an anchor receiving surface 296 disposed proximally of the sharpened tissue penetrating tip 294 which has an outer surface contour 298 which is configured to mate with an inside surface contour of an inner lumen 302 of the tubular configuration of the anchor embodiment 62'. In addition, the deployment rod embodiment 56' may further include a shoulder 304 having a stop surface 306 which is distally facing and disposed at a proximal end 308 of the anchor receiving surface 296. In such instances, the stop surface 306 may extend radially outward from the anchor receiving surface 296 and function to fix the axial position of the anchor 62' on the anchor receiving surface 296 during tissue penetration.

Such anchor embodiments 62' may further include filament attachment feature or loop 312 disposed on an outer surface 314 of the anchor 62' or in any other suitable location which has a filament hole 316 or other suitable feature which is configured to be secured to the distal end 68 of a filament 66 such as a suture. In some cases, the filament hole 316 may be secured to the distal end 68 of the filament 66 by crushing or crimping the loop material of the filament attachment feature 312 onto the distal section 68 of the filament 66. Such a filament attachment feature 312 may also be used on any other anchor embodiments 62 discussed herein including those anchor embodiments having sharpened distal tips 286.

The anchor embodiments 62' without a sharpened distal tip 286 may be made from any suitable rigid high strength material that is configured for anchoring. In some cases, such anchor embodiments 62' may be made from metals such as stainless steel, nickel titanium alloy or the like which may, in some cases, be non-bioabsorbable. In some cases, such anchor embodiments 62' may also include bio-absorbable materials.

Some anchor deployer embodiments 52 may include anchors 62" which are each secured to an elongate and flexible filament 66 and which may be configured to be distally ejected from a distal end 322 of an inner lumen 326 of hollow deployment needle 324. For such embodiments, the hollow deployment needle 324 may have a sharpened distal tip 328 and be configured to penetrate tissue 64 upon deployment such that the anchor 62" disposed therein does not require any tissue penetrating characteristics. As such, the anchor embodiments 62" may have a variety of configurations due to serving only a single purpose, i.e., anchoring once deployed into target tissue 64 without the need to be sharpened for tissue penetration or inclusive of features such as tabs 288 to resist proximal withdrawal in tissue 64 to facilitate removal from deployment rods 56 as discussed above. The hollow deployment needles 324 may take the place of the deployment rods 56 and have their proximal ends secured to a carrier such as the anchor deployer carrier 258 and function in the same or similar manner as the anchor deployer actuator 256 discussed herein.

These anchor embodiments 62" may be deployed from the distal ends 322 of the inner lumens 326 of the hollow deployment needle 324 by distal translation of pusher rods 332 disposed within the inner lumen 326 of the hollow deployment needles 324 proximal of the anchor 62". The pusher rod embodiments 332 may have a flexible configuration and be disposed within and along the inner lumens 326 of the hollow deployment needles 324. The pusher rods 332 may be distally advanced and deployed so as to deploy the anchors 62" from the distal ends 322 by any suitable means including an actuator (not shown) that may be similar to or the same as the anchor deployer actuator embodiments 256 shown and discussed herein. For such embodiments, proximal ends or sections of the pusher rods 332 may be operatively coupled to a carrier, such as the anchor deployer carrier 258 and associated structures. Some hollow deployment needle embodiments 324 may include slotted tubes of resilient high strength material such as slotted hypo tubes made from stainless steel, nitinol or the like including transverse slots 325 disposed through a wall of the deployment needle 324. The anchor embodiments 62" may include rigid or compliant bio-compatible materials such as stainless steel, nitinol, PTFE pledgets, bio-absorbable polymers, and non-bioabsorbable polymers. In some instances, the anchors 62" may be configured to expand after deployment from the distal ends 322 of the inner lumens 326 of the hollow deployment needles 324.

The actuator assembly 12 of the vascular closure assembly 10 may also include a filament tensioning mechanism 336 which is configured to controllably apply axial tension to the filaments 66 of the respective plurality of anchor deployers 52 in order to pull the filaments 66 back into the elongate housing 22 and draw the anchors 62 which have been deployed into the tissue layer 64 closer together. In some cases, the filament tensioning mechanism 336 may include a filament terminal 338 which is secured to proximal ends of the filaments 66 of the plurality of anchor deployers 52 and a tensioning spring 342 which is operatively secured to the filament terminal 338. The filament terminal 338 may be translatable from a first position wherein there is no tension force applied to the filaments 66 by the filament terminal 338 and a second position wherein the tension force is applied to the filaments 66 by the tensioning spring 342 through the filament terminal 338.

For some embodiments, the filament tensioning mechanism 336 may be disposed on the chassis portion 14 and further include a threaded rod 344 which is configured to be rotatable about a longitudinal axis 346 thereof but axially fixed with respect to the chassis portion 14. The filament tensioning mechanism 336 may also include a tension control block 348 that has a threaded bore 352 which is operatively coupled to the threaded rod 344. For such embodiments, the tension control block 348 may be rotationally fixed but axially translatable with respect to the chassis portion 14 such that rotation of the threaded rod 344 relative to the chassis portion 14 and tension control block 348 axially translates the tension control block 348 with respect to the chassis portion 14. In addition, a tension transfer clip 354 may be used to releasably couple the filament terminal 338 to the tension control block 348 in an orientation that opposes a tension force of the tensioning spring 342 in order to controllably apply the tension force of the tensioning spring 342 to the filaments 66 through the filament terminal 338. The filament tensioning mechanism 336 may also have a knob 356 secured to an outer end 358 of the threaded rod 344 in order to provide a comfortable grip for a user applying rotational force to the threaded rod 344.

Figure 57:
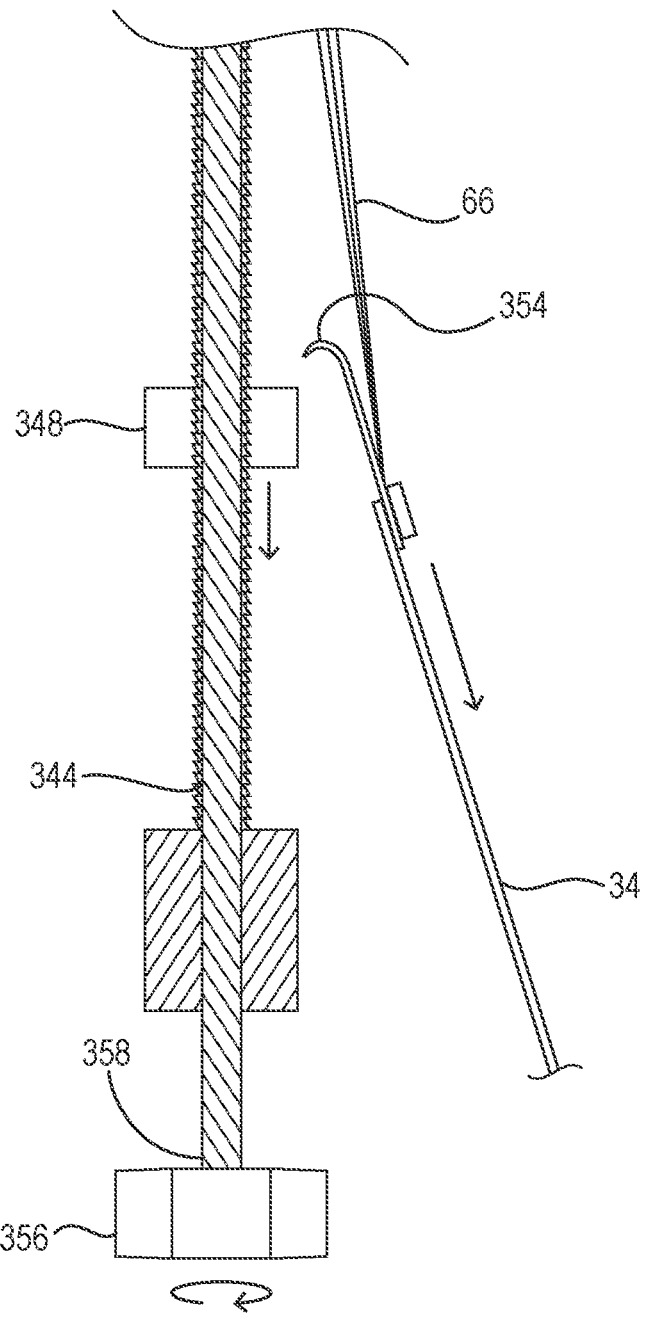

For this configuration, at the beginning of a procedure prior to activation of the knob 356, the tension control block 348 is disposed in an upper axial position along the threaded rod 344 wherein the entire tension force of the tensioning spring 342 is being transferred to and opposed by the tension control block 348 through the tension transfer clip 354 with no tension being applied to the filaments 66. As the knob 356 is rotated and the tension control block 348 translates downward, the opposition to the tension force generated by the tensioning spring 342 is decreased with respect to the tension control block 348 as any slack in the filaments 66 is removed and that tension force begins to be applied to the filaments 66. As the knob 356 is further rotated and the tension control block 348 translates further downward, more and more of the tension force is transferred from the tension control block 348 and onto the filaments 66 through the filament terminal 338. Eventually, all of the tension force from the tensioning spring 342 is transferred to the filaments 66 and the tension transfer clip 354 completely decouples from the tension control block 348 as shown in FIG. 57 and discussed below. Such a configuration is very useful for controllably applying a consistent and repeatable tension force to the filaments 66, particularly where the tensioning spring 342 is a constant force type spring that does not vary significantly in tensioning force as a function of small displacements of the end of the tensioning spring 342, as is the embodiment shown.

Figure 22:
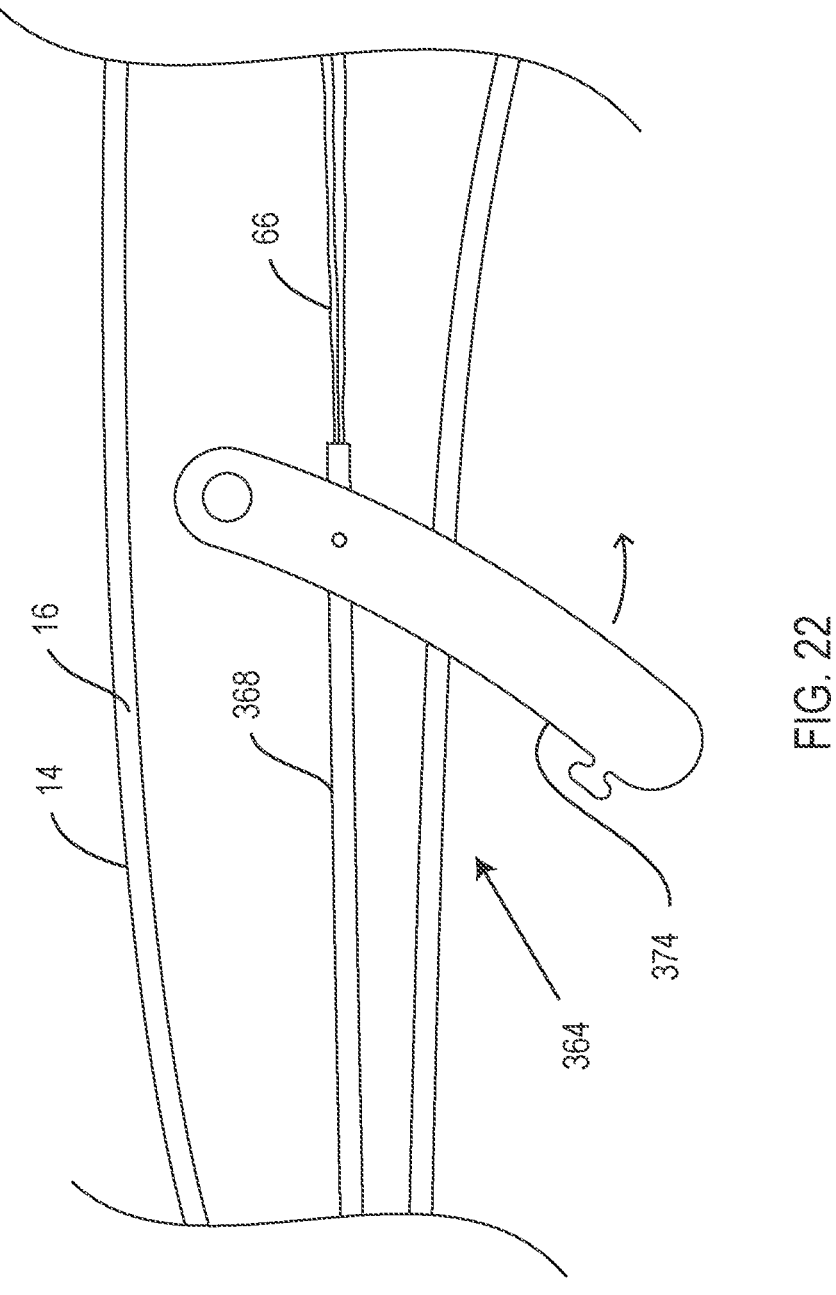
FIG. 22 is a cut away view of the chassis portion of the actuator assembly of FIG. 1 illustrating a filament tube actuator embodiment secured to a proximal portion of the filament tube.
Figure 23:
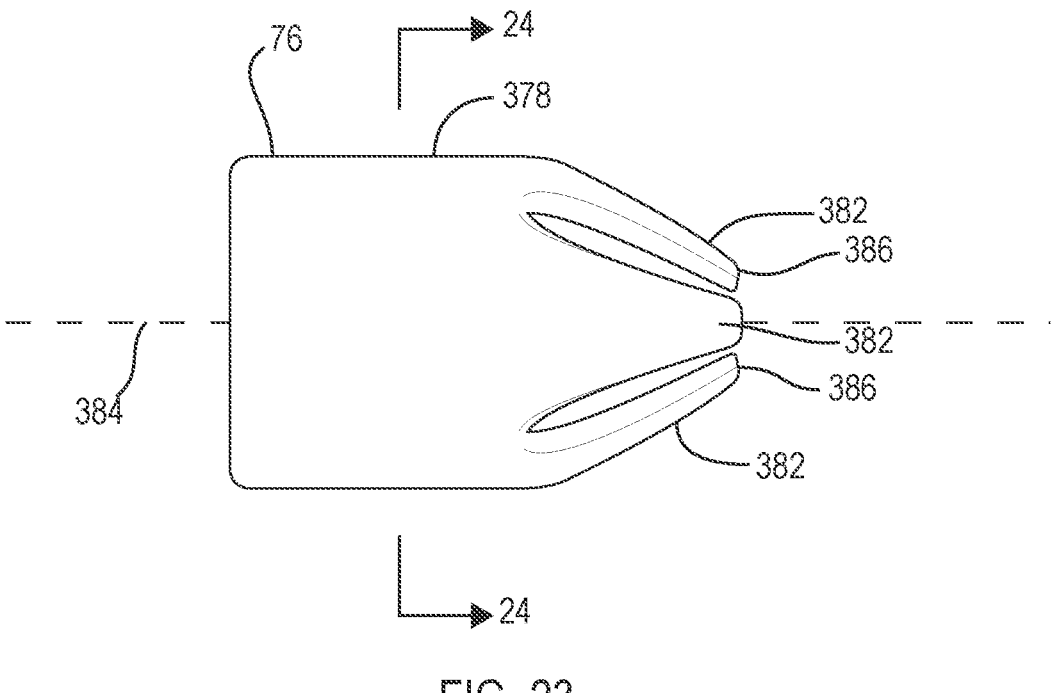
FIG. 23 is an elevation view of a filament lock embodiment.
Figure 24:
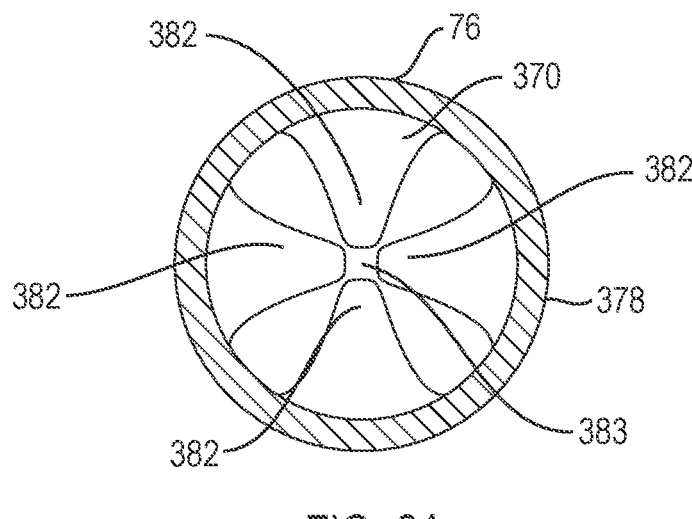
FIG. 24 is a transverse section view of the filament embodiment of FIG. 23 taken along lines 24-24 of FIG. 23.
Figures 25, 26:
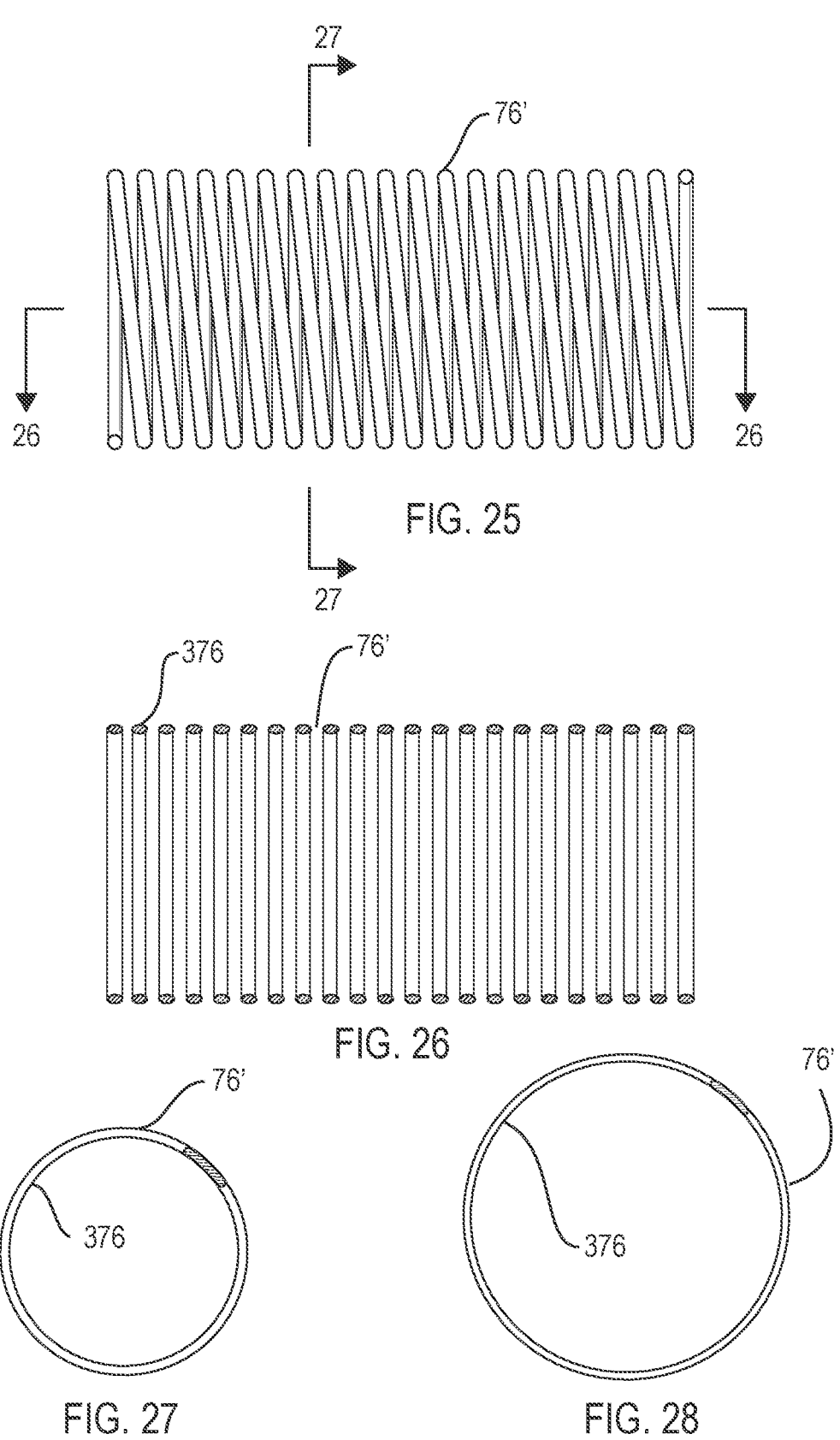
FIG. 25 is an elevation view of another filament lock embodiment.
FIG. 26 is an elevation view in longitudinal section of the filament lock embodiment of FIG. 25 taken along lines 26-26 of FIG. 25.

Once the anchors 62 have been deployed by the anchor deployers 52 and the filaments 66 retracted in order to reduce or close the passage in the tissue layer 64, it may be useful to fix the filaments 66 in the retracted configuration. Some embodiments of the actuator assembly 12 of the vascular closure assembly 10 may include the filament lock mechanism 72 as shown in FIGS. 3, 21-23 and 59-60. Embodiments of the filament lock mechanism 72 may include the filament tube 37 which has a distal section 40 which is slidably disposed in a close fitting bore 362 at a distal section 34 of the elongate housing 22. The filament tube 37 may also have a distal end 364 which extends distally beyond a distal shoulder surface 366 of the close fitting bore 362. The filament tube 37 may be slidably disposed in an axial direction relative to the elongate housing 22 and distal shoulder surface 366 and include the inner filament lumen 36 disposed about the filaments 66. The filament tube 37 may further include a proximal section 368 as shown in FIG. 22.

The filament lock mechanism 72 may also include the filament lock 76 (or a plurality of filament locks 76) which has an inner lumen 370 which is disposed about the distal end 364 of the filament tube 37 in an axial position that is distal of the distal shoulder surface 366 of the close fitting bore 362. Embodiments of the filament lock 76 may be configured to be self-contracting from an expanded state to a relaxed state and configured to clamp onto the filaments 66 disposed in the filament lumen 36 of the filament tube 37 once the outward radial support producing the expanded state of the filament tube 37 is removed. In some embodiments, a filament guide 372 may also be disposed on the distal end 364 of the filament tube 37 in order to provide a smooth radiused transition for tensioned filaments 66 being routed into the distal port 38 of the filament lumen 36 of the filament tube 37 and to prevent abrasion or other damage to the filaments 66 at this position where they are being subjected to a right angle bend at a small radius in some cases. A filament lock bushing 373 may also be disposed on the filament tube 37 proximal of the filament lock 76 and distal of the distal shoulder surface 366. The filament lock bushing 373 may have an inner lumen that is a close but slidably disposed fit with the outside surface of the filament tube 37 similar to that of the close fitting bore 362.

The filament lock mechanism 72 may further include a filament tube actuator 374 which is operatively coupled to the proximal section 368 of the filament tube 37 and which is configured to axially retract the filament tube 37 in a proximal direction relative to the distal shoulder surface 366 upon activation so as to push the filament lock 76 off of the distal end 364 of the filament tube 37 and allow the filament lock 76 to clamp onto the filaments 66 disposed in the filament lumen 36 of the filament tube 37. Some embodiments of the filament lock mechanism 72 may have a plurality of filaments locks 76 disposed axially adjacent each other on the distal end 364 of the filament tube 37 in an axial position distal of the distal shoulder surface 366 of the close fitting bore 362. In some cases, the filament tube 37 may have a rigid tubular structure comprised of a high strength material. In some cases, the high strength material of the filament tube 37 may include stainless steel.

Some embodiments of the filament lock 76 may include a "trailing lock" type configuration with a tubular structure including a main body portion 378 and also including a plurality of fingers 382 extending proximally from the main body portion 378 as shown in FIGS. 21-24. In some cases, the fingers 382 may be of sufficient axial length and elastically biased towards a center longitudinal axis 384 of the main body portion 378 such that respective distal ends 386 of the fingers 382 are configured to be self-contracting in an inward radially oriented direction. The fingers 382 may be so self-contracting from an expanded state to a relaxed state so as to clamp onto the filaments 66 disposed within the inner lumen 370 of the filament lock 76 when the fingers 382 are in the relaxed state. In the contracted state, an inside surface of the distal ends 386 of the fingers 382 may form a residual lumen 383 in the absence of any filaments disposed therein. In addition, these finger embodiments 382 may be elastically spread in an outward radial direction to a relative transverse separation to generate the expanded state which may be sufficient to fit onto an outer surface of the distal end 364 of the filament tube embodiments 37. For the filament lock embodiment 76 shown, the fingers 382 have a generally triangular shape with a base portion disposed opposite the distal end 386 and adjacent the proximal end of the main body portion 378 that is wider than the respective distal end 386 thereof.

For some embodiments, an axial length of the main body portion 378 may be the same as or similar to an axial length of the fingers 382. For such embodiments, an overall axial length of the filament lock embodiments 76 may be about 0.06 inches to about 0.1 inches, more specifically, about 0.075 inches to about 0.085 inches. Such filament lock embodiments may have an inner lumen 370 with an inside diameter of about 0.04 inches to about 0.06 inches, more specifically, about 0.045 inches to about 0.055 inches. The same embodiment, may, in some cases, have wall thickness of the tubular structure of the main body portion 378 and fingers 382 of about 0.013 inches to about 0.023 inches, more specifically, about 0.016 inches to about 0.020 inches. For some embodiments, a ratio of an axial length of the fingers 382 to the inside diameter of the inner lumen 370 may be about 0.6 to about 1.5. In some cases, the residual lumen formed by the distal ends 386 of the fingers 382 in a relaxed state in the absence of any filaments 66 disposed therein may have a transverse dimension of about 0.010 inches to about 0.015 inches and a ratio of such a residual lumen to the inside transverse dimension of the inner lumen 370 may be about 0.1 to about 0.7. For some embodiments, a ratio of a wall thickness of the tubular structure of the main body portion 378 relative to an outer diameter of the tubular structure of the main body portion 378 may be about 0.05 to about 0.25. For the filament lock embodiment 76 shown, the fingers 382 are substantially evenly spaced about a circumference of the main body portion 378, however, any suitable circumferential spacing may be used. In some instances, embodiments of the filament lock 76 may have about 3 fingers 382 to about 10 fingers 382, more specifically, about 4 fingers 382 to about 6 fingers 382. Some embodiments of such filament locks 76 may be made from or include highly resilient materials including superelastic materials. Such superelastic materials may include superelastic polymers or superelastic metal alloys such as nickel titanium alloys or the like.

Some embodiments of the filament lock 76' may include a coiled spring filament 376 wherein the inner lumen 370 of the filament lock 76' is sized to clamp onto the filaments 66 disposed therein when in a contracted state as shown in FIGS. 25-28. In some such embodiments, coiled spring filament 376 may have a non-round transverse cross section profile. For example, in some cases, the transverse cross section profile of the coiled spring filament may have rectangular or diamond shaped profile so that the sharp edges of such profiles may be used to bite into the outside surface of the filaments 66 and provide an effective lock therebetween. In some instances, such an arrangement may provide a more secure lock between the filaments than might be provided by a coiled spring filament 376 having a round or substantially round transverse cross section profile. For such embodiments, the inner lumen 370 may be elastically enlarged to a transverse dimension sufficient to fit onto an outer surface of the distal end 364 of the filament tube 37 as shown in FIG. 28.

Figure 17:
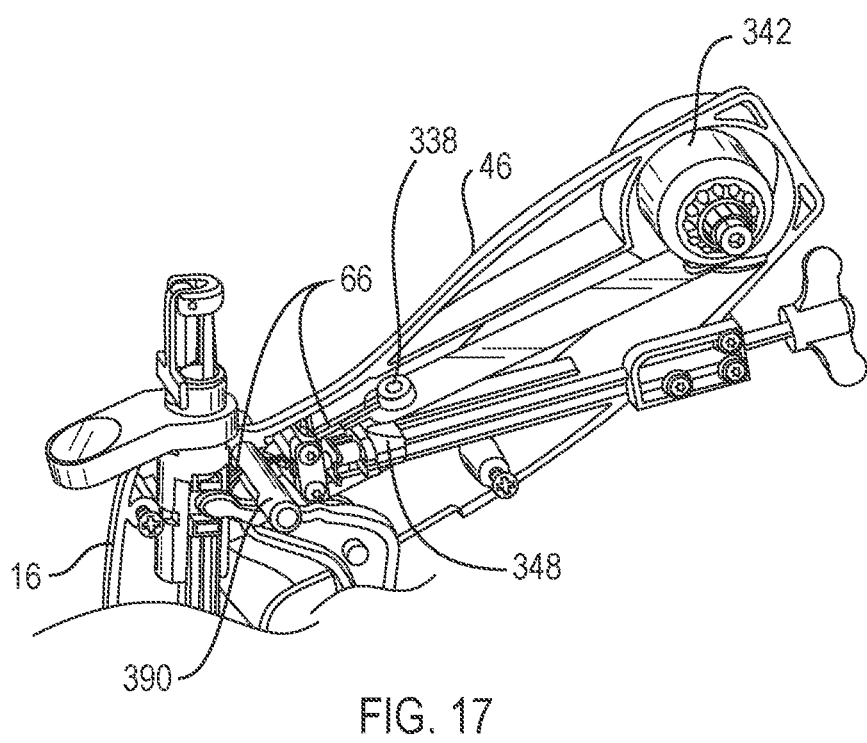
FIG. 17 is a partial cut away view in perspective of the actuator assembly of FIG. 1 illustrating a tensioning spring of a filament tensioning mechanism and a filament cutter embodiment.
Figure 18:
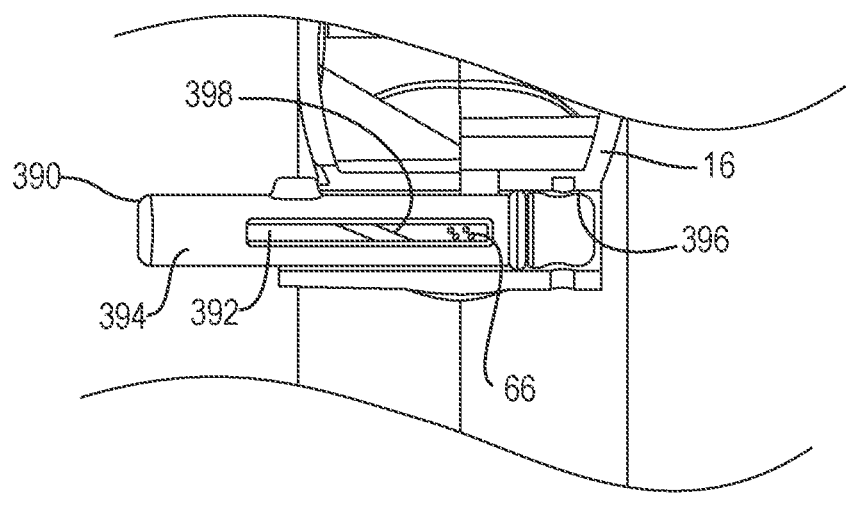
FIG. 18 is an enlarged view of the filament cutting mechanism of the actuator assembly embodiment of FIG. 17.

Once the retracted filaments 66 of the vascular closure assembly 10 have been locked in place relative to each other, it may be useful to cut the filaments 66 at a position proximal of the filament lock 76. As such, some embodiments of the actuator assembly 12 further may include a filament cutter 390 disposed in operative arrangement with the filaments 66 of the respective plurality of anchor deployers 52 as shown in FIGS. 12, 17, and 18. In some cases, the filament embodiments 66 may include sutures and the filament cutter 390 may include a suture cutter including a sharpened blade 392 that is angled towards the sutures 66 and disposed in a slide 394 that is configured to translate transversely in a bore 396 relative to the sutures 66. For such embodiments, the blade 392 may approximate the sutures 66 during transverse translation of the blade 392 so as to contact the sutures 66 with a sharpened edge 398 of the blade 392 and cut through the sutures 66 prior to the end of a corresponding transverse actuation stroke. In some cases, the suture cutter 390 may be disposed on the chassis portion 14 of the actuator assembly 12.

In use, embodiments of the vascular closure assembly 10 may be used to reduce the size of or eliminate the passage 216 in the tissue layer 64 disposed above and adjacent the access hole 124 in the blood vessel 128 so as to provide hemostasis with regard to the access hole 124 in the blood vessel 128 after a minimally invasive vascular procedure or the like. Such devices and procedures discussed herein for providing such hemostasis may do so indirectly without directly closing the access hole 124 in the blood vessel 128 or suturing or otherwise penetrating the wall portion 126 of the blood vessel 128 during the hemostasis process. This may be particularly useful in circumstances where the wall portion 126 of the blood vessel 128 is diseased or otherwise compromised such as by the presence of calcified plaque as well as many other circumstances.

Figure 49:
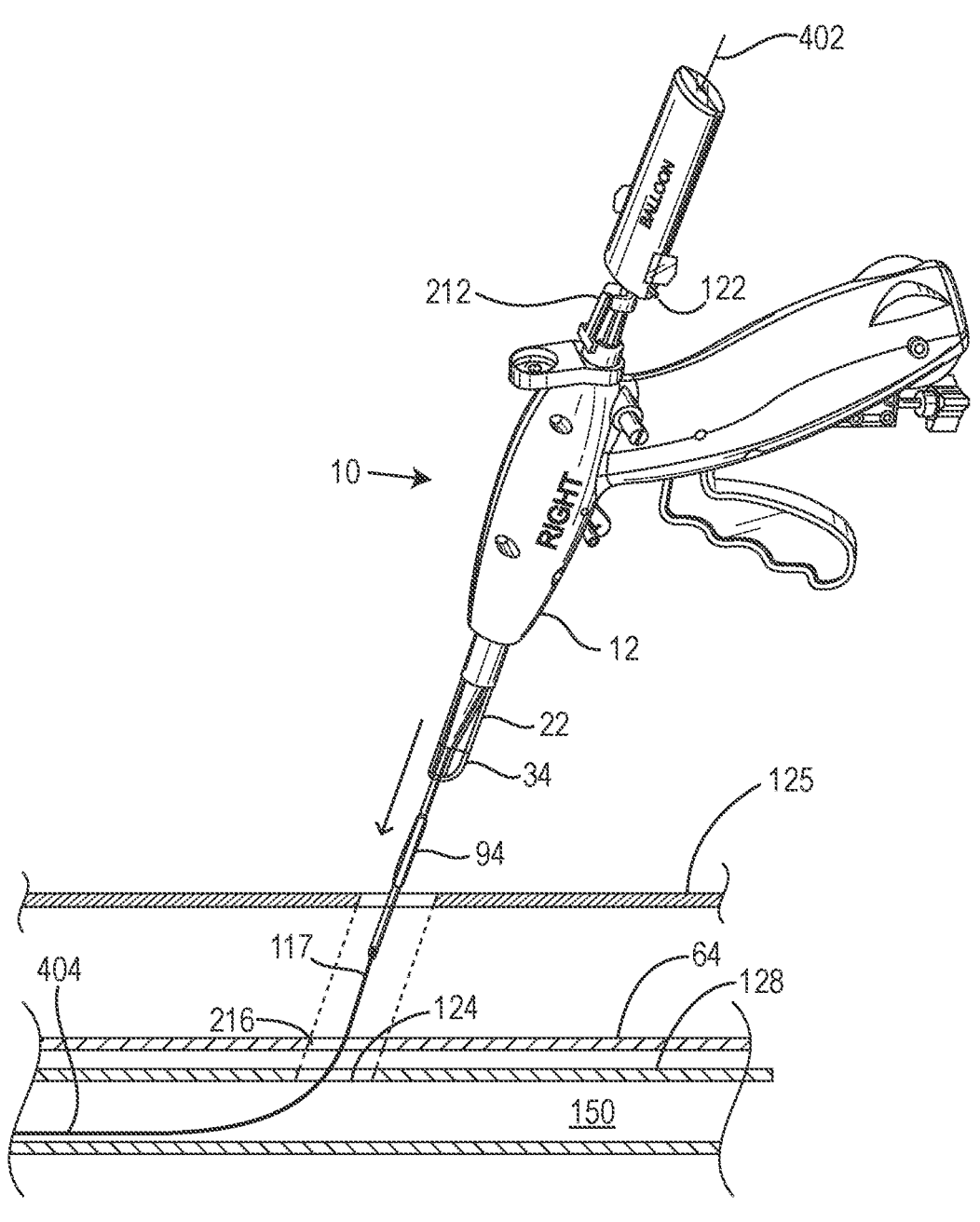
FIGS. 49-61 illustrate an embodiment of a vascular closure method utilizing the vascular closure assembly embodiment of FIG. 1.

Some embodiments of a method for vascular closure may include distally advancing the vascular closure assembly 10 over an exposed proximal portion 402 of the guidewire 117 which has a distal section 404 thereof disposed through the access hole 124 in a blood vessel 128 of the patient and through the passage 216 in the tissue layer 64 disposed above and adjacent the access hole 124 as shown in FIG. 49. The guidewire 117 is also disposed through the patient's skin layer 125 and the tissue disposed between the patient's skin 125 and the tissue layer 64. The method may further include distally advancing the vascular closure assembly 10 over the guidewire 117 while the inner catheter assembly 78 of the vascular closure assembly 10 is disposed within the inner lumen 32 of the elongate housing 22 of the actuator assembly 12 of the vascular closure assembly 10.

In some cases, the vascular closure assembly 10 may be so advanced with the self-inflating balloon 94 of the inner catheter assembly 78 extending distally beyond the distal end 28 of the elongate housing 22 and with the inner catheter assembly 78 releasably secured to the actuator assembly 12 by the inner catheter assembly position lock 212 to prevent relative axial displacement therebetween. In addition, advancing the vascular closure assembly 10 over the guidewire 117 may include, in some cases, distally advancing the guidewire lumen 114 of the elongate shaft 82 of the inner catheter assembly 78 of the vascular closure assembly 10 over the guidewire 117.

Figure 50:
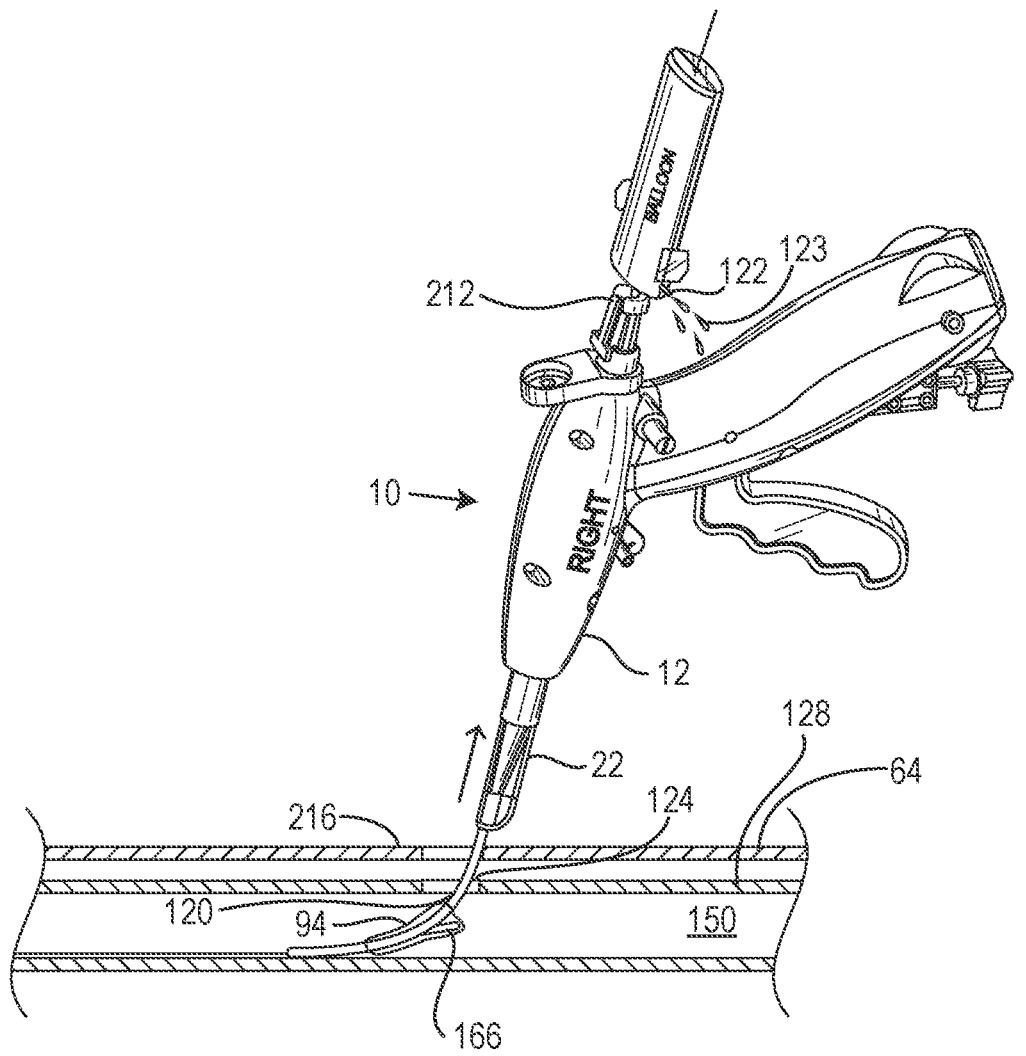

For some embodiments, the vascular closure assembly 10 may continue to be advanced until blood is observed being emitted from the proximal port 122 of the blood return lumen 118 of the inner catheter assembly 78 as shown in FIG. 50. The emission of blood 123 from the proximal port 122 indicates that the distal port 120 of the blood return lumen 118 is disposed within the inner lumen 150 of the patient's blood vessel 128 and suitably positioned for deployment of the foot extension 166. Typically, the distal section 34 of the elongate housing 22 is disposed at or below the patient's outer skin layer 125 at this stage as well.

The method thus includes deploying the foot extension 166 from the elongate shaft 82 of the inner catheter assembly 78. In some instances, the foot extension 166 is deployed from a position within the interior volume 98 of the self-inflating balloon 94 as shown in FIGS. 39 and 50. The foot extension 166 in this case is disposed along the elongate shaft 82 within the interior volume 98 of the self-inflating balloon 94 such that as the foot extension 166 extends radially outward from the elongate shaft 82 it may also push a portion of the wall 96 of the self-inflating balloon 94 radially outward, however, the wall 96 of the self-inflating balloon 94 may be configured to be thin and flexible enough to conform to the outer contour of the foot extension 166 and not interfere with the function of the foot extension 166. As discussed above, in some cases the foot extension 166 may be disposed axially coextensive with the self-inflating balloon 94, but not within the interior volume 98. For such embodiments, the foot extension 166 may be deployed from the position outside the interior volume 98.

Figure 50A:
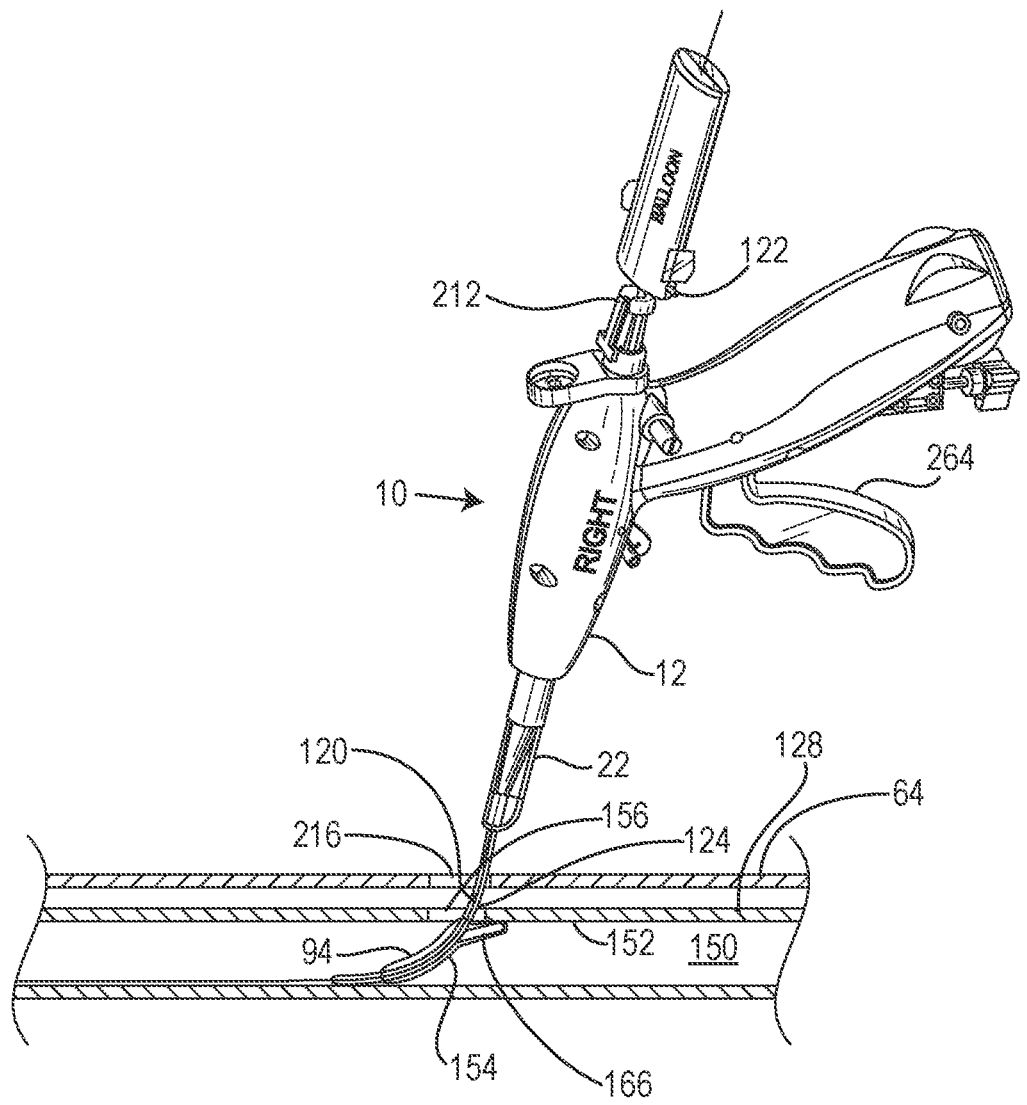

Once the foot extension 166 has been deployed, the vascular closure assembly 10 may be proximally retracted until contact or other mechanical interaction or abutment between the foot extension 166 and an inner surface 152 of the inner lumen 150 of the blood vessel 128 of the patient adjacent the access hole 124 prevents further proximal displacement of the inner catheter assembly 78 as shown in FIG. 50A. In this configuration, generally an axial portion of the self-inflating balloon 94 overlaps the access hole 124. In addition, it should be noted that in this configuration with the foot extension 166 deployed and preventing further proximal retraction of the vascular closure assembly 10 (or inner catheter assembly 78 only if the inner catheter assembly 78 is optionally not releasably secured to the actuator assembly 12) there will be a layer of the wall 96 of the self-inflating balloon 94 disposed between the outer surface of the foot extension 166 and the inner surface 152 of the blood vessel 128 even though the surfaces are mechanically opposed to each other.

Figure 37:
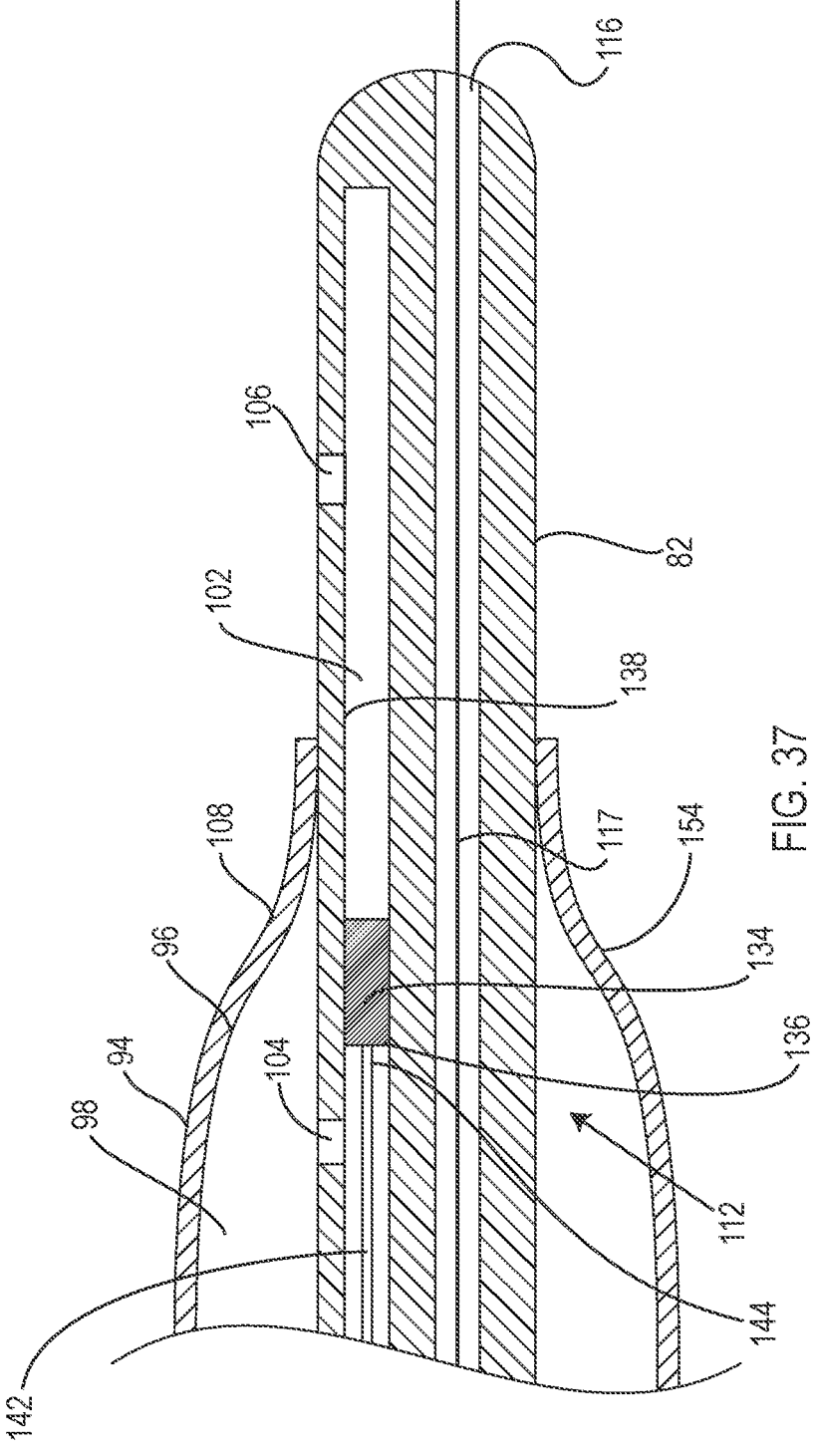
FIG. 37 shows the inner catheter assembly embodiment of FIG. 36 with the balloon inflation lumen in a closed state to prevent self inflation of the self-inflating balloon and to optionally permit venting of the interior volume of the self-inflating balloon.
Figure 51:
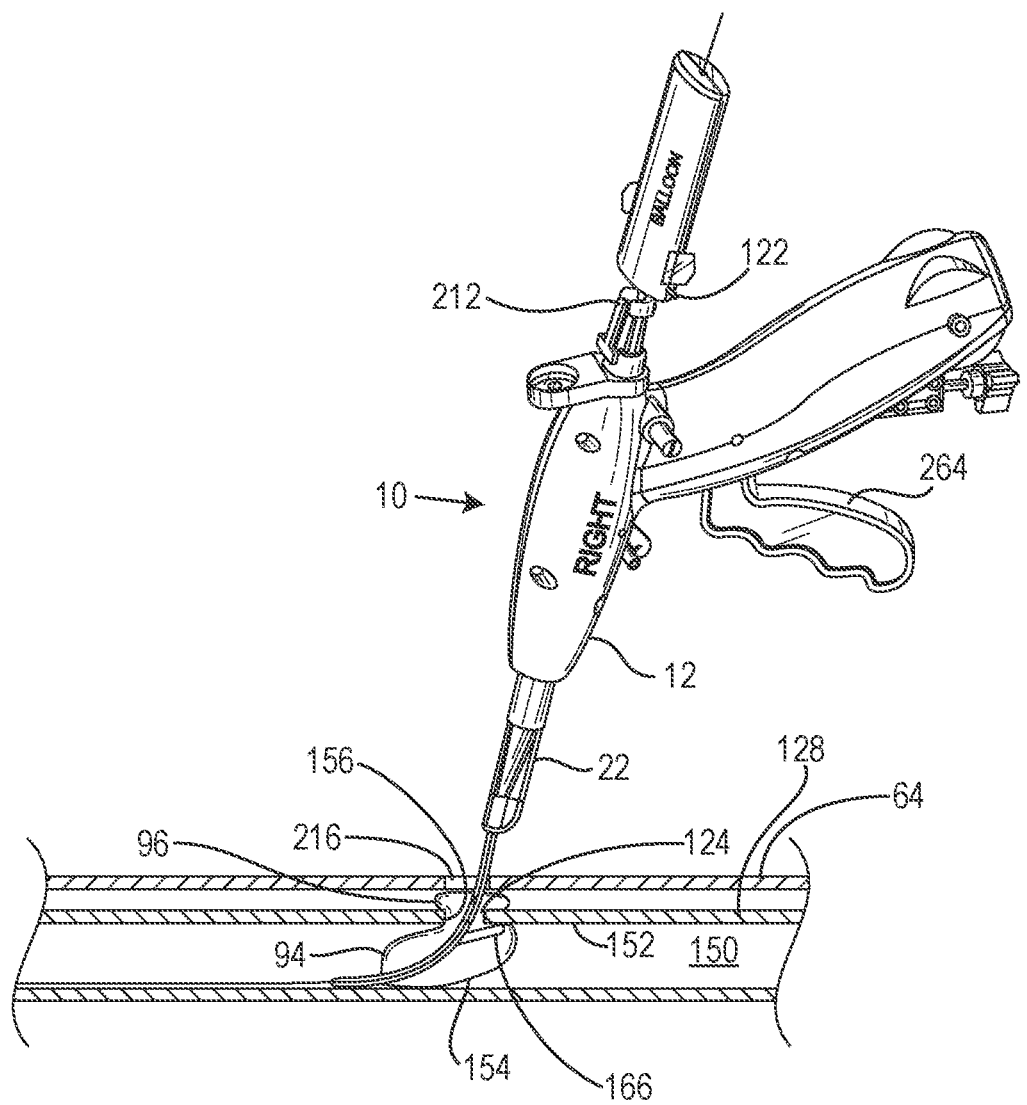

Once the self-inflating balloon 94 and foot extension 166 disposed therein are axially secured in place, the balloon inflation valve 112 of the inner catheter assembly 78 as shown in FIGS. 36 and 37 may be opened using the balloon inflation lever 148 allowing pressurized blood 123 from within the interior volume 150 of the patient's blood vessel 128 to flow through the balloon inflation lumen 102 of the inner catheter assembly 78 and into an interior volume 98 of the self-inflating balloon 94 as indicated by arrows 139. The self-inflating balloon 94 may continue to be allowed to inflate until contact and hemostasis is established between an outer surface 154 of the self-inflating balloon 94 and the perimeter surface 156 of the access hole 124 in the blood vessel 128 as shown in FIG. 51.

Figure 52:
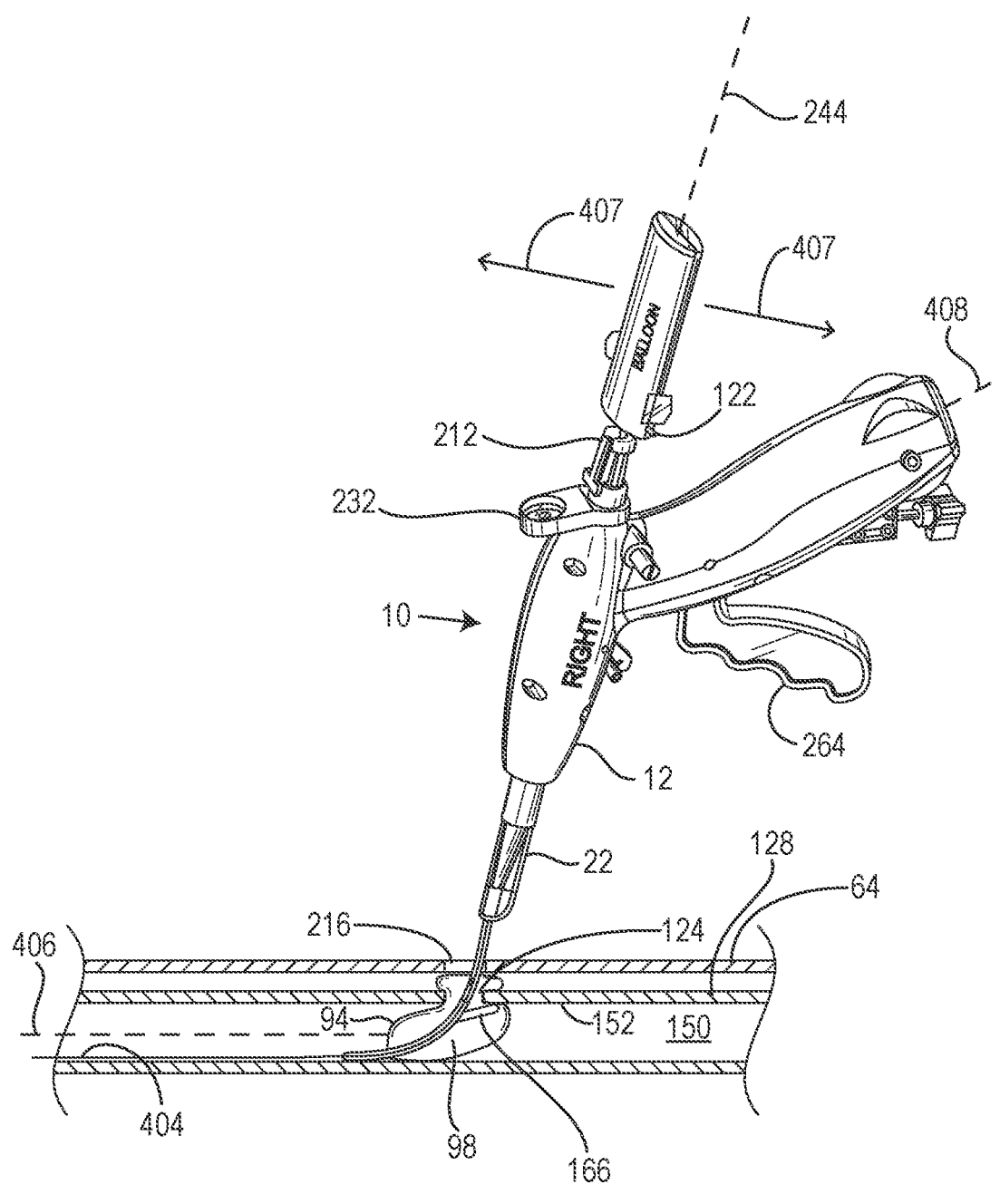

The inner catheter assembly 78 may then be released from the actuator assembly 12 by releasing the inner catheter assembly position lock 212 to allow the inner catheter assembly 78 to axially translate relative to the actuator assembly 12. The actuator assembly 12 is then distally advanced over the inner catheter assembly 78 while holding the inner catheter assembly 78 in a fixed axial position relative to the access hole 124 in the blood vessel 128 until the distal end 28 of an elongate housing 22 of the actuator assembly 12 is disposed adjacent the passage 216 in the tissue layer 64 as shown in FIG. 52. In some cases, the actuator assembly 12 may be distally advanced over the inner catheter assembly 78 until the proximal index 226 of the actuator assembly 12 is aligned with the insertion alignment mark 224 disposed on the inner catheter assembly 78.

This technique may be useful for a variety of patients having a variety of tissue morphologies in the area of the passage 216 in the tissue layer 64 and the access hole 124. Generally speaking, the distance between the tissue layer 64 (such as a fascia layer, for example) and the blood vessel wall 126 (such as a blood vessel wall 126 of a femoral artery, for example) is fairly consistent patient to patient, even though the distance between an outer surface of the patient's skin and the fascia layer 64 may vary greatly patient to patient.

In some cases, once in position, the inner catheter assembly 78 may then be releasably secured to the actuator assembly 12 by activating the inner catheter assembly position lock 212. In some instances, it may also be useful at this point to orient the longitudinal axis 244 of the elongate housing 22 relative to the longitudinal axis 406 of the blood vessel 128 of the patient as indicated by arrows 407 as shown in FIG. 52. Orienting the longitudinal axis 244 of the elongate housing 22 relative to the longitudinal axis 406 of the blood vessel 128 of the patient may include forming an angle of about 50 degrees to about 80 between the longitudinal axis 244 of the elongate housing 22 and the longitudinal axis 406 of the blood vessel 128. Orienting the longitudinal axis 244 of the elongate housing 22 relative to the longitudinal axis 406 of the blood vessel 128 of the patient may also include observing the angular alignment mechanism 232 and adjusting the angle between the longitudinal axis 244 of the elongate housing 22 and the longitudinal axis 406 of the blood vessel 128 until the ball bearing 248 disposed in the conical cavity 236 of the angular alignment mechanism 232 is centered at the axis of symmetry 238 of the conical cavity 236. It may also be useful to orient an axis 408 of the handle 46 of the actuator assembly 12 with the longitudinal axis 406 of the blood vessel 128 of the patient at this stage.

Figure 53:
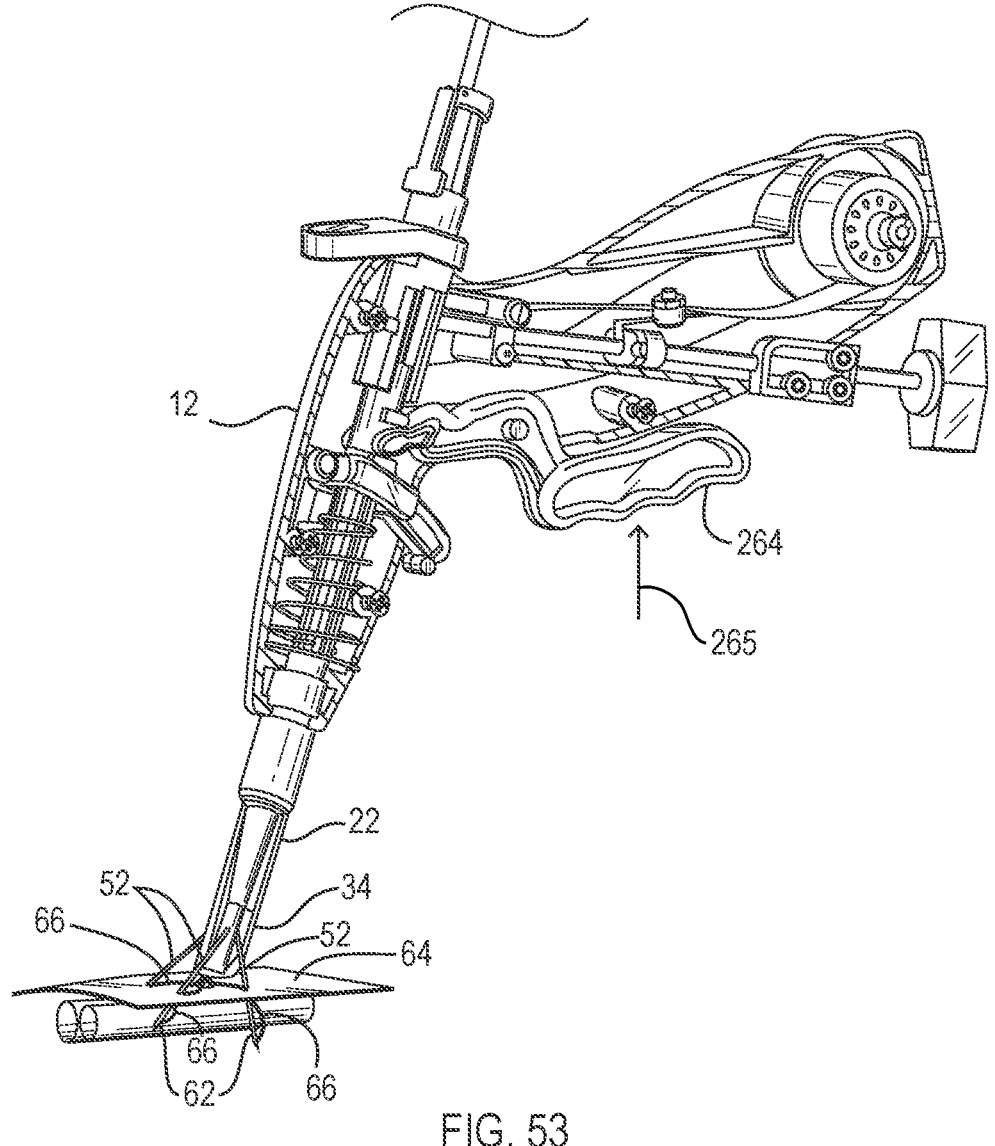
Figure 54:
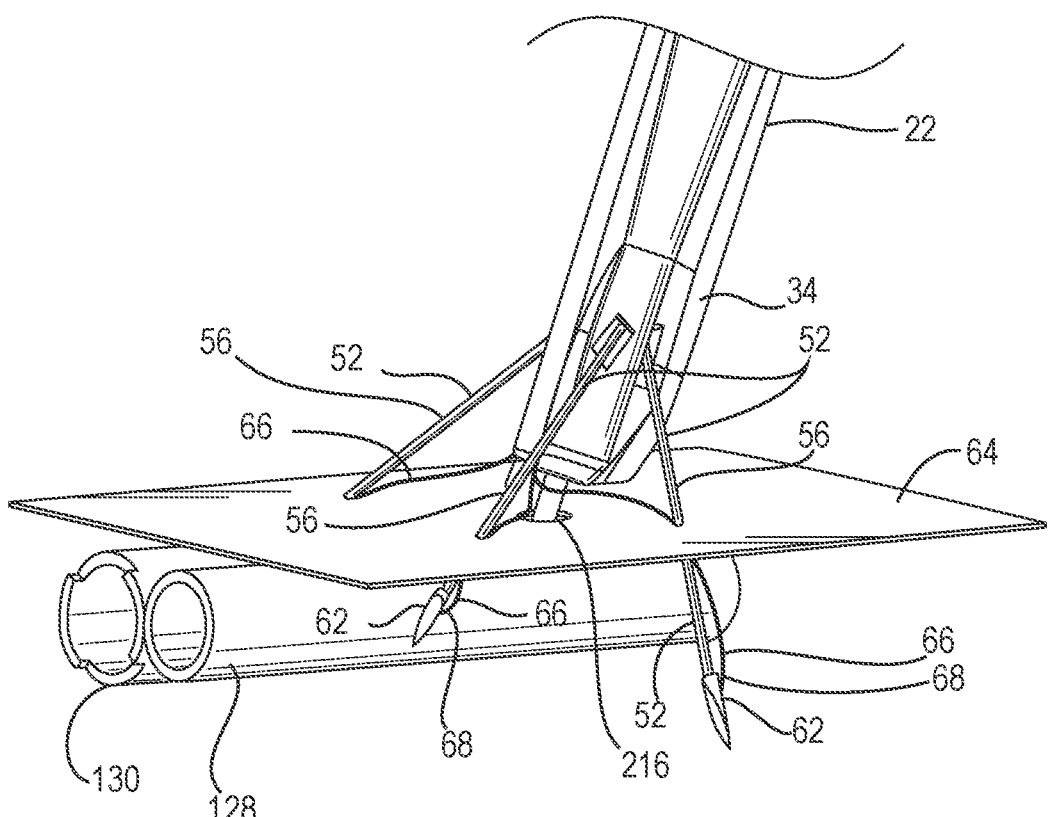

The plurality of anchor deployers 52 may now be deployed in a distal and radially outward direction away from a distal section 34 of the elongate housing 22 of the vascular closure assembly 10 by activating the actuating lever 264 of the anchor deployer actuator 256. For some embodiments, activating the actuating lever 264 may include depressing the actuator lever 264, as indicated by arrow 265 of FIG. 53, which is coupled to the anchor deployer carrier 258 which is operatively coupled to the proximal section 262 of each of the plurality of deployer rods 56 as shown in FIGS. 53 and 54. For some embodiments, depressing the actuator lever 264 results in rotation of the actuator lever 264, which in turn axially translates the anchor deployer carrier 258 and proximal section 262 of the plurality of deployer rods 56 in a distal direction. The anchor deployers 52 may deployed such that the anchors 62 extend distally beyond the distal end 28 of the elongate housing 22 and the tissue layer 64 is penetrated or otherwise engaged so as to support axial tension on the filaments 66 in positions disposed about the passage 216 in the tissue layer 64 with respective anchors 62 of the plurality of anchor deployers 52 as shown in FIG. 54. In some cases, deploying the plurality of anchor deployers 52 in a distal and radially outward direction away from the distal section 34 of the elongate housing 22 may include deploying the plurality of anchor deployers 52 in an asymmetric pattern about the longitudinal axis 244 of the elongate housing 22 as shown in FIG. 20 and discussed above.

The anchors 62 are secured to the tissue layer 64 in these positions disposed about the passage 216 in the tissue layer 64. In some cases, securing the anchors 62 to the tissue layer 64 in the positions disposed about the passage 216 in the tissue layer 64 may include penetrating the tissue layer 64 with each of the anchors 62 of the respective anchor deployers 52 and detaching each anchor 62 from its respective deployment rod 56 at a position beneath the tissue layer 64. Although anchor embodiments 62 are shown being deployed, anchor embodiments 62' or 62" or any other suitable anchor embodiment and associated anchor deployer embodiment 52 may be used for this method. At this stage, the actuator assembly 12 may also be optionally rotated and angularly oriented until the longitudinal axis 244 of the elongate housing 22 is substantially perpendicular to the longitudinal axis 406 of the blood vessel 128 after deploying the anchor deployers 52 and prior to proximally retracting deployment rods 56 of the anchor deployers 52. Such a perpendicular or substantially perpendicular orientation may be useful in some circumstances to facilitate a desired engagement of the anchor deployers 52 with the tissue layer 64.

Figure 55:
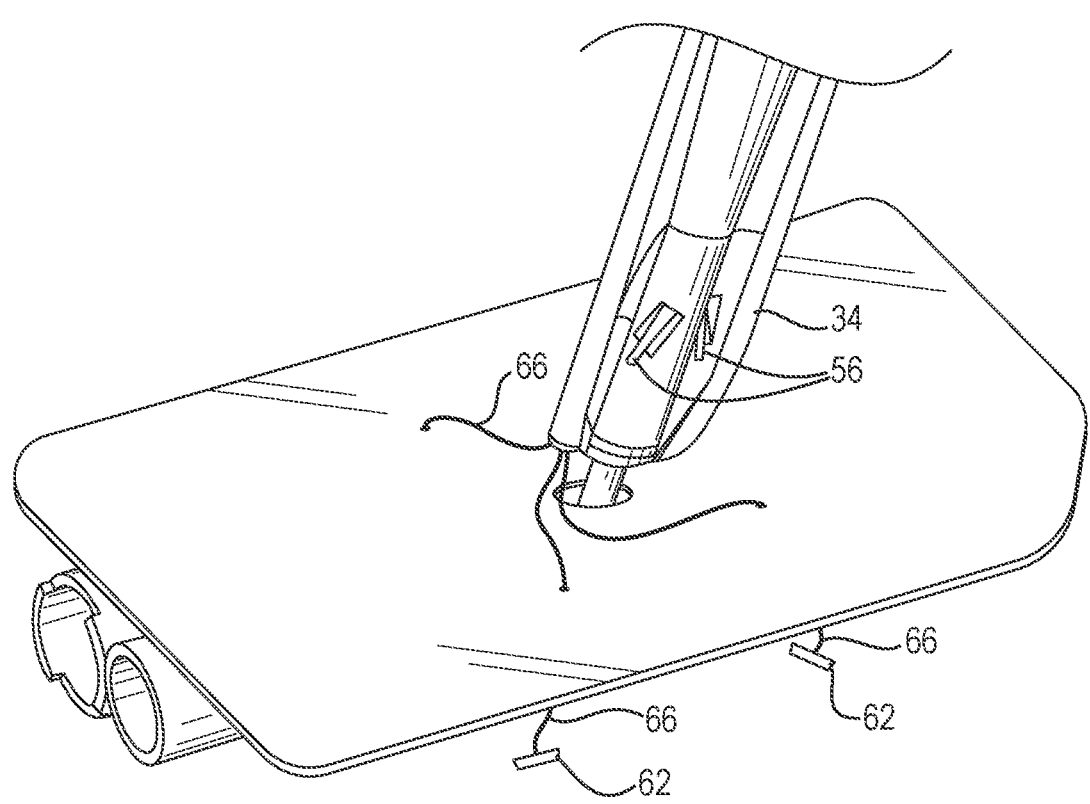
Figure 56:
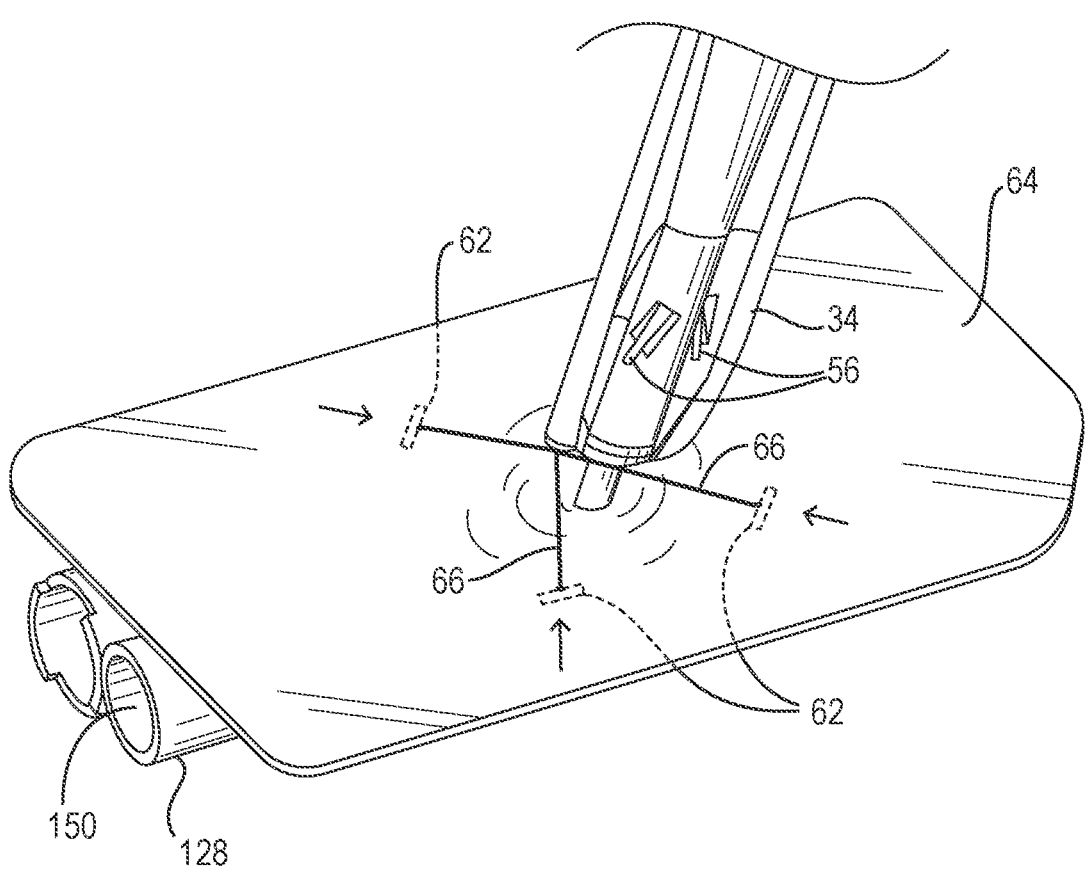

The deployment rods 56 of the anchor deployers 52 may then be proximally retracted into the elongate housing 22 by releasing the spring loaded anchor deployer actuator 256 or by any other suitable means as shown in FIG. 55. The anchors 62 may now be drawn closer together by applying proximal tension to the filaments 66 secured to each of the anchors 62. The anchors 62 and respective portions of the tissue layer 64 secured to each of the anchors 62 are thus drawn together closer to each other as the filaments 66 are tensioned and translated in an inward generally radial direction thereby reducing the transverse dimension of the passage 216 in the tissue layer 64 as shown in FIG. 56.

In some instances, applying proximal tension to the filaments 66 secured to each of the anchors 62 may include actuating the filament tensioning mechanism 336 which is configured to controllably apply a tension force to the filaments 66. For some embodiments, actuating the filament tensioning mechanism 336 may include controllably translating the filament terminal 338 which is secured to the filaments 66 and the tensioning spring 342. In addition, for some embodiments, controllably translating the filament terminal 338 may include rotating the knob 356 secured to the threaded rod 344 which is operatively coupled to the threaded bore 352 of the tension control block 348 wherein the tension transfer clip 354 releasably couples the filament terminal 338 to the tension control block 348 in an orientation that opposes the tension force of the tensioning spring 342. In addition, for such embodiments, rotating the knob 356 may reduce opposition of the tension force applied by the tension control block 348 in order to controllably apply the tension force of the tensioning spring 342 to the filaments 66. For such embodiments, the knob 356 may be so rotated until the tension control block 348 disengages the filament terminal 338 and all of the tension force from the tensioning spring 342 is applied to the filaments 66 through the filament terminal 338 as shown in FIG. 57.

The balloon inflation valve 112 of the inner catheter assembly 78 may then be closed at this stage by deactivating the balloon inflation lever 148 thus closing off the balloon inflation lumen 102 which prevents fluid communication between the interior volume 150 of the blood vessel 128 and the interior volume 98 of the self-inflating balloon 94. As such, inflation pressure from within the interior volume 150 of the blood vessel 128 is excluded from the interior volume 98 of the self-inflating balloon 94 and the interior volume 98 may also be vented to the ambient atmosphere back through the inflation port 104 and towards the proximal chassis 92 as shown in FIG. 37 thereby allowing the self-inflating balloon 94 to deflate. The inner catheter assembly position lock 212 may then be released and the elongate shaft 82 of the inner catheter assembly 78 and the self-inflating balloon 94 distally advanced slightly in order to relieve the mechanical interaction between the inner surface 152 of the blood vessel 128 and the deployed foot extension 166. The foot extension 166 may then be retracted back into the retracted position by deactivating the foot extension actuator 168 on the proximal chassis 92.

Figure 58:
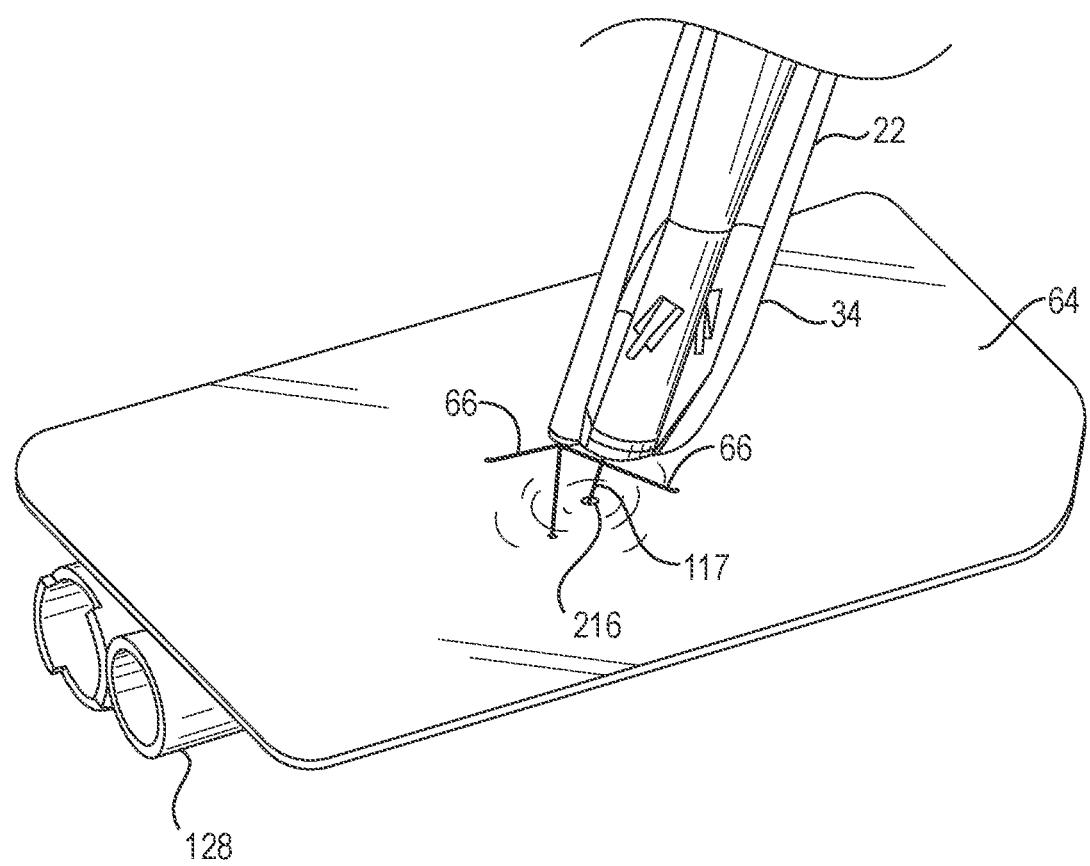
Figure 59:
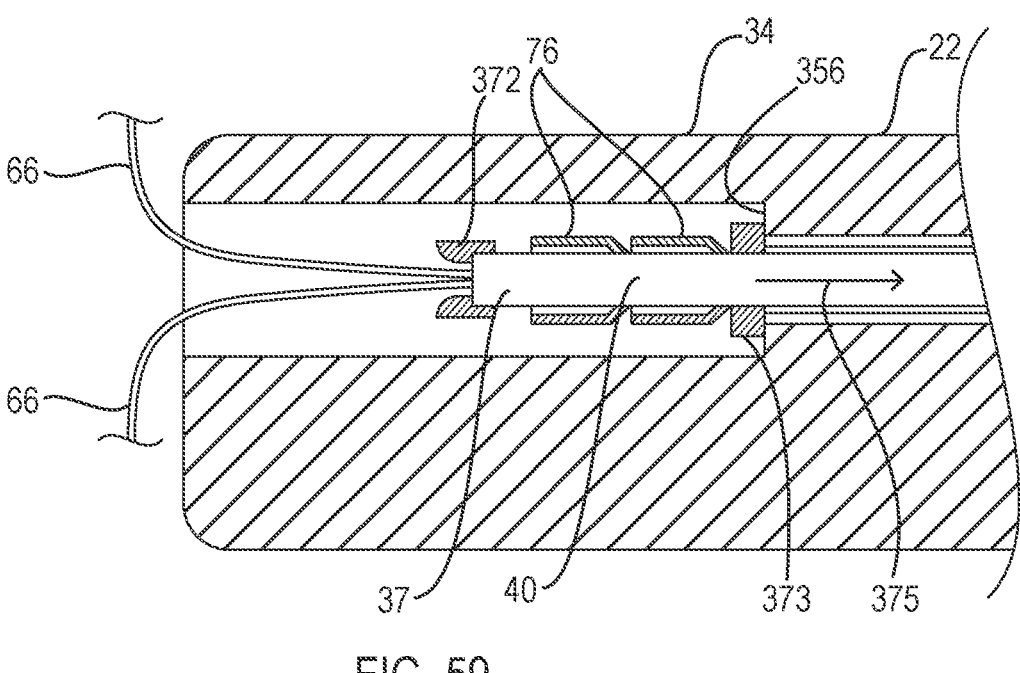

The inner catheter assembly 78 is then proximally withdrawn within and relative to the inner lumen 32 of the elongate housing 22 of the actuator assembly 12 until the proximal index 226 of the actuator assembly 12 is aligned with the retraction alignment mark 228 on the elongate shaft 82 of the inner catheter assembly 78. Such an axial alignment of the inner catheter assembly 78 and actuator assembly 12 indicates that the deflated self-inflating balloon 94 and the distal end 86 of the elongate shaft 82 have been proximally retracted into the inner lumen 32 of the elongate housing 22 and are no longer interacting with the access hole 124 or passage 216 in the tissue layer 64. This alignment may also indicate that the elongate shaft 82 of the inner catheter assembly 78 has been entirely withdrawn with only the guidewire 117 remaining in the passage 216 as shown in FIG. 58.

As the inner catheter assembly 78 is being withdrawn, the deflated self-inflating balloon 94 may be simultaneously withdrawn from the access hole 124 and passage 216 in the tissue layer 64 allowing the tension on the filaments 66 which are secured to the tissue layer 64 to fully close the passage 216 in the tissue layer 64. During this process, it should be noted that once tension force of the tensioning spring 342 has been applied to the anchored filaments 66, the tissue layer 64 disposed about the self-inflating balloon 94 is being tightened around the outside surface 154 of the self-inflating balloon 94 so as to provide hemostasis therebetween regardless of whether the self-inflating balloon 94 is in an inflated state or deflated state. The pressure of the tissue layer 64 disposed about the passage 216 which is disposed about the self-inflating balloon 94 is not so great, however, as to prevent the outside surface 154 of the self-inflating balloon 94 and elongate shaft 82 distal of the self-inflating balloon 94 to axially slide through the passage 216 of the tissue layer 64 during proximal withdrawal of the inner catheter assembly 78.

Figure 60:
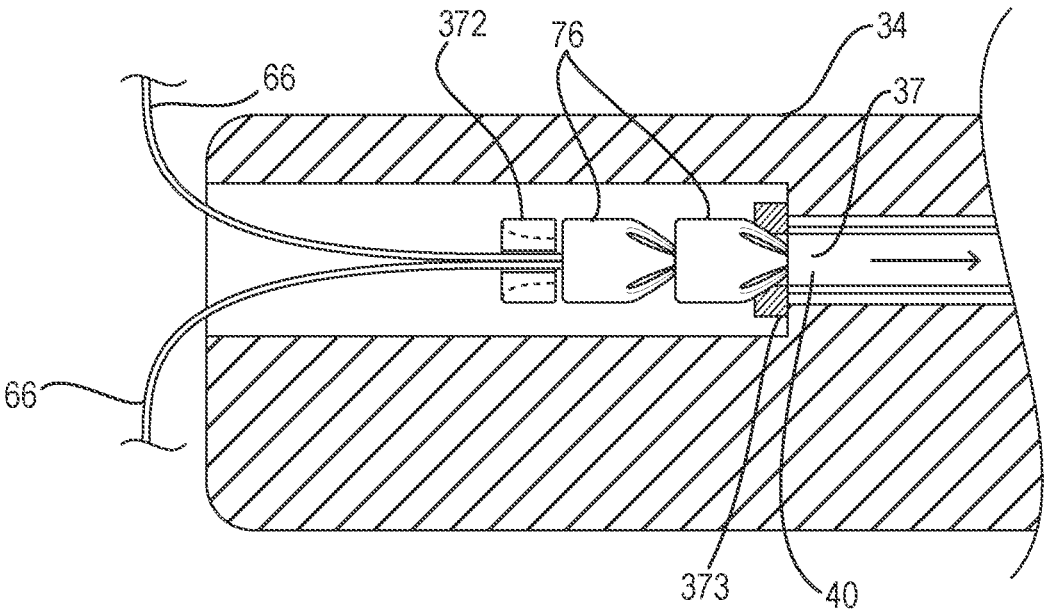

One or more filament locks 76 may then be deployed onto the filaments 66 at the distal end 28 of the elongate housing 22 by activating the filament lock mechanism 72 while maintaining tension force on the filaments 66 with the tensioning spring 342. In some cases, activating the filament lock mechanism 72 may include depressing the filament tube actuator 374 which is coupled to a filament tube 37 disposed about the filaments 66 in the elongate housing 22 thereby proximally retracting the filament tube 37 as shown by the arrow 375 in FIG. 59. The proximal retraction may be continued until at least one filament lock 76 in an expanded state is pushed off the distal end 364 of the filament tube 37 and onto the filaments 66 as shown in FIG. 60.

For such embodiments, the filament lock 76 may include a self-contracting configuration and the deployment method embodiment may further include allowing the self-contracting filament lock 76 to contract to a relaxed state over the filaments 66 thereby clamping the at least one filament lock 76 onto an outside surface of the filaments 66 and to each other once the outward radial support of the filament tube 37 is removed from within the filament lock 76. The outward radial support of the filament tube 37 against the inside surface of the filament lock 76 may be removed by proximally retracting the distal end 364 of the filament tube 37 past the distal shoulder 366 of the close fitting bore 362 and optional filament lock bushing 373 disposed about the distal end 364 of the filament tube 37. In some cases, a plurality of filament locks 76 may be deployed by pushing the plurality of filament locks 76 off the distal end 364 of the of the filament tube 37 and onto the filaments 66. For example, in some cases, 2, 3, 4, 5 or more filament locks 76 may be deployed onto the filaments 66 in order to secure the filaments 66 in a fixed relation to each other and lock them in a tensioned state.

For the filament lock embodiments 76 shown, clamping the at least one filament lock 76 onto the filaments 66 may include deflecting the plurality of proximally extending fingers 382 of the trailing lock filament lock embodiments 76 in an inward radial direction and clamping proximal ends 386 of the proximally extending fingers 382 onto the filaments 66. In some cases, the deployment may include wedging proximally extending fingers 382 of a distal-most trailing lock filament lock embodiment 76 into the inner lumen 370 of the proximally adjacent filament lock 76 during deployment.

Figure 61:
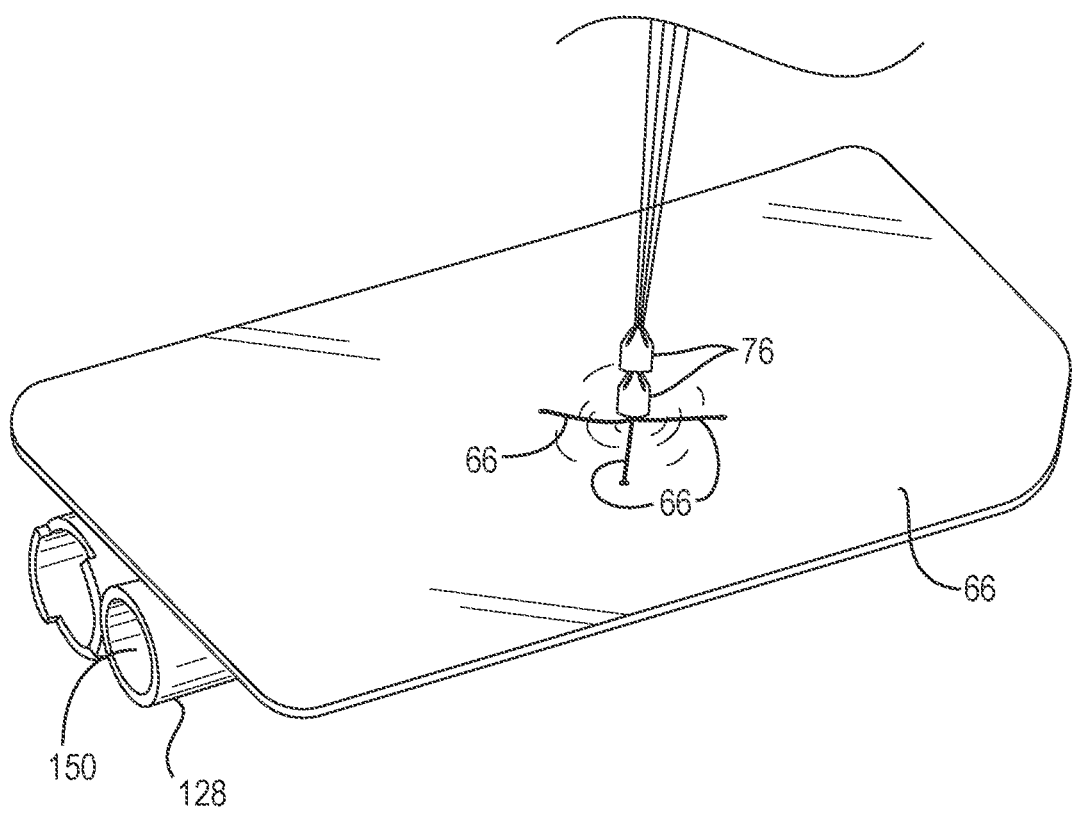

The filaments 66 may then optionally be cut at a position which is proximal of the filament lock 76 by actuating the filament cutter 390 of the actuator assembly 12. As discussed above, the filament cutter 390 and sharpened blade 392 thereof may be disposed in operative arrangement with the filaments 66. In some cases, the sharpened blade 392 of the tissue cutter 390 may be disposed in the slide 394 and actuating the filament cutter 390 of the actuator assembly 12 may include translating the slide 394 and sharpened blade 392 in the bore 396 relative to the filaments 66 thereby approximating the filaments 66 during transverse translation and contacting the filaments 66 with the sharpened edge 398 of the blade 392 thereby cutting through the filaments 66. Once the filaments 66 have been trimmed, the vascular closure assembly 10 may be withdrawn from the patient and treatment of the puncture site completed as shown in FIG. 61.

Embodiments illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation and use of such terms and expressions do not exclude any equivalents of the features shown and described or portions thereof, and various modifications are possible. The term "a" or "an" can refer to one of or a plurality of the elements it modifies (e.g., "a reagent" can mean one or more reagents) unless it is contextually clear either one of the elements or more than one of the elements is described. Thus, it should be understood that although embodiments have been specifically disclosed by representative embodiments and optional features, modification and variation of the concepts herein disclosed may be resorted to by those skilled in the art, and such modifications and variations are considered within the scope of this disclosure.

With regard to the above detailed description, like reference numerals used therein refer to like elements that may have the same or similar dimensions, materials and configurations. While particular forms of embodiments have been illustrated and described, it will be apparent that various modifications can be made without departing from the spirit and scope of the embodiments of the invention. Accordingly, it is not intended that the invention be limited by the forgoing detailed description.

What is claimed is:

1. An actuator assembly, comprising:

a chassis portion having an outer shell with an interior volume disposed within the outer shell;

an elongate housing with an axial length greater than a transverse dimension thereof, a proximal end secured to a distal end of the chassis portion, a distal end extending away from the chassis portion, an inner lumen extending along the elongate housing to the distal end of the elongate housing, a distal section, a filament lumen that extends along the elongate housing and terminates at a distal port disposed in the distal section of the elongate housing, and a plurality of anchor deployer lumens, each anchor deployer lumen extending axially along the elongate housing and terminating distally at a distal port disposed in the distal section of the elongate housing;

a plurality of anchor deployers, each anchor deployer being slidably disposed within a respective deployer lumen of the elongate housing and including a distal end which is configured to extend and spread from the distal section of the outer housing, each anchor deployer comprising:

a deployment rod which includes an elongate resilient configuration with an axial length greater than a transverse dimension and a distal end that extends from the distal section of the elongate housing upon distal axial deployment, an anchor which is removably secured to the distal end of the deployment rod, and a filament which is slidably disposed within the filament lumen of the elongate housing and which includes a distal end which is secured to the anchor; and a filament lock mechanism disposed at a distal end of the filament lumen including a filament lock disposed in operative arrangement with the filaments of the respective plurality of anchor deployers, wherein the filament lock mechanism includes:

a filament tube which has a distal section which is slidably disposed in a close fitting bore at the distal section of the elongated housing, which has a distal end which extends distally beyond a distal shoulder surface of the close fitting bore, which is slidably disposed relative to the elongate housing, which has an inner lumen disposed about the filaments, and which has a proximal section, a filament lock which has an inner lumen which is disposed about the distal end of the filament tube in an axial position that is distal of the distal shoulder surface of the close fitting bore and which is self-contracting from an expanded state to a relaxed state and configured to clamp onto the filaments disposed in the inner lumen of the filament tube once an outward radial support producing the expanded state of the filament tube is removed, and a filament tube actuator which is operatively coupled to the proximal section of the filament tube and which is configured to axially retract the filament tube relative to the distal shoulder surface upon activation so as to push the filament lock off of the distal end of the filament tube and allow the filament lock to clamp onto the filaments disposed in the inner lumen of the filament tube, wherein the filament lock comprises a tubular structure including a main body portion and also including a plurality of fingers extending proximally from the main body portion, the fingers being of sufficient axial length and elastically biased towards a center longitudinal axis of the main body portion such that respective distal ends of the fingers are configured to be self-contracting from an expanded state to a relaxed state and clamp onto the filaments disposed within the inner lumen of the filament lock when the fingers are in the relaxed state and the fingers may be elastically spread to a relative transverse separation to the expanded state sufficient to fit onto an outer surface of the distal end of the filament tube.

2. The actuator assembly of claim 1 further comprising an anchor deployer actuator comprising:

an anchor deployer carrier which is slidably disposed with respect the chassis portion and which is operatively coupled to a proximal section of each of the plurality of deployer rods, and an actuator lever which extends outside of the chassis portion and which is operatively coupled to the anchor deployer carrier in order to translate the anchor deployer carrier in a distal direction upon actuation translation and thereby axially translate each of the deployer rods in a distal direction upon actuation translation.

3. The actuator assembly of claim 1 wherein a distal section of each of the anchor deployer lumens comprises a curved contour with respect to a longitudinal axis of a nominal anchor deployer lumen section disposed proximal to the distal section of the anchor deployer lumen to provide outward angular deflection of the anchor deployer extending outwardly from the distal port of the anchor deployer lumen.

4. The actuator assembly of claim 3 wherein the curved contour of the distal section of each of the anchor deployer lumens comprises a discharge axis that forms an angle of about 15 degrees to about 35 degrees with respect to the longitudinal axis of the nominal anchor deployer lumen section disposed proximal to the distal section of the anchor deployer lumen.

5. The actuator assembly of claim 3 wherein the curved contour of the distal section of a first anchor deployer lumen comprises a discharge axis forming a first angle with respect to the longitudinal axis of the nominal anchor deployer lumen section disposed proximal of the distal section of the anchor deployer lumen, and the curved contour of the distal section of a second anchor deployer lumen comprises a discharge axis forming a second angle with respect to the longitudinal axis of the nominal anchor deployer lumen section disposed proximal of the distal section of the anchor deployer lumen, the second angle being different from the first angle.

6. The actuator assembly of claim 1 wherein the distal end of each of the anchor deployer lumens comprises a recessed pocket having an inside surface which is configured to accept an outer surface contour of a respective anchor disposed therein with a close fit therebetween.

7. The actuator assembly of claim 1 wherein each anchor of the plurality of anchor deployers includes a sharpened distal tip which is configured to penetrate tissue in a distal direction.

8. The actuator assembly of claim 1 wherein the each deployment rod of the plurality of anchor deployers comprises a sharpened tissue penetrating tip disposed on the distal end of the deployment rod and the anchor which is removably secured to the distal end of the deployment rod has a tubular configuration without a sharpened distal tip.

9. The actuator assembly of claim 1 further comprising a filament tensioning mechanism configured to controllably apply axial tension to the filaments of the respective plurality of anchor deployers.

10. The actuator assembly of claim 9 wherein the filament tensioning mechanism includes a filament terminal which is secured to the filaments of the plurality of anchor deployers, a tensioning spring which is operatively secured to the filament terminal and wherein the filament terminal is translatable from a first position wherein there is no tension force applied to the filaments by the filament terminal and a second position wherein the tension force is applied to the filaments by the tensioning spring through the filament terminal.

11. The actuator assembly of claim 1 further comprising a filament cutter disposed in operative arrangement with the filaments of the respective plurality of anchor deployers.

12. The actuator assembly of claim 11 wherein the filaments comprise sutures and the filament cutter comprises a suture cutter including a sharpened blade that is angled towards the sutures and disposed in a slide that is configured to translate transversely in a bore relative to the sutures such that the blade approximates the sutures during transverse translation so as to contact the sutures and cut through them prior to the end of a corresponding transverse actuation stroke.

* * * * *